(12) United States Patent
Anémian et al.

(10) Patent No.: US 10,403,833 B2
(45) Date of Patent: *Sep. 3, 2019

(54) ORGANIC METAL COMPLEXES

(71) Applicant: Merck Patent GmbH, Darmstadt (DE)

(72) Inventors: Rèmi Manouk Anémian, Seoul (KR); Noriyuki Matsuda, Chiba (JP)

(73) Assignee: Merck Patent GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/650,485

(22) Filed: Jul. 14, 2017

(65) Prior Publication Data

US 2017/0317298 A1    Nov. 2, 2017

Related U.S. Application Data

(62) Division of application No. 14/370,197, filed as application No. PCT/EP2012/005205 on Dec. 17, 2012, now Pat. No. 9,748,502.

(30) Foreign Application Priority Data

Jan. 16, 2012 (EP) .................... 12000218

(51) Int. Cl.
| | |
|---|---|
| *C07F 15/00* | (2006.01) |
| *H01L 51/00* | (2006.01) |
| *C09K 11/06* | (2006.01) |
| *H05B 33/14* | (2006.01) |
| *A61N 5/06* | (2006.01) |
| *H01L 51/50* | (2006.01) |

(52) U.S. Cl.
CPC ........ *H01L 51/0087* (2013.01); *A61N 5/0616* (2013.01); *C07F 15/0086* (2013.01); *C09K 11/06* (2013.01); *H05B 33/14* (2013.01); *A61N 2005/0653* (2013.01); *C09K 2211/185* (2013.01); *H01L 51/5016* (2013.01); *Y02E 10/549* (2013.01)

(58) Field of Classification Search
CPC .................................................. C07F 15/0086
See application file for complete search history.

(56) References Cited

U.S. PATENT DOCUMENTS

| | | | |
|---|---|---|---|
| 7,094,897 B2 | 8/2006 | Stossel et al. | |
| 7,442,797 B2 | 10/2008 | Itoh et al. | |
| 8,779,176 B2 | 7/2014 | Anemian et al. | |
| 9,748,502 B2 * | 8/2017 | Anemian | ............... C09K 11/06 |
| 2006/0202197 A1 | 9/2006 | Nakayama et al. | |
| 2007/0103060 A1 | 5/2007 | Itoh et al. | |
| 2010/0227978 A1 * | 9/2010 | Stoessel | ............... C07D 213/30 |
| | | | 525/326.7 |
| 2013/0065873 A1 * | 3/2013 | Anemian | ............ C07F 15/0033 |
| | | | 514/187 |

FOREIGN PATENT DOCUMENTS

| | | | | |
|---|---|---|---|---|
| CN | 1875026 A | 12/2006 | | |
| CN | 100445294 C | 12/2008 | | |
| JP | 2004533430 A | 11/2004 | | |
| JP | 2006232784 A | 9/2006 | | |
| JP | 2006290988 A | * 10/2006 | | |
| JP | 2008-103535 A | 12/2006 | | |
| JP | 2006290988 A | 12/2006 | | |
| KR | 20130043459 A | 4/2013 | | |
| WO | WO-2005112520 A1 | 1/2005 | | |
| WO | WO-2005042444 A2 | 5/2005 | | |
| WO | WO-2009060742 A1 | 5/2009 | | |
| WO | WO-2011000873 A1 * | 1/2011 | .......... | C07F 15/0086 |
| WO | WO-2011141120 A1 * | 11/2011 | .......... | C07F 15/0033 |

OTHER PUBLICATIONS

International Search Report for PCT/EP2012/005205 dated Mar. 5, 2013.

* cited by examiner

*Primary Examiner* — Matthew P Coughlin
(74) *Attorney, Agent, or Firm* — Drinker Biddle & Reath LLP

(57) ABSTRACT

The present invention relates inter alia to novel organic metal complexes comprising, e.g., platinum and specific side groups, their preparation und their use in electronic devices.

14 Claims, No Drawings

ORGANIC METAL COMPLEXES

CROSS-REFERENCE TO RELATED APPLICATIONS

This application is a Divisional application of U.S. Ser. No. 14/370,197 filed Jul. 1, 2014 which is incorporated by reference in its entirety. U.S. Ser. No. 14/370,197 is a national stage application (under 35 U.S.C. § 371) of PCT/EP2012/005205, filed Dec. 17, 2012, which claims benefit of European application 12000218.3, filed Jan. 16, 2012, all of which are incorporated herein by reference in their entirety.

The present invention relates inter alia to new metal complexes, their preparation and devices comprising these metal complexes.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials being employed here are increasingly organometallic complexes which exhibit phosphorescence instead of fluorescence (M. A. Baldo et al., Appl. Phys. Lett. 1999, 75, 4 6). For quantum-mechanical reasons, an up to four-fold increase in energy and power efficiency is possible using organometallic compounds as phosphorescence emitters. In general, however, there is still a need for improvement in OLEDs which exhibit phosphorescent emission, in particular with respect to efficiency, operating voltage and lifetime. This applies, in particular, to OLEDs which emit in the relatively short-wave range, i.e. green and blue. Furthermore, many phosphorescent emitters do not have adequate solubility for processing from solution, so there is also a further need for improvement here.

In accordance with the prior art, the phosphorescent emitters employed in phosphorescent OLEDs are, in particular, iridium and platinum complexes, which are usually employed as cyclometallated complexes. The ligands here are frequently derivatives of phenylpyridine. However, the solubility of such complexes is frequently low, which makes processing from solution more difficult or prevents it completely.

For the OELD devices using such phosphorescent material, those devices using various complexes with iridium as the center metal have been developed up to the present, and the development for complexes using platinum as the center metal has also been progressed.

U.S. Pat. No. 6,303,238 discloses organic light emitting devices comprising a heterostructure for producing electroluminescence wherein the heterostructure is comprised of an emissive layer containing a phosphorescent dopant compound, whereby the dopant has a platinum octahedrylporphine-type structure. The compounds disclosed show good color purity but low external quantum efficiency (approx. 4%). Thus, further improvement for the luminous efficiency is demanded.

Further, it has also been reported that an ortho-metalated platinum complexes with aryl pyridines as a ligand and with platinum as the metal is useful as a phosphorescent material (JP 2001-181617) and a platinum complex using a bi-aryl skeleton compound as a ligand has also be reported (JP 2002-175884, JP 4110173, JP 2006-232784). However, the compounds disclosed here show low efficiency, high roll-off and low color purity.

As described above, various studies have been made vigorously for practical use of display devices in the next generation and, among them, organic EL devices using the phosphorescent material is particularly highlighted with a view point of improving the characteristics of the devices.

However, the study has been quite primitive and includes various subjects such as optimization of light emission characteristics, luminous efficiency, color purity, and structure of the devices. For solving such subjects, it has been demanded for the development of novel phosphorescent material and, further, for the development of efficient method of supplying the material.

The problem to be solved by the invention is, therefore, to provide new compounds with improved light emitting capabilities, preferably compounds with preferential luminous efficiency, low roll-off, long lifetime, and high color purity.

Surprisingly, it has been found, that the problem can be solved by the compounds as described below.

Thus the present invention relates to compounds having the general Formula (1),

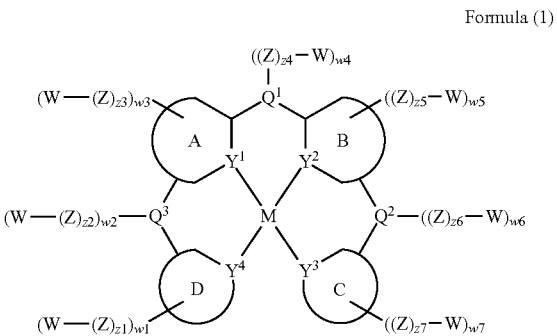

Formula (1)

where the following applies to the symbols and indices used:

M is a transition metal or metal ion, preferably a metal or metal ion selected from the Platinum Group (i.e. Fe, Co, Ni, Ru, Rh, Pd, Os, Ir, Pt) or gold, particularly preferably from Pt(II), Pd(II), Ni(II), Rh(I), Ir(I) und Au(III), very particularly preferably from Pt(II), Ir(I) und Au(III) and even more preferably from Pt(II);

A, B, C, D each represent a aromatic or heteroaromatic ring, condensed ring system or polycyclic ring system which may or may not be substituted with one or more rests $R^1$;

at least two of $Y^1$, $Y^2$, $Y^3$, and $Y^4$ represent nitrogen atoms which are bonded to M via coordination bonds and the remaining two of them represent carbon atoms (C) or nitrogen atoms (N), preferably $Y^1$=N, $Y^2$=C, $Y^3$=N and $Y^4$=C or =N, $Y^2$=N, $Y^3$=C and $Y^4$=C or $Y^1$=C, $Y^2$=C, $Y^3$=N and $Y^4$=N, particularly preferably $Y^1$=N, $Y^2$=N, $Y^3$=C and $Y^4$=C or $Y^1$=C, $Y^2$=C, $Y^3$=N and $Y^4$=N and very particularly preferably $Y^1$=C, $Y^2$=C, $Y^3$=N and $Y^4$=N;

$Q^i$ with i=1, 2, 3 are bridging units; the bridging units $Q^i$ preferably represent, independently from each other, a single bond, rings, preferably 5-membered rings, comprising at least one N-atom, which are condensed to both neighboring rings, i.e. $Q^3$ may be condensed to ring D and ring A or $Q^2$ may be condensed to ring B and C, single bonds or bivalent atoms or groups, preferably $C(R^1)_2$, N—$R^1$, P—$R^1$, or Si—$(R^1)_2$, particularly preferably N—$R^1$, P—$R^1$, or Si—$(R^1)_2$, wherein if W is attached to a $Q^i$ the rest W is bonded to $Q^i$ via N, P or Si—$R^1$ w1 to w7 (wi, i=1 to 7) are, independently of each other, either 0 or 1 wherein $$\sum_{i=1}^{7} wi = 1 \text{ or } 2,$$

preferably 1;

z1 to z7 (zi, i=1 to 7) are, independently of each other, either 0 or 1, wherein if wi=0 then zi is also 0; if zi=0 and wi>0 then W bonded to $Q^i$ or to ring A, B, C, or D via a single bond;

W is equal to the compound having the general Formula (2)

Formula (2)

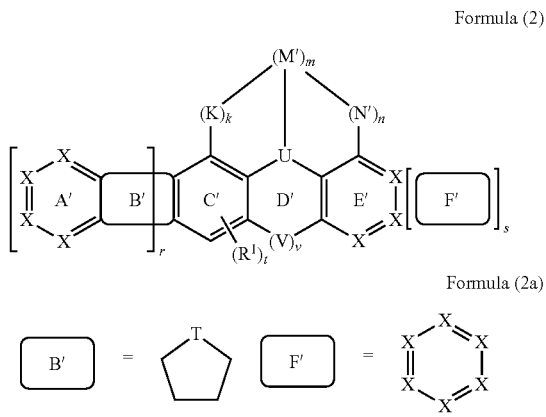

Formula (2a)

where the rings B' and F' can be any desired with one or more $R^1$ substituted or unsubstituted aliphatic, aromatic or heteroaromatic ring having 5 to 60 atoms or a substituted or unsubstituted polycyclic ring system, which may be condensed with the adjacent rings in any possible manner, where, in a preferred embodiment, the rings B' and F' are the compounds of the Formula (2a), which may be condensed with the adjacent ring C' and E', respectively, in any possible manner; and wherein X is, identically or differently on each occurrence selected from $CR^1$ or N;

T is selected, identically or differently on each occurrence, from the group consisting of —$C(R^1)_2$, —$Si(R^1)_2$, —N, —$NR^1$, —O, —S, —C(=O), —S(=O), —$SO_2$, —$CF_2$, —$SF_4$, —P, —P(=O)$R^1$, —$PF_2$, —P(=S)$R^1$, —As, —As(=O), —As(=S), —Sb, —Sb(=O) and —Sb(=S);

U is, if m=0, selected from the group consisting of —$C(R^1)_2$, —$Si(R^1)_2$, —N, —$NR^1$, —O, —S, —C(=O), —S(=O), —$SO_2$, —$CF_2$, —$SF_4$, —P, —P(=O)$R^1$, —$PF_2$, —P(=S)$R^1$, —As, —As(=O), —As(=S), —Sb, —Sb(=O) and —Sb(=S) and if m=1 it is selected from —$CR^1$, —$SiR^1$, —N;

V is selected, independently on each occurrence, from $C(R^1)_2$, $NR^1$, O, S, $R^1$ is, identically or differently on each occurrence, H, D, F, Cl, Br, I, $N(R^2)_2$, CN, $NO_2$, $Si(R^2)_3$, $B(OR^2)_2$, C(=O)$R^2$, P(=O)$(R^2)_2$, S(=O)$R^2$, S(=O)$_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, C=$NR^2$, P(=O)$(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; two or more radicals $R^1$ here may also form a mono- or polycyclic, aliphatic, aromatic and/or benzo-fused ring system with one another;

$R^2$ is, identically or differently on each occurrence, H, D, F, Cl, Br, I, $N(R^3)_2$, CN, $NO_2$, $Si(R^3)_3$, $B(OR^3)_2$, C(=O)$R^3$, P(=O)$(R^3)_2$, S(=O)$R^3$, S(=O)$_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, C=$NR^3$, P(=O)$(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or a diarylamino group, diheteroarylamino group or arylheteroarylamino group having 10 to 40 aromatic ring atoms, which may be substituted by one or more radicals $R^3$, or a combination of two or more of these groups; two or more adjacent radicals $R^2$ here may form a mono- or polycyclic, aliphatic or aromatic ring system with one another;

$R^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic or aromatic ring system with one another;

K is, if m=1, $C(R^1)_2$ or a single bond between M' and ring C'; and if m=0 then k=1 and K is $R^1$;

M' is a phenyl which is either unsubstituted or substituted by one or more rests $R^1$;

N' is, if m=1, $C(R^1)_2$ or a single bond between M' and ring E'; and if m=0 then n=1 and N' is $R^1$;

k is either 0 or 1; if k is 0 then M' and ring C' are not bonded via K to each other;

m is either 0 or 1, wherein if r=0 then m=1;

n is either 0 or 1; if n=0 then M and ring E' are not bonded via N to each other;

r is 0, 1 or 2; r is 1 or 2 if m=0;

s is 0 or 1, preferably 0;

t is 3 if r is 1 or 2 and t is 1 if r=0;

v is 0 or 1; if v=0 then ring D' is a 5 membered ring;

Z is, identically or differently on each occurrence, a spacer group.

Z serves as so-called spacer or spacer group. Spacers Z which can be employed are all groups known for this purpose to the person skilled in the art.

Z is preferably a linear or branched alkylene group having 1 to 20 C atoms, particularly preferably having 1 to 12 C atoms, in which one or more non-adjacent CH₂ groups may be replaced by —O—, —S—, —NH—, —N(CH₃)—, —N—CO—, —N—CO—O—, —N—CO—N—, —CO—, —O—CO—, —S—CO—, —O—COO—, —CO—S—, —CO—O—, —CH(halogen)-, —CH(CN)—, —CH═CH— or —C≡C—, or a cyclic alkyl group, preferably cyclohexane or a cyclohexane derivative with 1,4- or 1,3-linking, or an unsubstituted or with one or more R¹ unsubstituted aromatic or heteroaromatic ring, ring system or polycyclic ring system having 2 to 40 C-atoms, or an alkoxy group having 1 to 20 C-atoms, or an aryloxy group having 6 to 40 C-atoms, or a silyl group.

Preferably Z is an unsubstituted or with one or more R¹ unsubstituted aromatic or heteroaromatic ring, ring system or polycyclic ring system having 2 to 40 C-atoms, or an aryloxy group having 6 to 40 C-atoms, Examples of possible spacer groups Z are, for example, —(CH₂)ₒ—, —(CH₂CH₂O)ₚ—CH₂CH₂—, —CH₂CH₂—S—CH₂CH₂— or —CH₂CH₂—NH—CH₂CH₂—, where o=2 to 12 and p=1 to 3, but also —O—.

Particularly preferred spacer groups Z are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene or butenylene.

In a preferred embodiment the compound according to Formula (1) is characterized in that either $Q^2$ or $Q^3$ is a single bond, even more preferably both $Q^2$ and $Q^3$ are both single bonds according to the following general Formula (3).

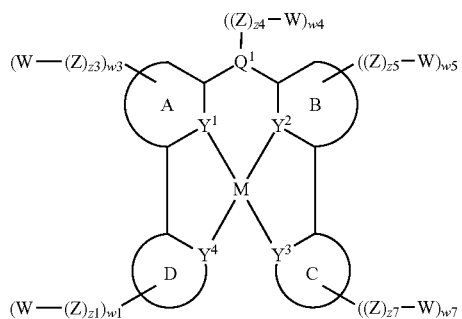

Formula (3)

wherein the sum of wi (i=1, 3, 4, 5 and 7) is 1 or 2, preferably 1 and wherein the other symbols are defined as above.

Preference is given to a compound according to Formula (1) having the following general Formula (4).

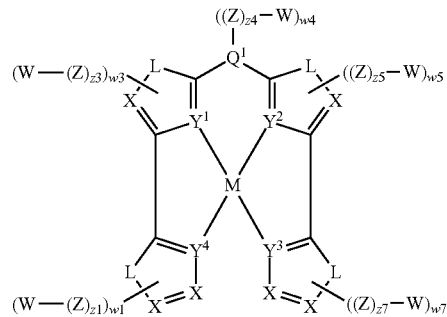

Formula (4)

wherein the sum of wi (i=1, 3, 4, 5 and 7) is 1 or 2, preferably 1, and wherein L is, identically or differently on each occurrence, X═X, R¹C═N, O, S, Se or NR¹ and wherein the other symbols and indices are defined as above. Preferably L is, identically or differently on each occurrence, X═X, R¹C═N, S, or NR¹, particularly preferably identically or differently on each occurrence, X═X or S, very particularly preferably X═X.

Preferably, the present invention relates to a compound according to the following Formula (5).

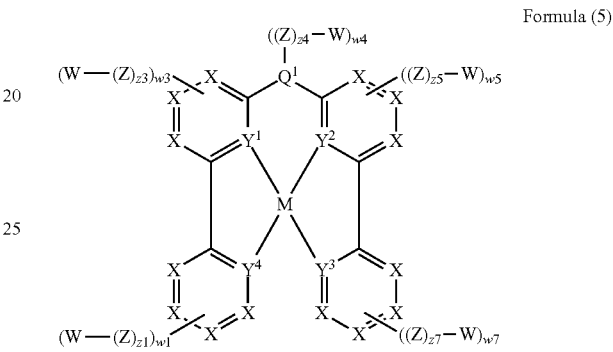

Formula (5)

wherein the indices and symbols are defined as above and wherein the sum of wi (i=1, 3, 4, 5 and 7) is 1 or 2, preferably 1.

Very particularly preferably, the present invention relates to a compound according to following Formula (6).

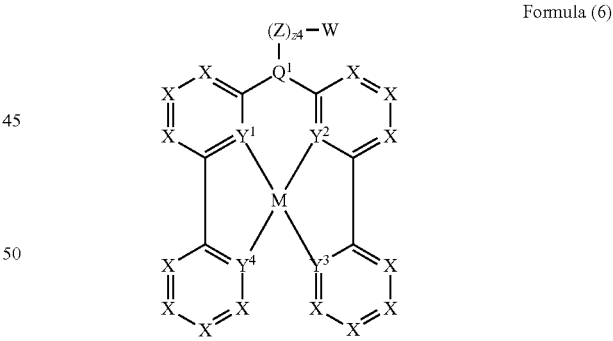

Formula (6)

wherein z4 is either 0 or 1.

Further preference is given to a compound of Formulae (1) to (6) wherein $Q^1$=N. Particular preference is given to a compound of Formulae (1) to (6) wherein $Q^1$=N and M=Pt. Even more preference is given to a compound of Formulae (1) to (6) wherein $Q^1$=N, M=Pt, $Y^1$=$Y^2$=C and $Y^3$=$Y^4$=N.

Yet another particularly preferred embodiment relates to the following compound having the general Formulae (7).

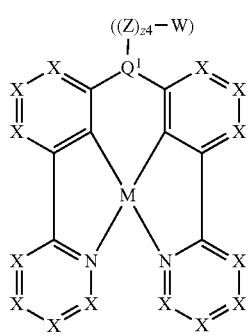

Formula (7)

wherein the symbols and indices are defined as above and wherein z4 is either 0 or 1. Preferably, $Q^1$=N in Formula (7). Particularly preferably $Q^1$=N and M=Pt in compound of Formula (7).

Yet another preferred embodiment of the present invention is a compound of Formulae (3) to (8), wherein X is $CR^1$.

Thus, the following compound having the general Formula (9) is also subject of the present invention.

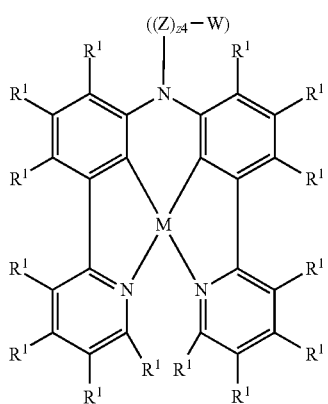

Formula (9)

wherein the symbols are defined as above, z4 is either 0 or 1 and M is defined as above, preferably M=Pt.

Preferably, the compound according to Formula (1) has the following general Formula (10), wherein M=Pt is further preferred.

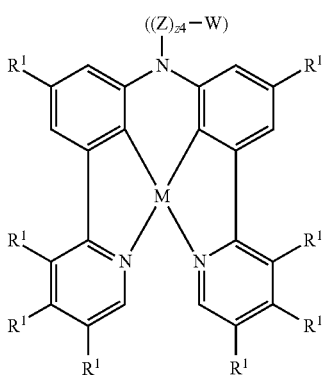

Formula (10)

Particularly preferably, the compound according to Formula (1) has the following general Formula (11), wherein M=Pt is further preferred.

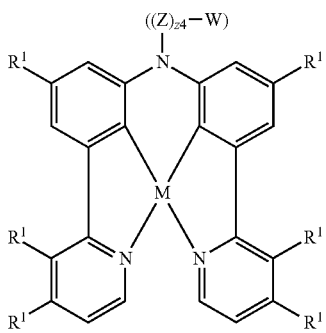

Formula (11)

Very particularly preferably, the compound according to Formula (1) has the following general Formula (12), wherein M=Pt is further preferred.

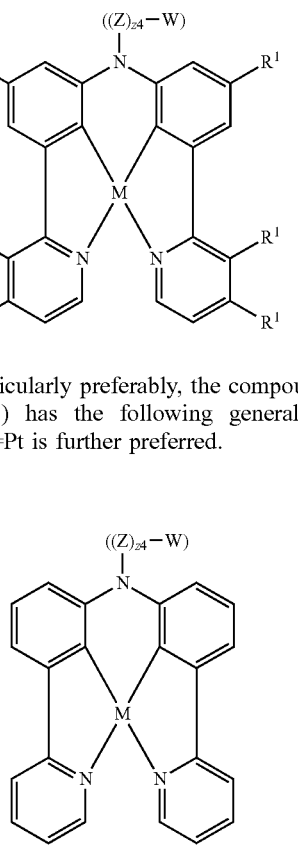

Formula (12)

It is further preferred that Z in Formulae (1) and (3) to (12) is selected from one of the following Formulae (13) to (15), preferably from Formulae (13) or (14), particularly preferably from Formula (13).

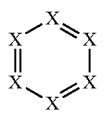

Formula (13)

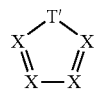

Formula (14)

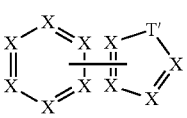

Formula (15)

wherein X is defined as above and T' is S or O and wherein $R^1$ is defined as above. Hereby, Z links the two other molecular components, i.e. W and the core bearing the metal M, in any possible position.

Preferably Z is selected from one of the following Formulae (16) to (51), particularly preferably from Formulae (16) to (29), very particularly preferably from Formulae (16)

to (25) wherein # and * denote the positions to which W and the metal M-bearing core bind, and wherein $R^1$ is defined as above.
Formula (16)
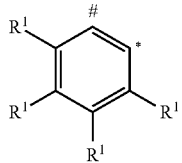
Formula (17)
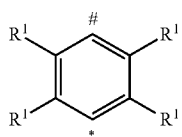
Formula (18)
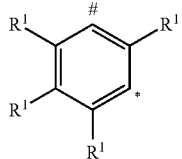
Formula (19)
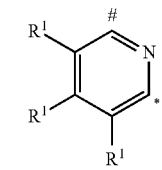
Formula (20)
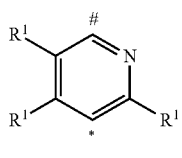
Formula (21)
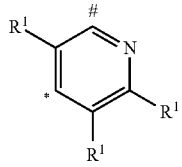
Formula (22)
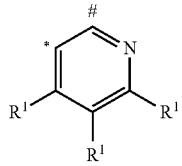
Formula (23)
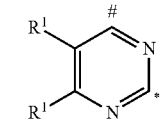
-continued
Formula (24)
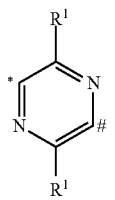
Formula (25)
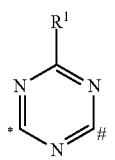
Formula (26)
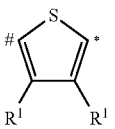
Formula (27)
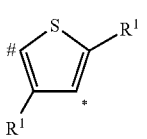
Formula (28)
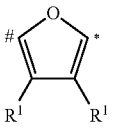
Formula (29)
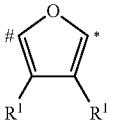
Formula (30)
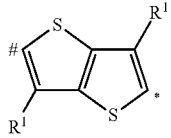
Formula (31)
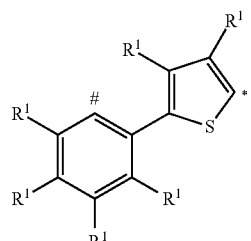
Formula (32)
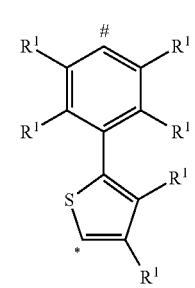

-continued
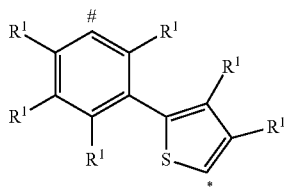
Formula (33)
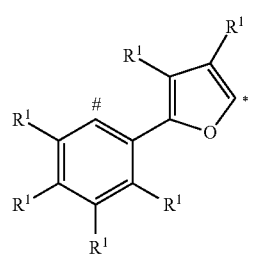
Formula (34)
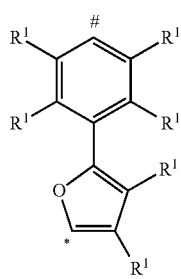
Formula (35)
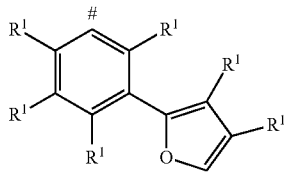
Formula (36)
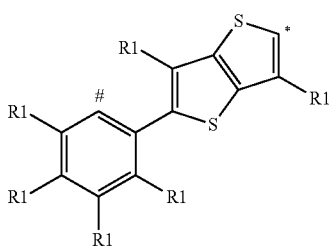
Formula (37)
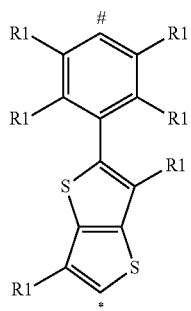
Formula (38)
-continued
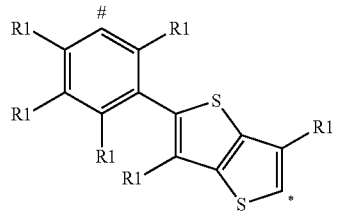
Formula (39)
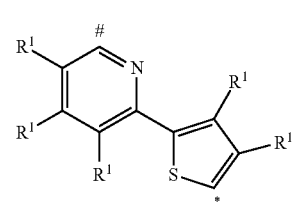
Formula (40)
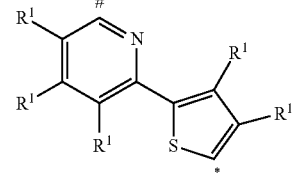
Formula (41)
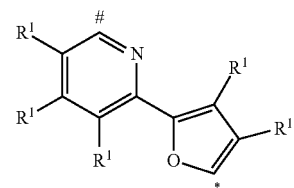
Formula (42)
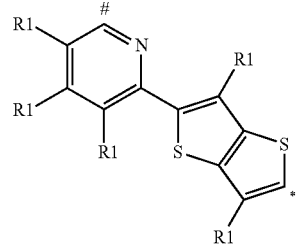
Formula (43)
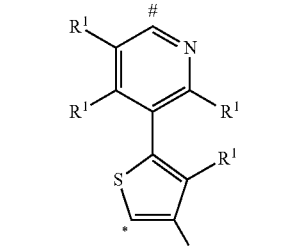
Formula (44)
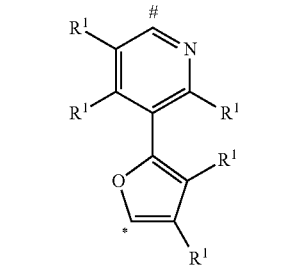

Formula (45)

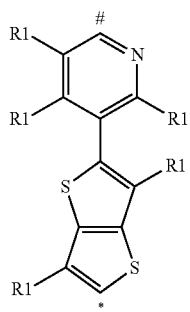

Formula (46)

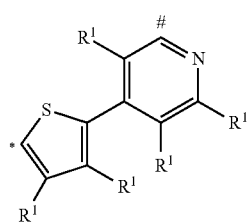

Formula (47)

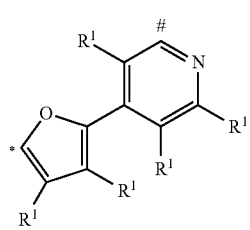

Formula (48)

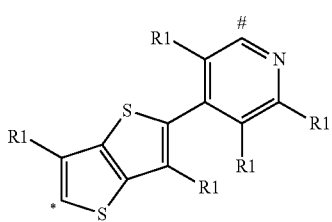

Formula (49)

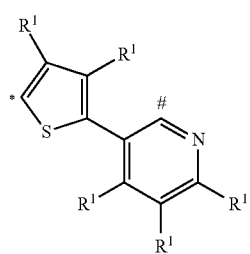

Formula (50)

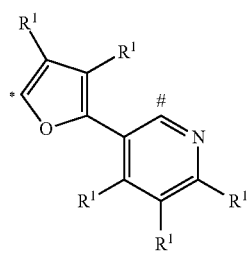

Formula (51)

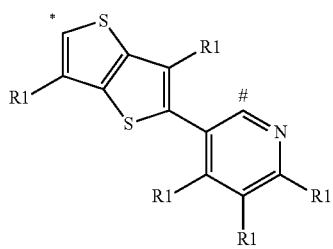

Particularly preferably, # denotes the position which binds to the metal M-bearing core and * denotes the position which binds to W. Very particularly preferably, # denotes the position which binds to the metal M-bearing core and * denotes the position which binds to W and $R^1$ is H.

In another preferred embodiment Z is selected from Formulae (16), (17), or (18), further preferred are Formulae (17) and (18).

In another preferred embodiment according to the present invention z4 is 0, i.e., the metal M-bearing core is directly bonded to W, i.e. W is directly bonded to $Q^1$.

The present invention relates in a preferred embodiment to a compound of Formulae (1) and (2) to (12) wherein r in Formula (2) is 0. In this case W has the following general Formula (52).

Formula (52)

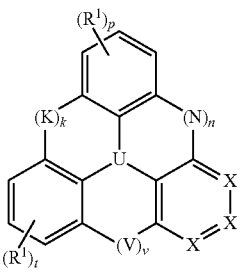

wherein the indices and symbols are defined as above and wherein p is 0, 1, 2 or 3.

Particularly preferred are the following chemical structures for W.

Formula (53)

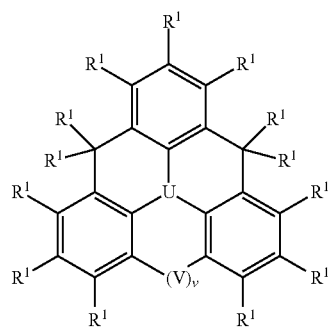

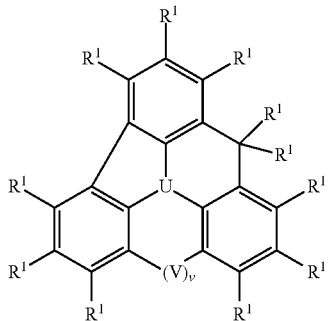

Formula (54)

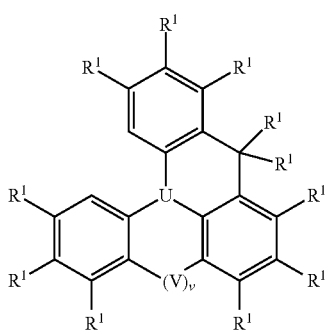

Formula (55)

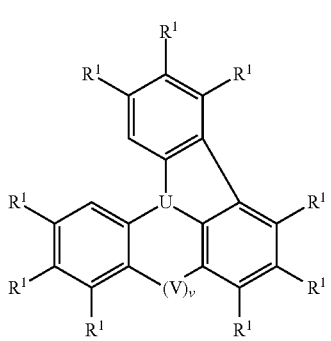

Formula (56)

According to the present invention it is preferred if U in W Formulae (2) and (52) to (56)) is nitrogen.

The following general Formulae (57) to (61) define preferred positions in W, denoted by ##, which are bonded either to Z or to the metal M-bearing core of compound of Formula (1).

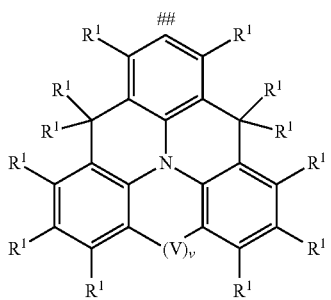

Formula (57)

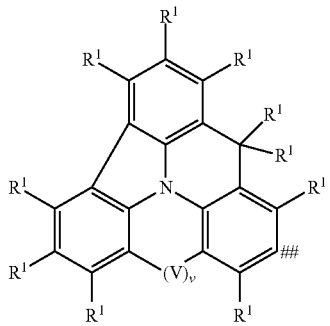

Formula (58)

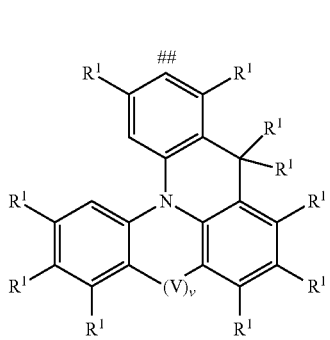

Formula (59)

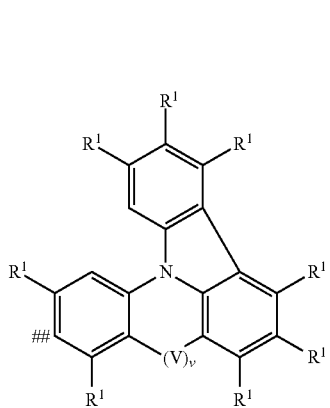

Formula (60)

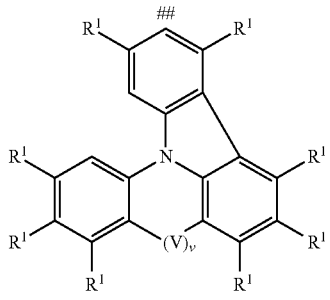

Formula (61)

Some selected particularly preferred rests W are listed in the following table.

Formula (62)

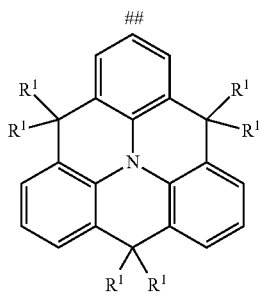

Formula (63)

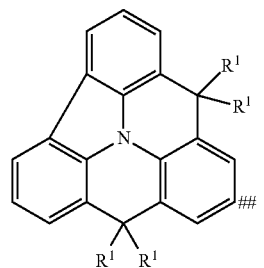

Formula (64)

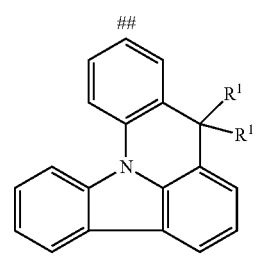

Formula (65)

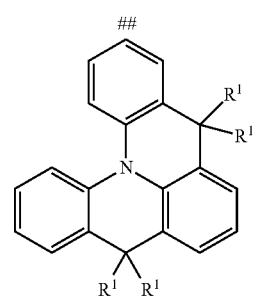

Formula (66)

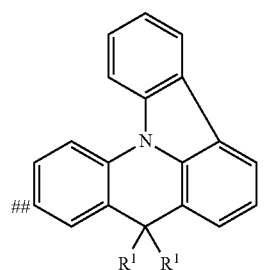

Formula (67)

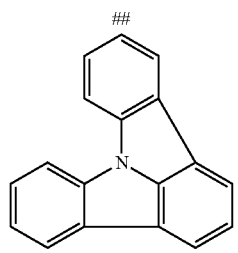

Formula (68)

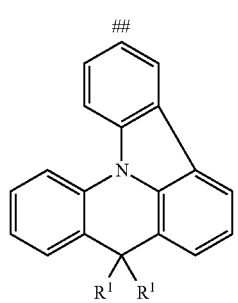

It is further preferred that $R^1$ in Formulae (52) to (68) is, identically or differently on each occurrence, selected from H, D, F, a straight-chain alkyl having 1 to 40 C-atoms or a straight-chain alkenyl or alkynyl group having 2 to 40 C atoms, each of which may be substituted with one or more $R^2$, which is as defined above.

In a particularly preferred embodiment the present invention relates to a compound of Formula (1) with W according to Formula (2), wherein m=0, k, n=1 and r=1 or 2 and s=0. Thus, a W having the general Formula (69) is particularly preferred Formula (69)

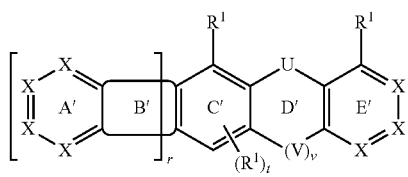

Formula (73a)

wherein r=1 or 2, and wherein the remaining indices and symbols are defined as above. W is bonded to Z or to the metal M-bearing core via any possible position in W.

Preferably the binding of W to either Z or the metal M-bearing core occurs via one of two positions as indicated by ## the Formula (70). If binding occurs via U in ring D' then U=NR$^1$ and $R^1$ is replaced by the bond. If binding occurs via X in ring E' then X=CR$^1$ and $R^1$ is replaced by the bond.

Formula (70)

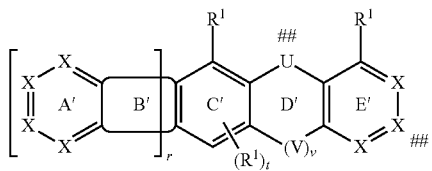

Further preference is given to W having the following Formula (71), wherein if binding occurs via ring E' then $R^1$ is replaced by a single bond.

Formula (71)

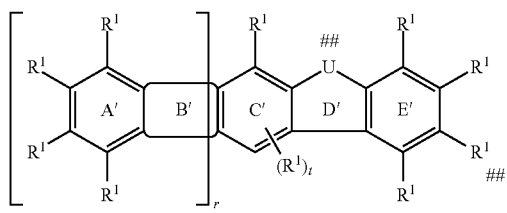

Particular preference is given to a compound according to Formula (1) with W according to Formulae (2), (69), (70) or (71) wherein U is either $NR^1$ or O, preferably $NR^1$.

If W binds to either Z or to the metal M-bearing core via U in ring D' then the following Formulae (72) to (77) represent very particularly preferred embodiments for W.

Formula (72)

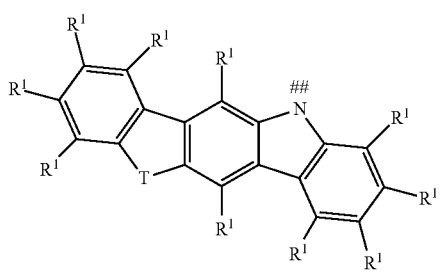

Formula (73)

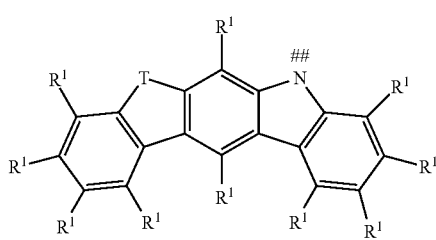

Formula (74)

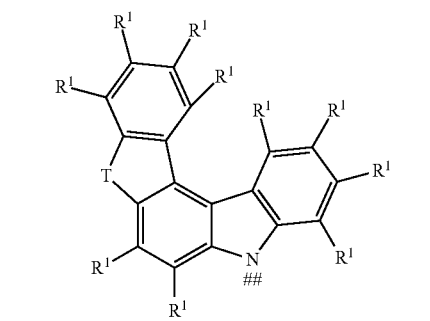

Formula (75)

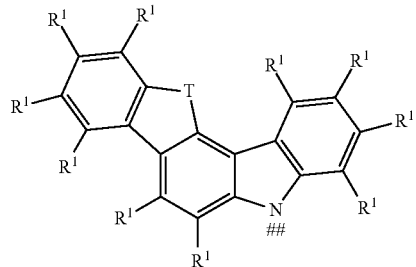

Formula (76)

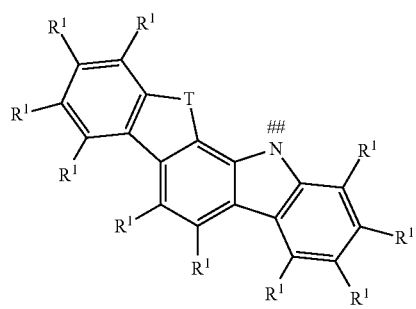

Formula (77)

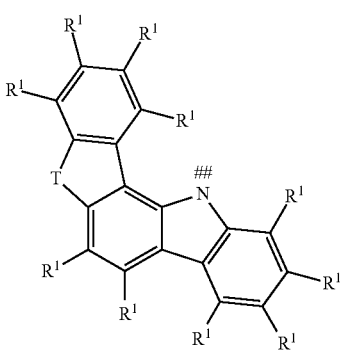

If W binds to either Z or to the metal M-bearing core via ring E' then the following Formulae (72) to (77) represent very particularly preferred embodiments for W.

Formula (78)

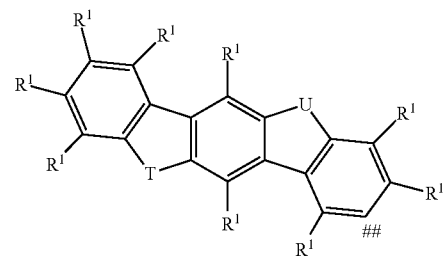

Formula (79)

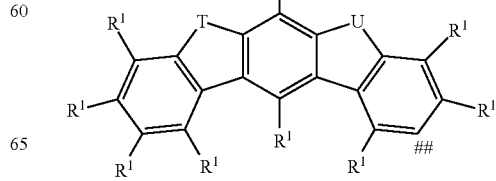

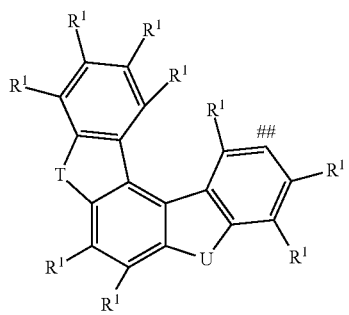

Formula (80)

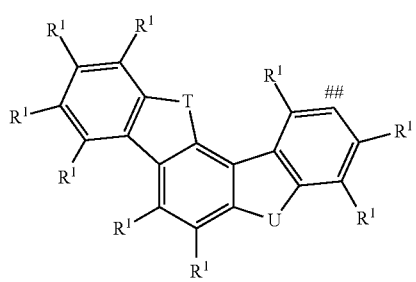

Formula (81)

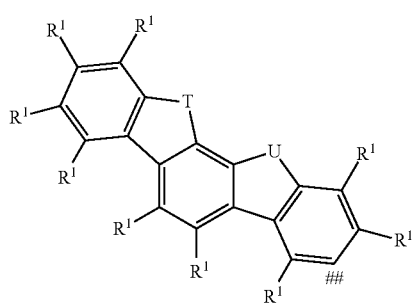

Formula (82)

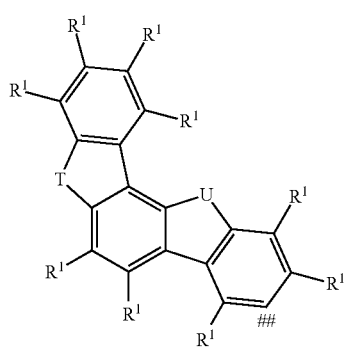

Formula (83)

It is further preferred that T and U in Formulae (69) to (83) are independently selected from $C(R^1)_2$, $NR^1$ or O, particularly preferably $C(R^1)_2$, $NR^1$ and very particularly preferably $NR^1$.

It is also preferred that U and T in Formulae (78) to (83) are independently selected from $C(R^1)_2$, $NR^1$ or O, particularly preferably $C(R^1)_2$, $NR^1$ and very particularly preferably $NR^1$.

Preferred substituents $R^1$ in the structures mentioned above are selected on each occurrence, identically or differently, from the group consisting of H, D, F, Br, $N(R^2)_2$, CN, $B(OR^2)_2$, $C(=O)R^2$, $P(=O)(R^2)_2$, a straight-chain alkyl group having 1 to 10 C atoms or a straight-chain alkenyl or alkynyl group having 2 to 10 C atoms or a branched or cyclic alkyl, alkenyl or alkynyl group having 3 to 10 C atoms, each of which may be substituted by one or more radicals $R^2$, where one or more H atoms may be replaced by F, or an aromatic or heteroaromatic ring system having 5 to 14 aromatic ring atoms, which may in each case be substituted by one or more radicals $R^2$; a plurality of radicals $R^1$ here may also form a mono- or polycyclic, aliphatic, aromatic and/or benzo-fused ring system with one another.

Particularly preferred radicals $R^1$ are selected on each occurrence, identically or differently, from the group consisting of H, F, Br, CN, $B(OR^2)_2$, a straight-chain alkyl group having 1 to 6 C atoms, in particular methyl, or a branched or cyclic alkyl group having 3 to 10 C atoms, in particular isopropyl or tert-butyl, where one or more H atoms may be replaced by F, or an aromatic or heteroaromatic ring system having 5 to 12 aromatic ring atoms, which may in each case be substituted by one or more radicals $R^2$; a plurality of radicals $R^1$ here may also form a mono- or polycyclic, aliphatic, aromatic and/or benzo-fused ring system with one another.

Very particularly preferably $R^1$ in the Formulae above is selected from the following Formulae (84) to (242h) wherein the rest can be, identically or differently from each other on each occurrence, substituted with one or more $R^2$, wherein $R^2$ is defined as above.

Formula (84)

Formula (85)

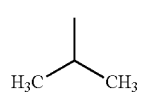

Formula (86)

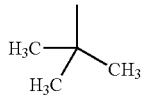

Formula (87)

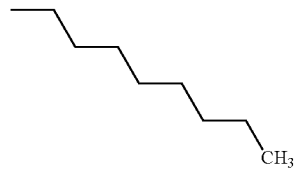

Formula (88)

Formula (89)

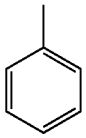

Formula (90)

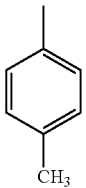

Formula (91)

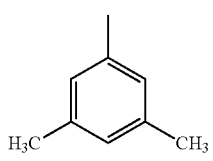
Formula (92)
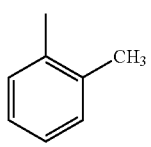
Formula (93)
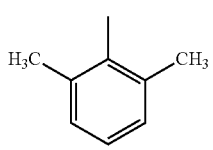
Formula (94)
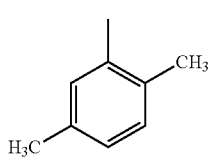
Formula (95)
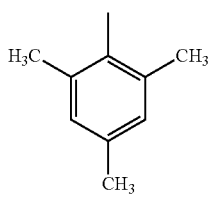
Formula (96)
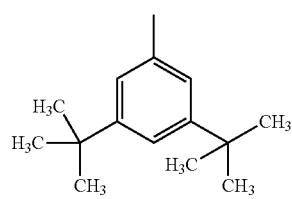
Formula (97)
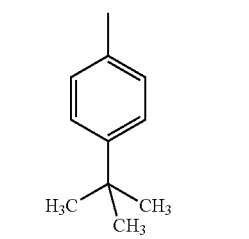
Formula (98)
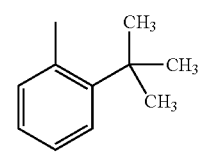
Formula (99)
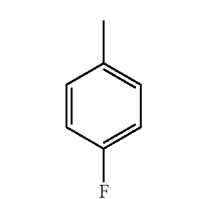
Formula (100)
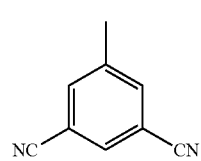
Formula (101)
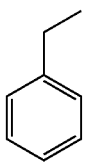
Formula (102)
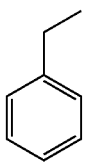
Formula (103)
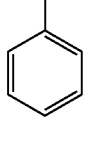
Formula (104)
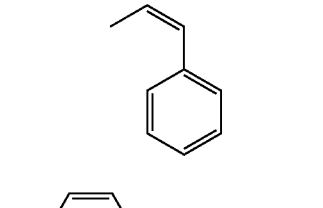
Formula (105)
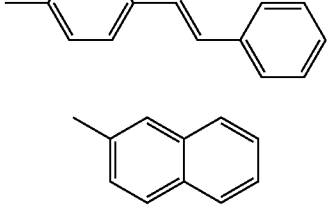
Formula (106)
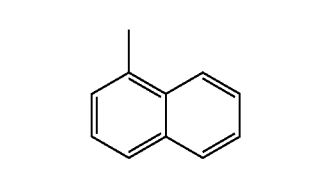
Formula (107)
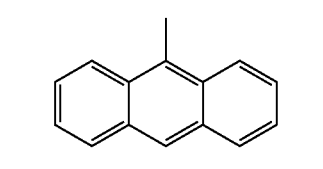
Formula (108)
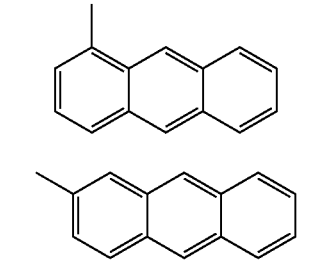
Formula (109)
Formula (110)

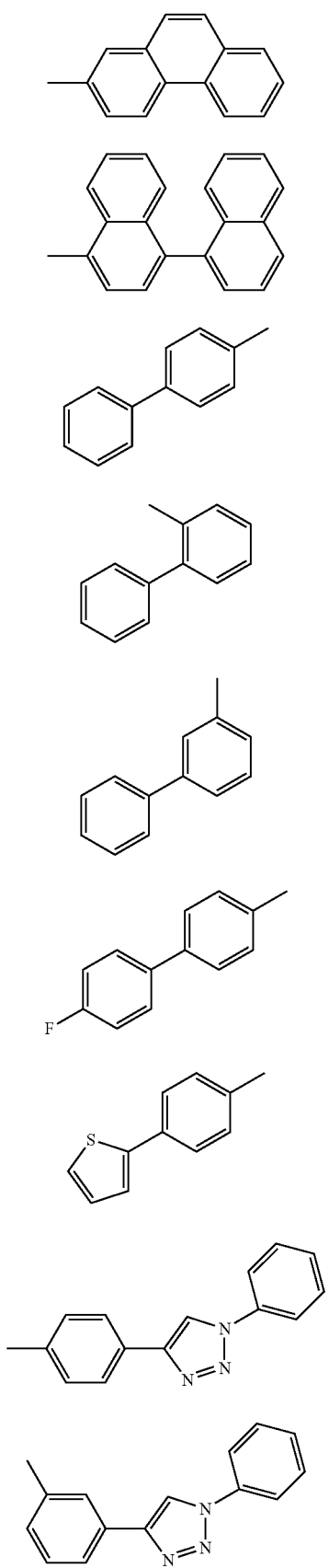

Formula (127)
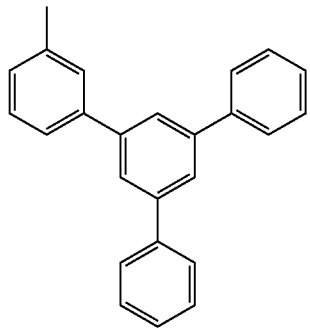
Formula (128)
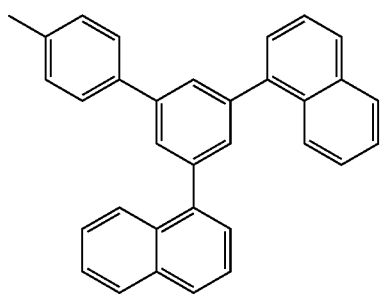
Formula (129)
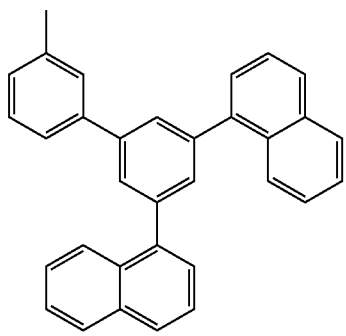
Formula (130)
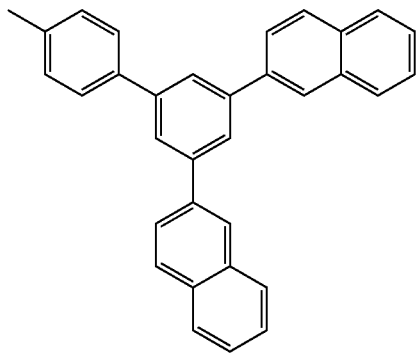
Formula (131)
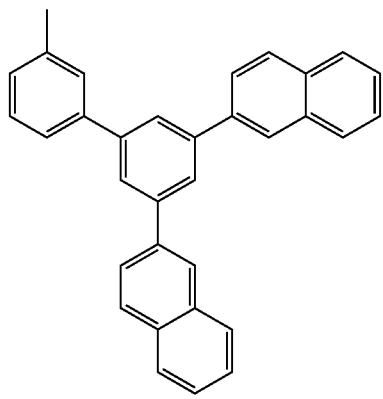
Formula (132)
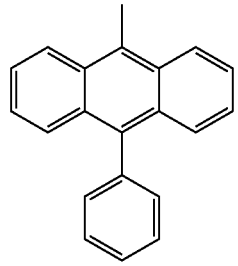
Formula (133)
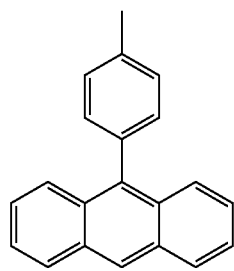
Formula (134)
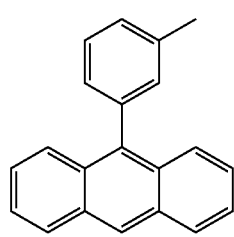
Formula (135)
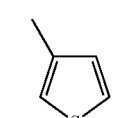
Formula (136)
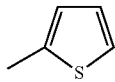
Formula (137)
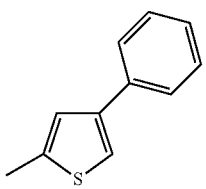

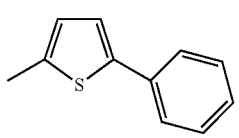
Formula (138)
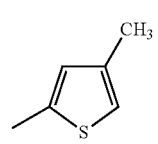
Formula (139)
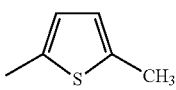
Formula (140)
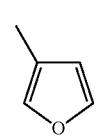
Formula (141)
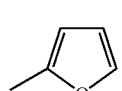
Formula (142)
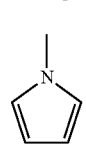
Formula (143)
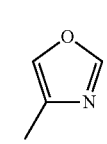
Formula (144)
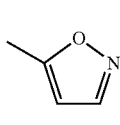
Formula (145)
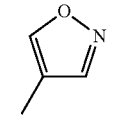
Formula (146)
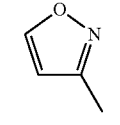
Formula (147)
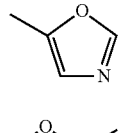
Formula (148)
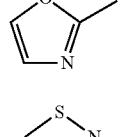
Formula (149)
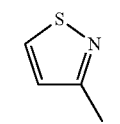
Formula (150)
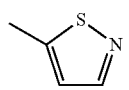
Formula (151)
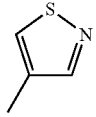
Formula (152)
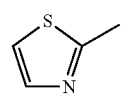
Formula (153)
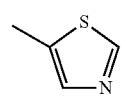
Formula (154)
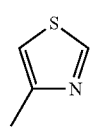
Formula (155)
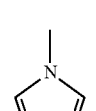
Formula (156)
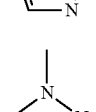
Formula (157)
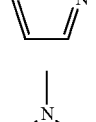
Formula (158)
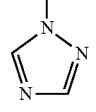
Formula (159)
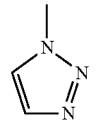
Formula (160)
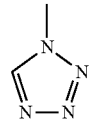
Formula (161)
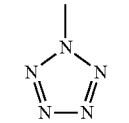
Formula (162)
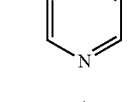
Formula (163)

-continued
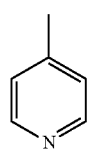
Formula (164)
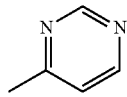
Formula (165)
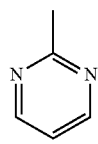
Formula (166)
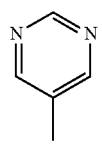
Formula (167)
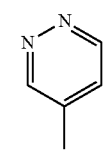
Formula (168)
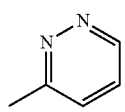
Formula (169)
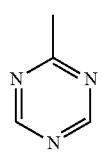
Formula (170)
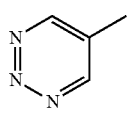
Formula (171)
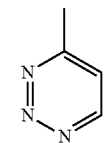
Formula (172)
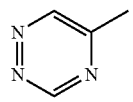
Formula (173)
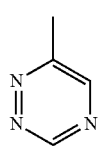
Formula (174)
-continued
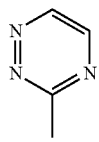
Formula (175)
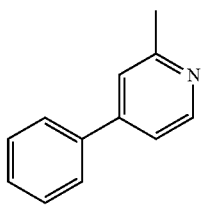
Formula (176)
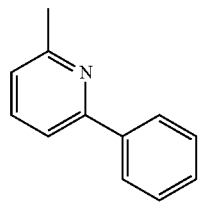
Formula (177)
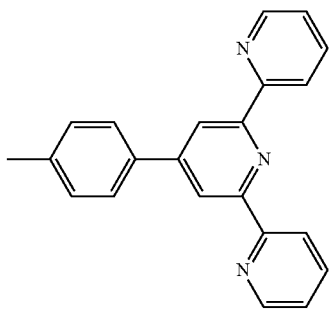
Formula (178)
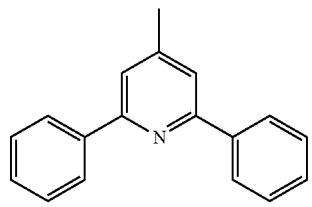
Formula (179)
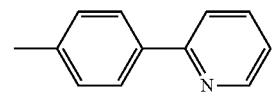
Formula (180)
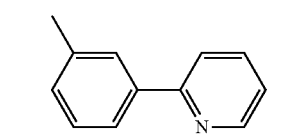
Formula (181)
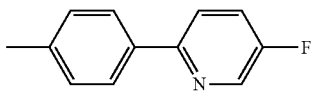
Formula (182)

Formula (183)
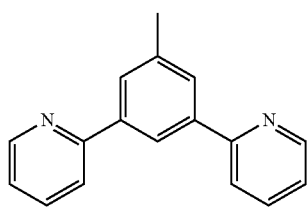
Formula (184)
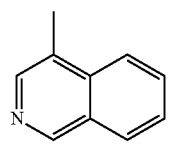
Formula (185)
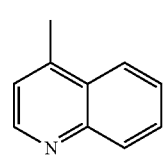
Formula (186)
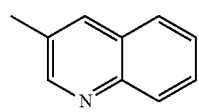
Formula (187)
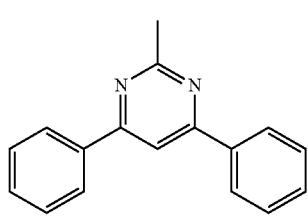
Formula (188)
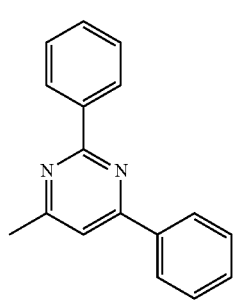
Formula (189)
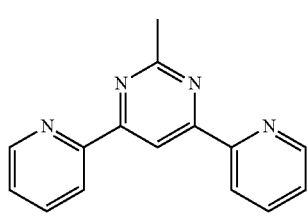
Formula (190)
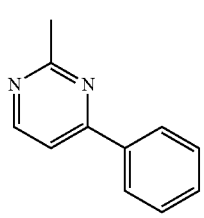
Formula (191)
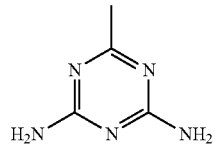
Formula (192)
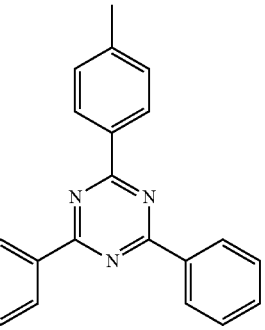
Formula (193)
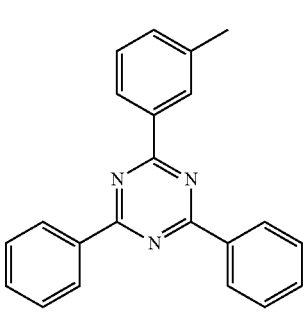
Formula (194)
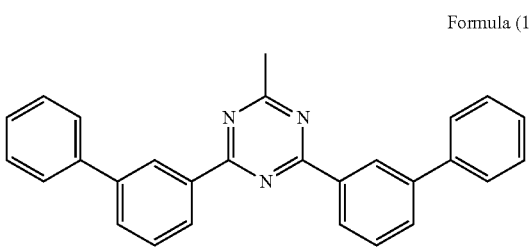
Formula (195)
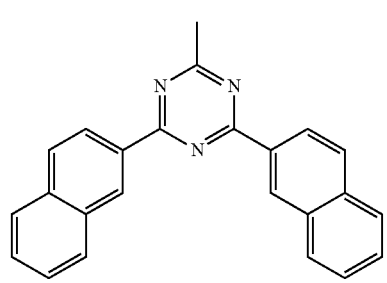
Formula (196)
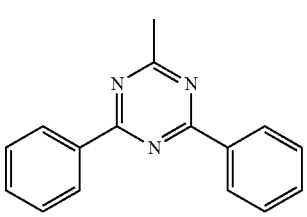

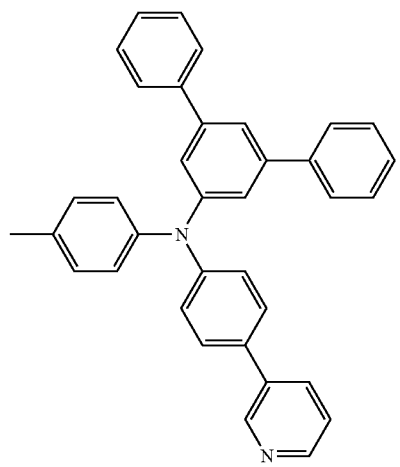

-continued
Formula (208)
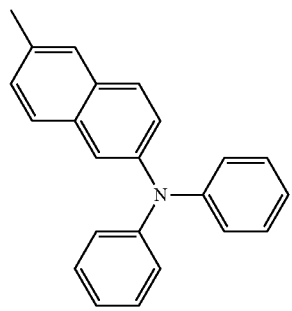
Formula (209)
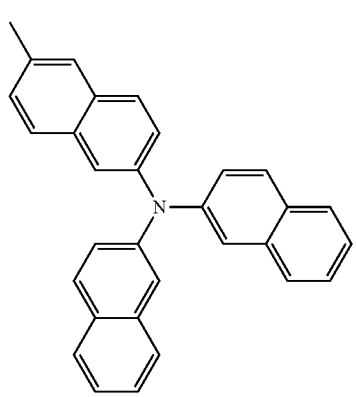
Formula (210)
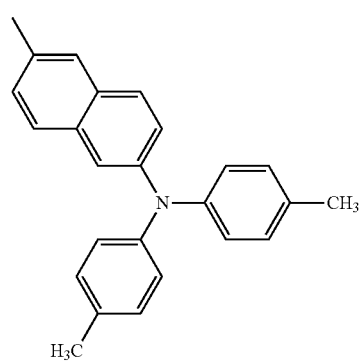
Formula (211)
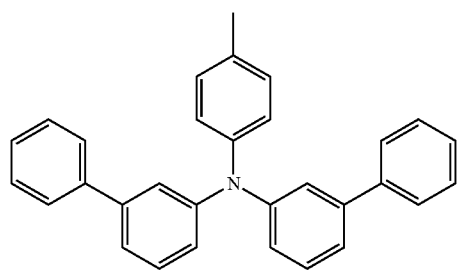
Formula (212)
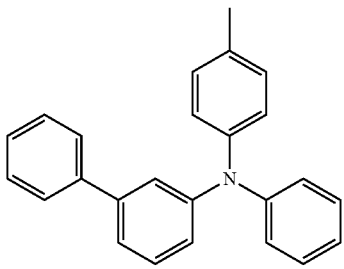
Formula (213)
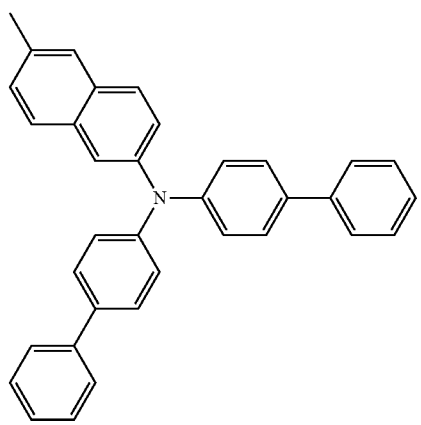
Formula (214)
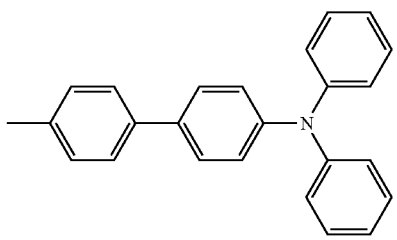
Formula (215)
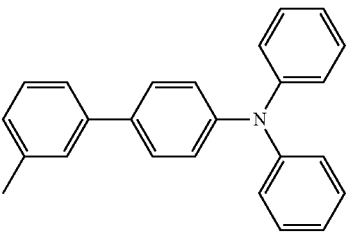
Formula (216)
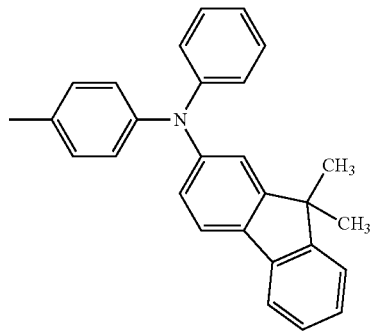

Formula (217)

Formula (218)

Formula (219)

Formula (220)

Formula (221)

Formula (222)

Formula (223)

Formula (224)

Formula (225)

Formula (226)

Formula (227)

Formula (228)

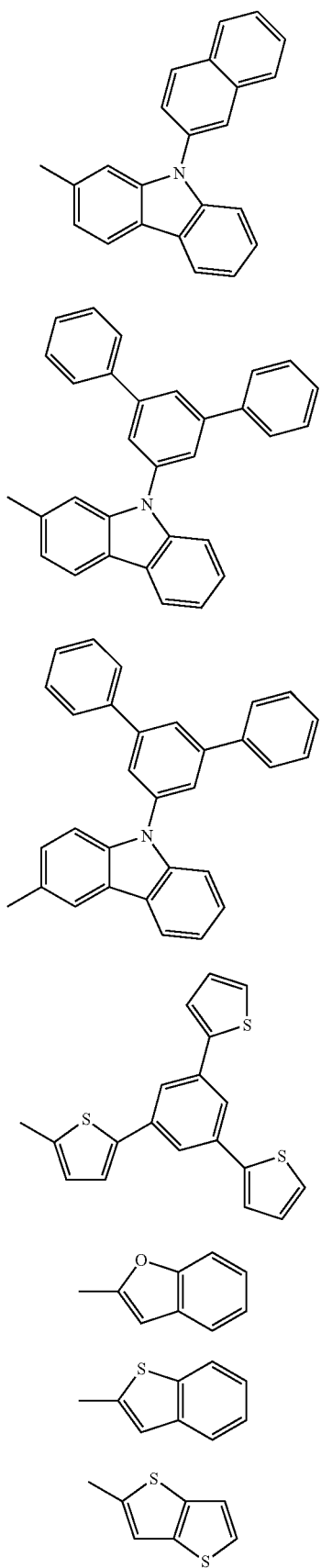
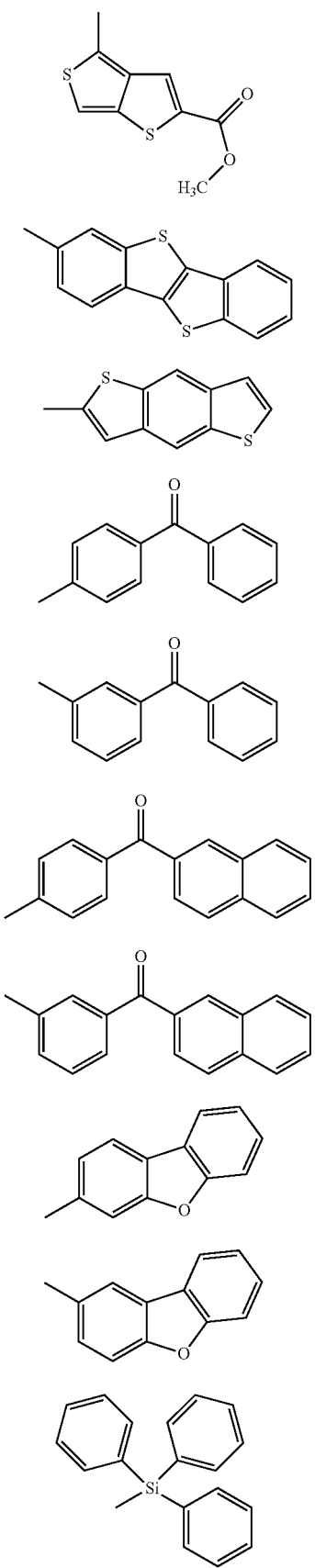
Formula (229)
Formula (230)
Formula (231)
Formula (232)
Formula (233)
Formula (234)
Formula (235)
Formula (236)
Formula (237)
Formula (238)
Formula (239)
Formula (240)
Formula (241)
Formula (242)
Formula (242a)
Formula (242b)
Formula (242c)

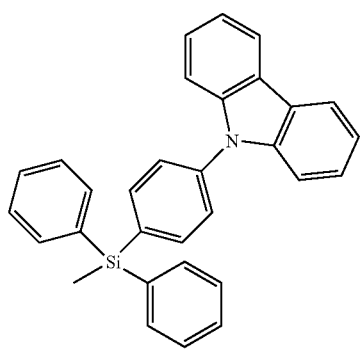

Formula (242d)

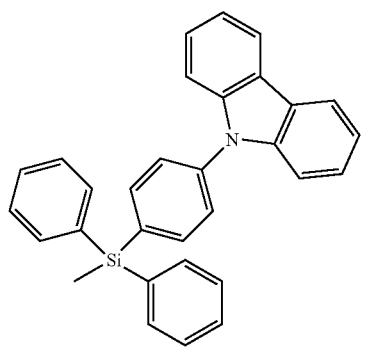

Formula (242e)

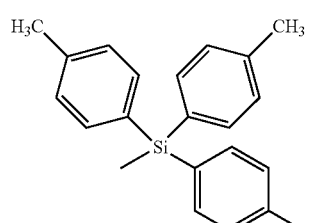

Formula (242f)

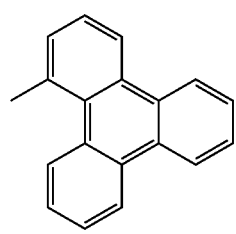

Formula (242g)

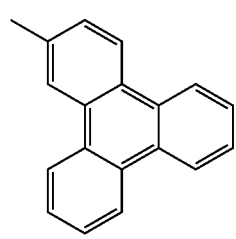

Formula (242h)

The straight line in the $R^1$ groups as shown in Formulae (84) to (242h) indicates the binding position.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily con-tain only aryl or heteroaryl groups, but instead in which, in addition, a plurality of aryl or heteroaryl groups may be interrupted by a non-aromatic unit (preferably less than 10% of the atoms other than H), such as, for exam-pie, an $sp^3$-hybridised C, N or O atom or a carbonyl group. Thus, for example, systems such as 9,9'-spirobifluorene, 9,9-diarylfluorene, triarylam-ine, diaryl ether, stilbene, etc., are also intended to be taken to mean aromatic ring systems for the purposes of this invention, and likewise systems in which two or more aryl groups are interrupted, for example, by a linear or cyclic alkyl group or by a silyl group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methyl-butyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethyl-hexyl, cyclooctyl, 1-bicyclo[2.2.2]octyl, 2-bicyclo[2.2.2]oc-tyl, 2-(2,6-dimethyl)octyl, 3-(3,7-dimethyl)octyl, trifluo-romethyl, pentafluoroethyl or 2,2,2-trifluoro-ethyl. An alkenyl group is taken to mean, for example, ethenyl, propenyl, butenyl, pentenyl, cyclopentenyl, hexenyl, cyclo-hexenyl, heptenyl, cyclo-heptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthra-cene, benzanthracene, phenanthrene, benzo-phenanthrene, pyrene, chrysene, perylene, fluoranthene, benzofluor-an-thene, naphthacene, pentacene, benzopyrene, biphenyl, biphenylene, terphenyl, terphenylene, fluorene, spirobifluo-rene, dihydrophenanthrene, dihydropyrene, tetrahydropy-rene, cis- or trans-indenofluorene, cis- or trans-monobenzo-indenofluorene, cis- or trans-dibenzoindenofluorene, truxene, isotruxene, spirotruxene, spiroisotruxene, furan, benzofuran, iso-benzofuran, dibenzofuran, thiophene, ben-zothiophene, isobenzothiophene, dibenzothiophene, pyrrole, indole, isoindole, carbazole, pyridine, quinoline, isoquino-line, acridine, phenanthridine, benzo-5,6-quinoline, benzo-6,7-quinoline, benzo-7,8-quinoline, phenothiazine, phenox-azine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothia-diazole.

The compounds of the Formula (1) may be electrically charged or un-charged. In a preferred embodiment, the compounds of the Formula (1) are electrically neutral. This is achieved in a simple manner in that the charges of the metal ion M is selected so that it compensates for the charge of the ligand.

The compound according to Formula (1) can be synthesized according to the following steps:

Step 1: Ligand Preparation 1

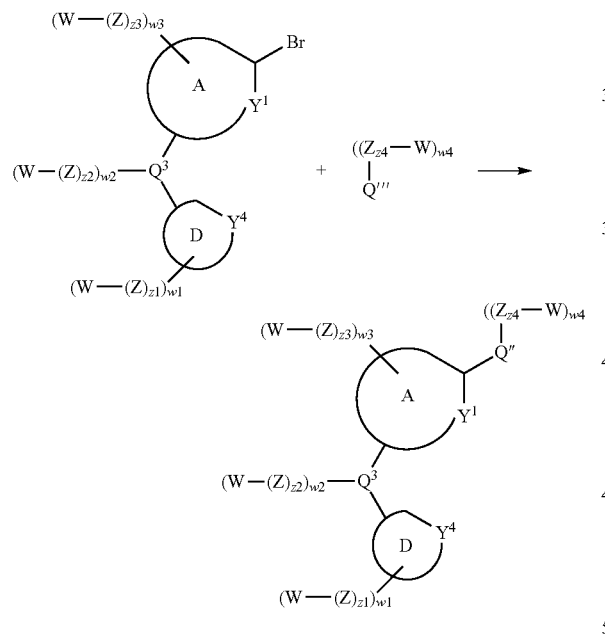

Step 2: Ligand Preparation 2

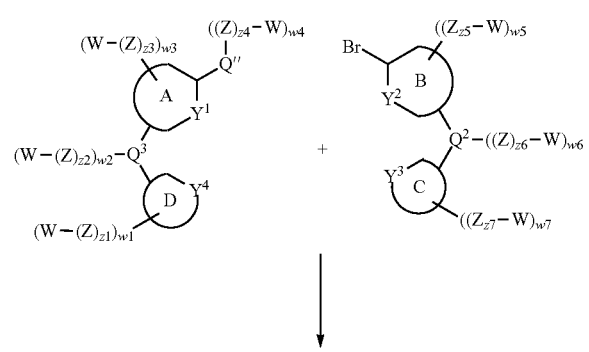

Step 3: Emitter Preparation

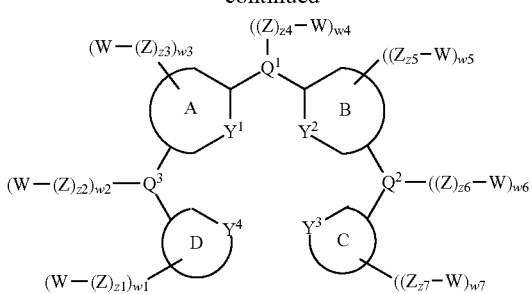

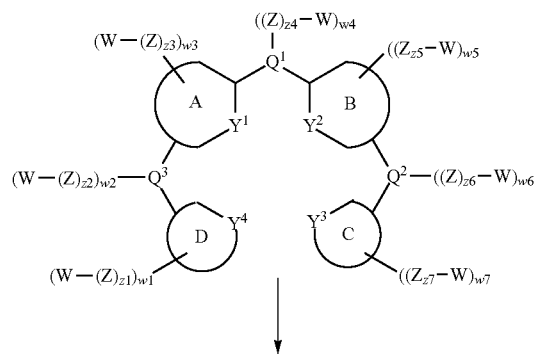

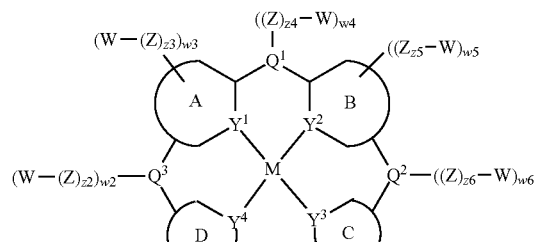

wherein Q''' is preferably $NH_2$. If Q''' is $NH_2$ then Q'' is NH and Q1 is N.

Thus the present invention also relates to a method for the preparation of a compound according to Formula (1). Preferably the compound according to Formula (1) is prepared according to the three steps as described above.

The synthetic methods explained here enable the preparation of, inter alia, the compounds of the Formulae (243) to (349) according to the invention depicted below.

Formula (243)
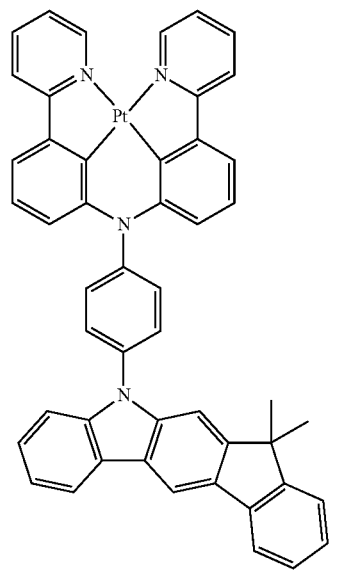
Formula (244)
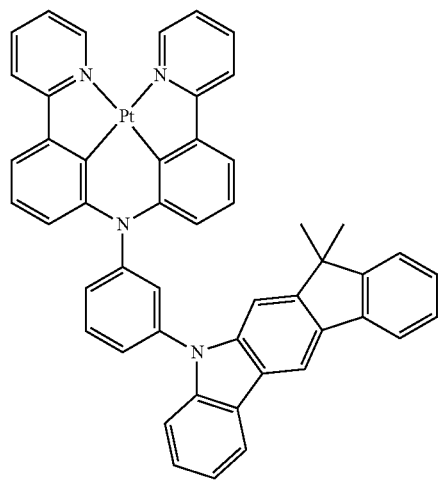
Formula (245)
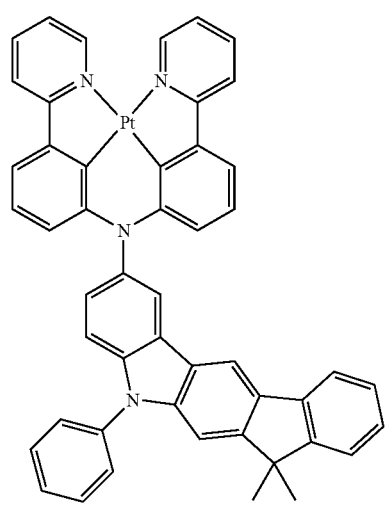
Formula (246)
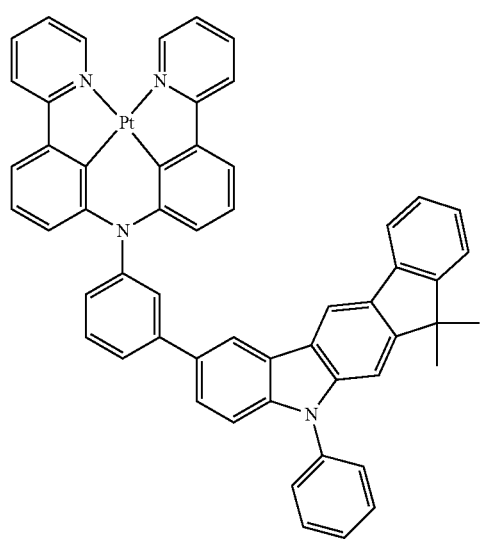

Formula (247)
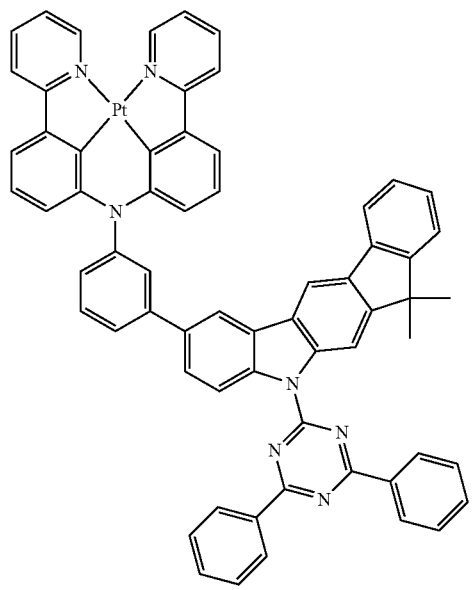
Formula (248)
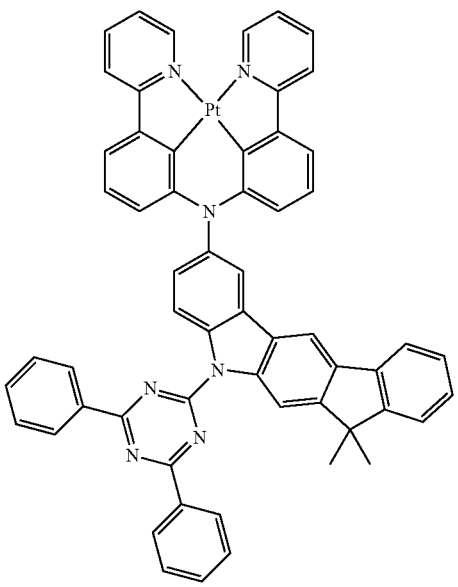
Formula (249)
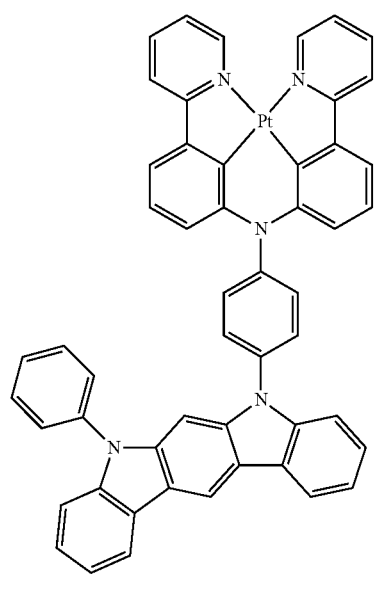
Formula (250)
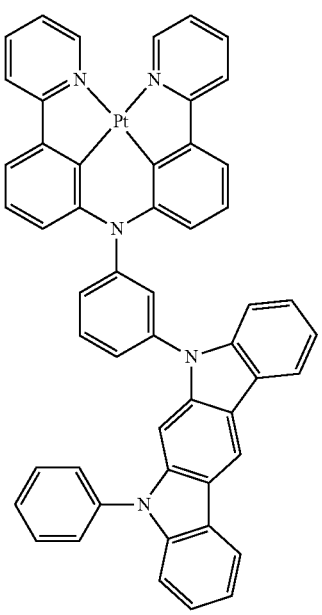

-continued
Formula (251)
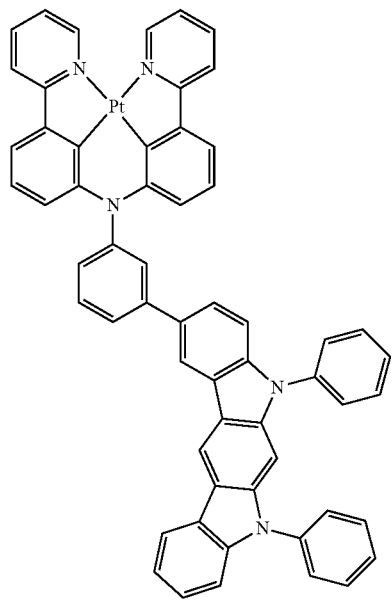
Formula (252)
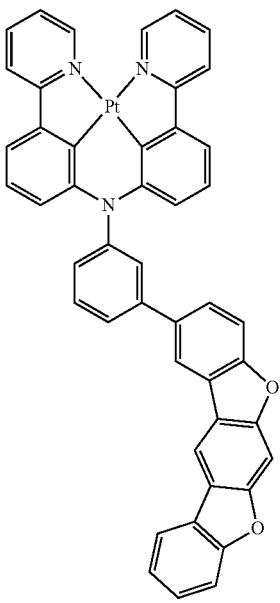
Formula (253)
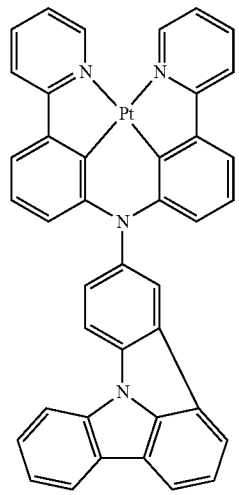
Formula (169)
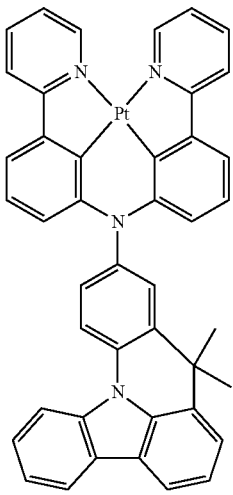
Formula (254)
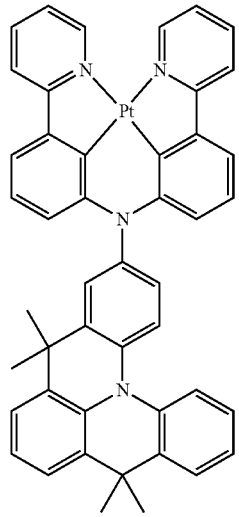
Formula (255)
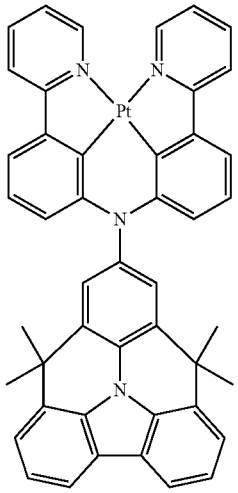

Formula (256)
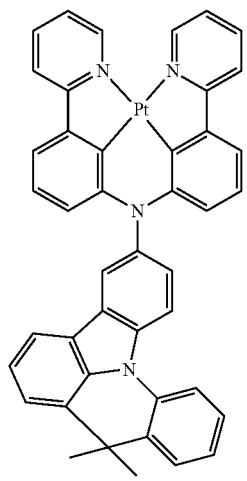
Formula (257)
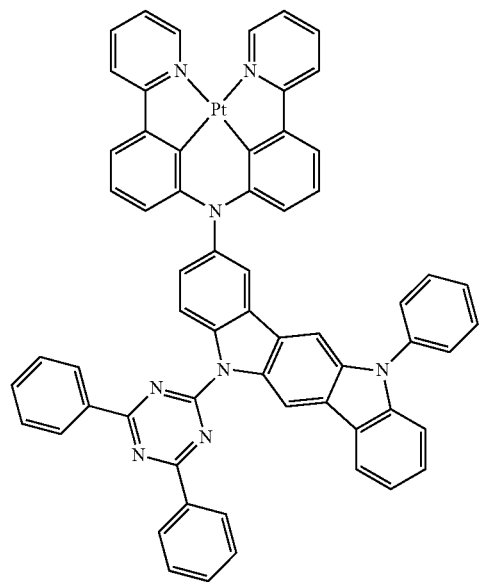
Formula (258)
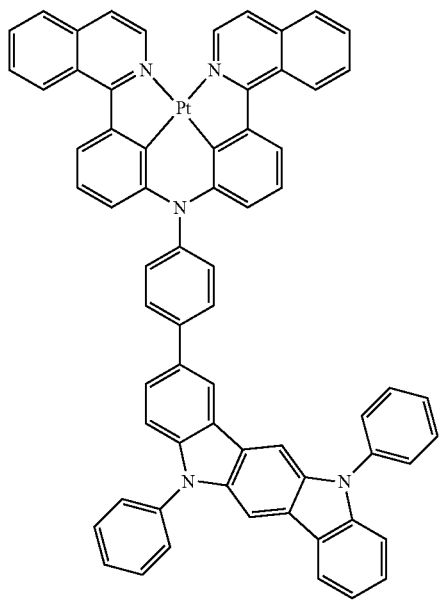
Formula (259)
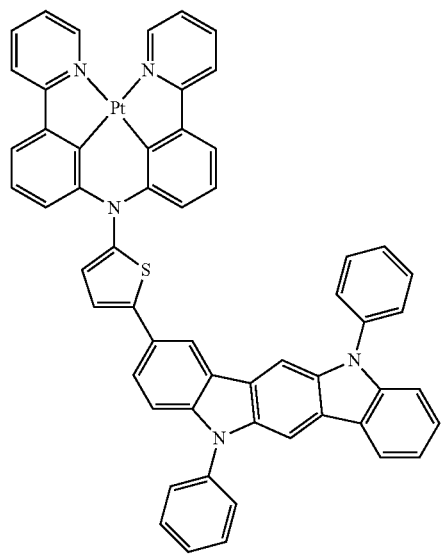

Formula (260)
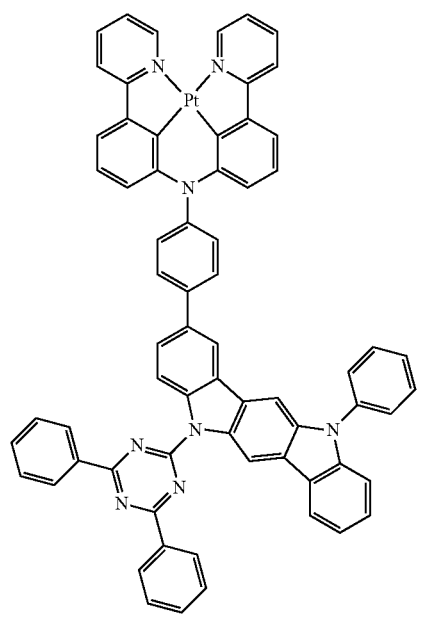
Formula (261)
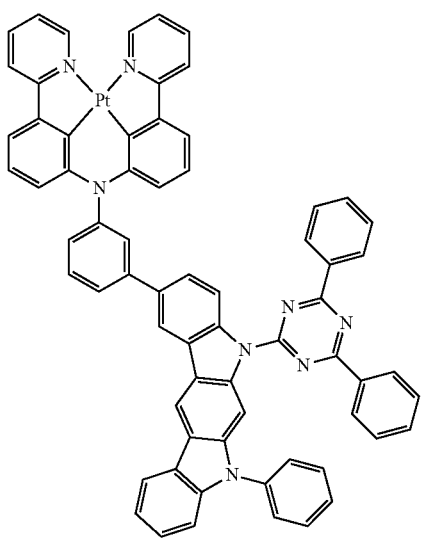
Formula (262)
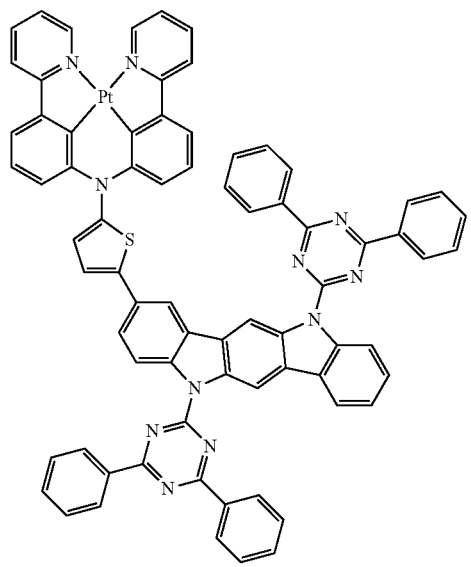
Formula (263)
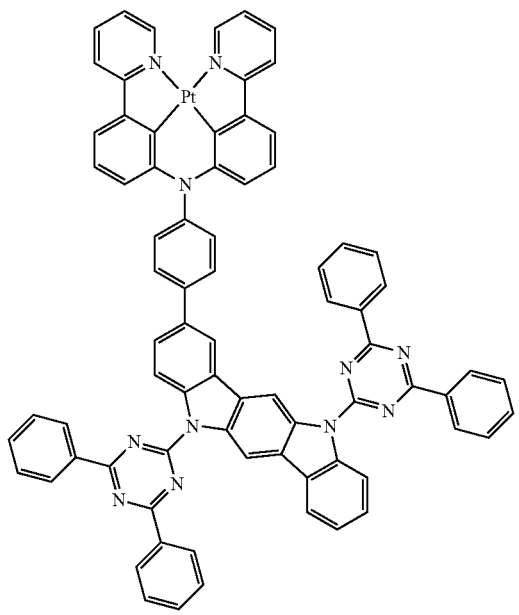

Formula (264)
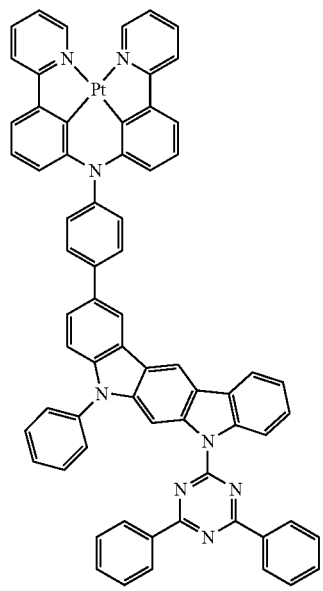
Formula (265)
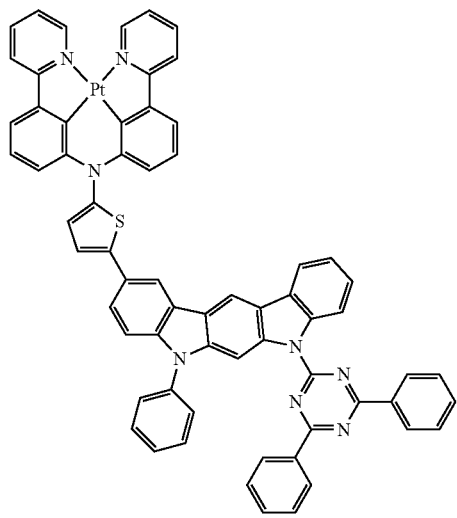
Formula (266)
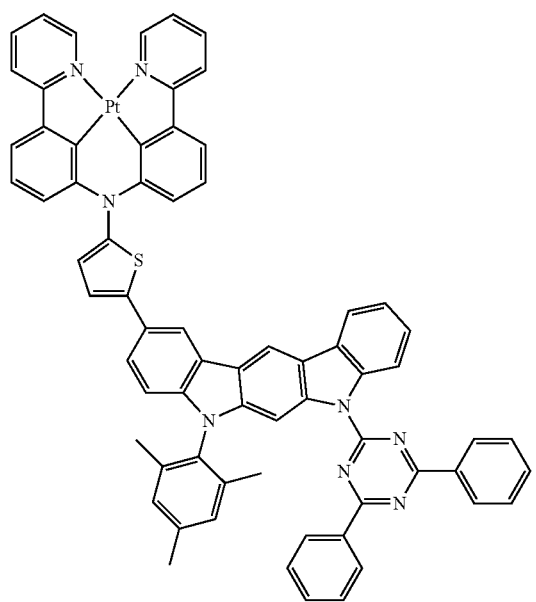
Formula (267)
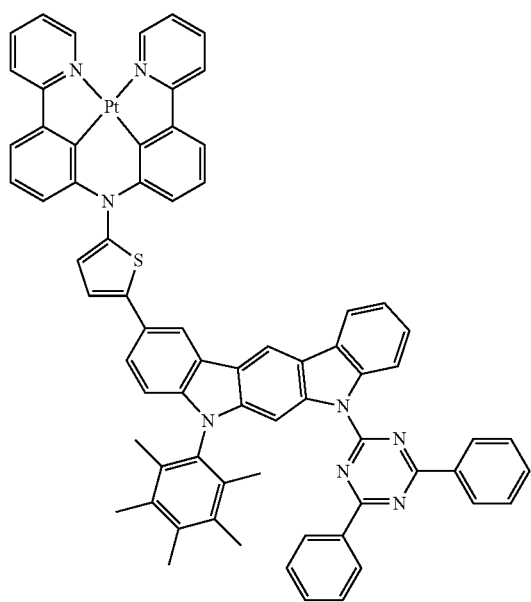

Formula (268)
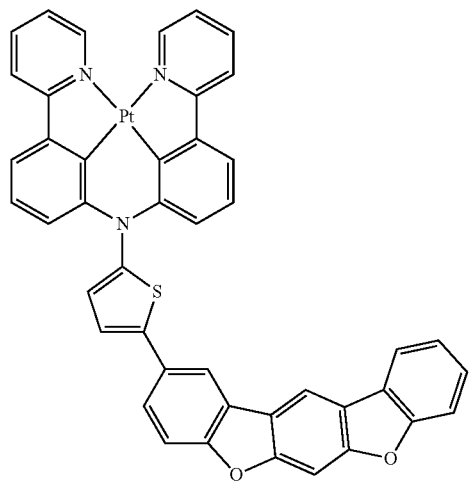
Formula (269)
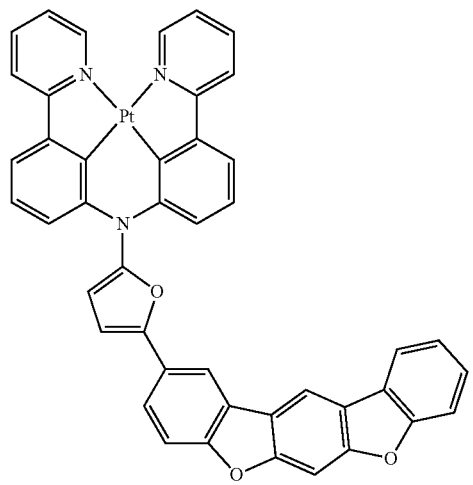
Formula (270)
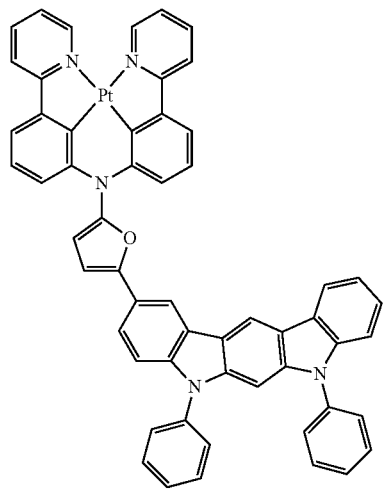
Formula (271)
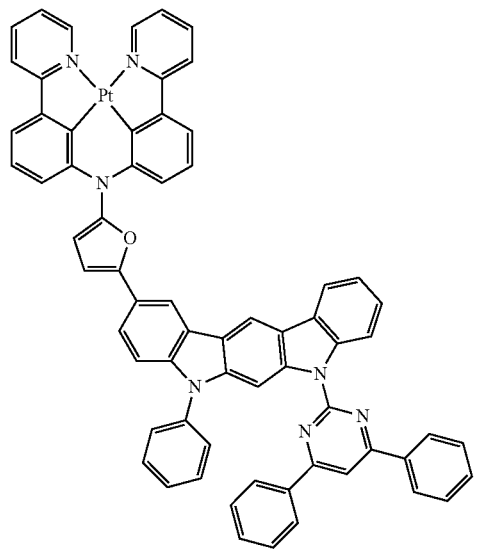

-continued
Formula (272)
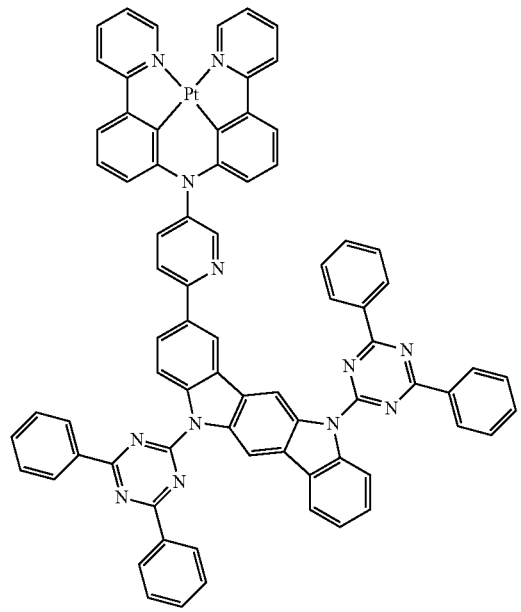
Formula (273)
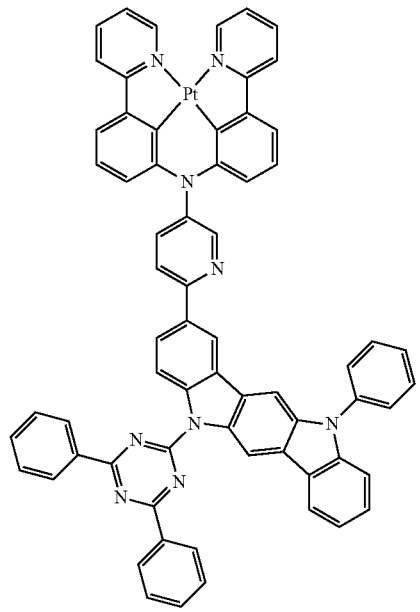
Formula (274)
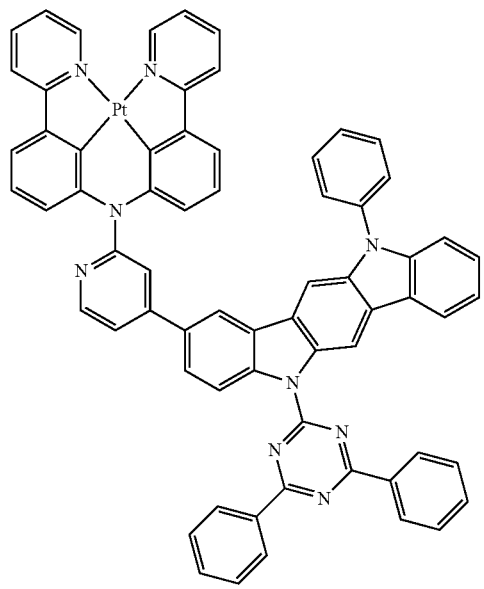
Formula (275)
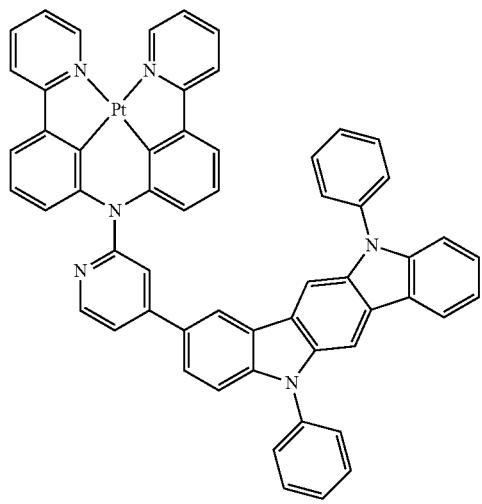

-continued
Formula (276)
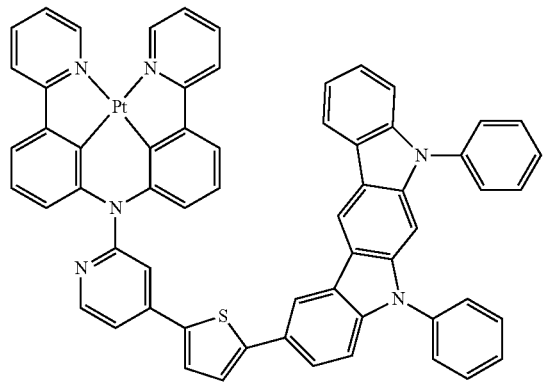
Formula (277)
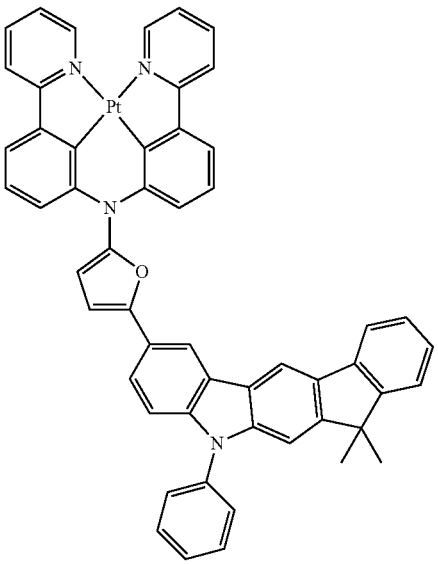
Formula (278)
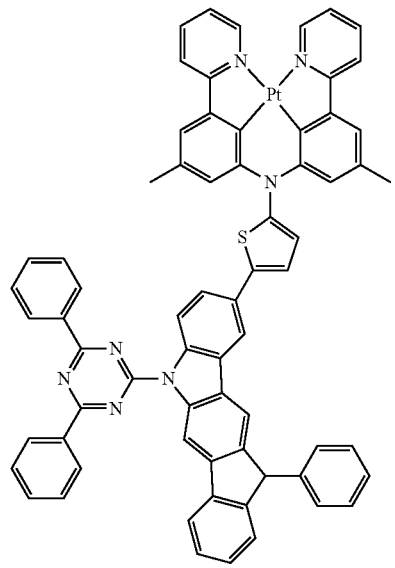
Formula (279)
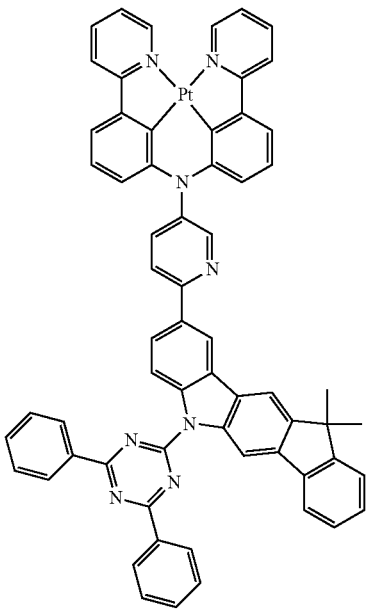
Formula (280)
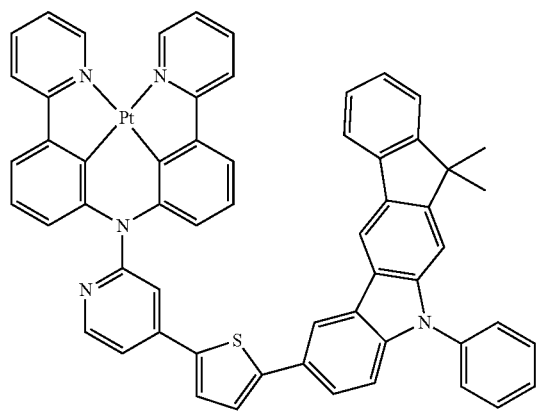
Formula (281)
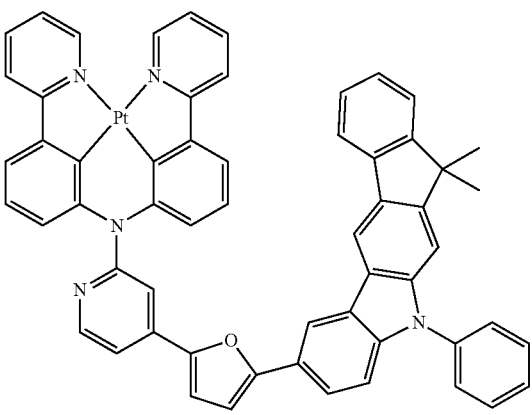

Formula (282)
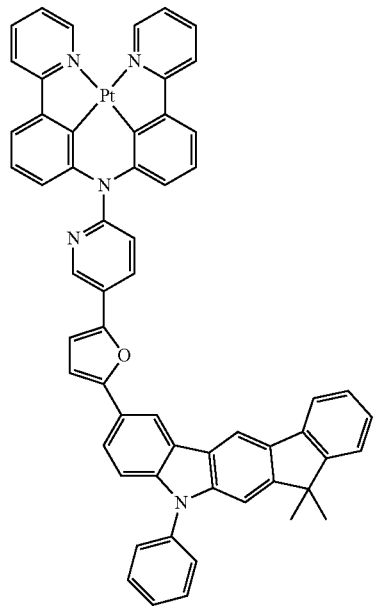
Formula (283)
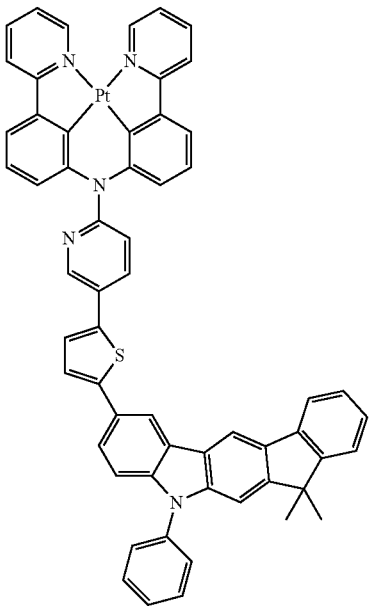
Formula (284)
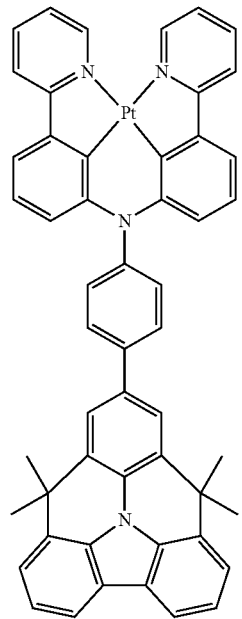
Formula (285)
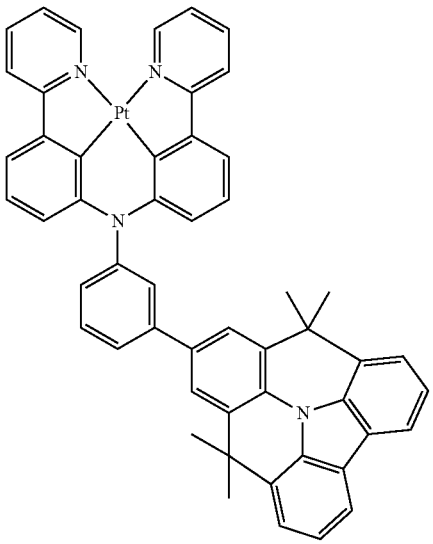

-continued
Formula (286)
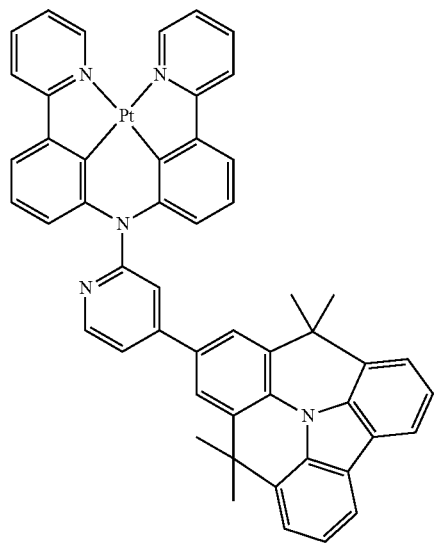
Formula (287)
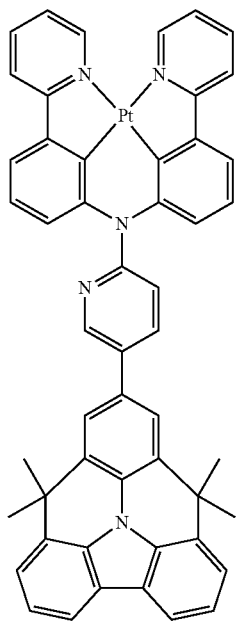
Formula (288)
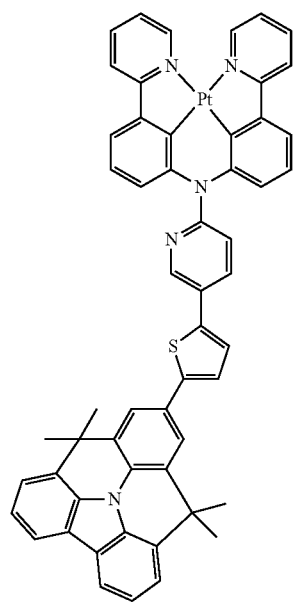
Formula (289)
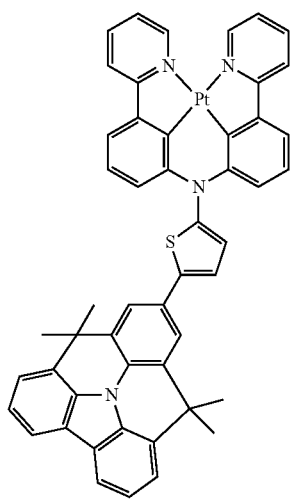

-continued
Formula (290)
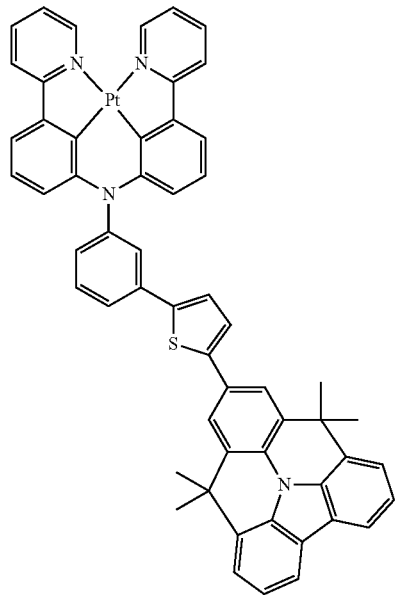
Formula (291)
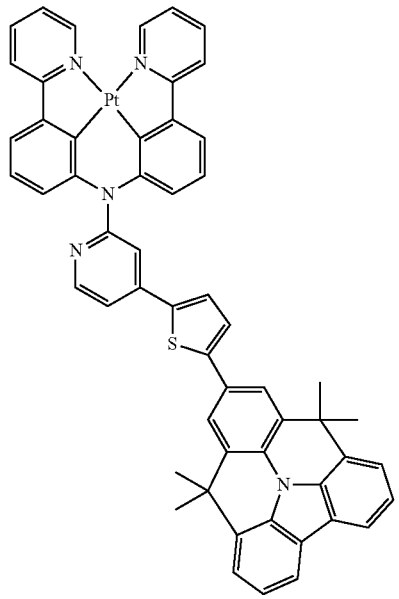
Formula (292)
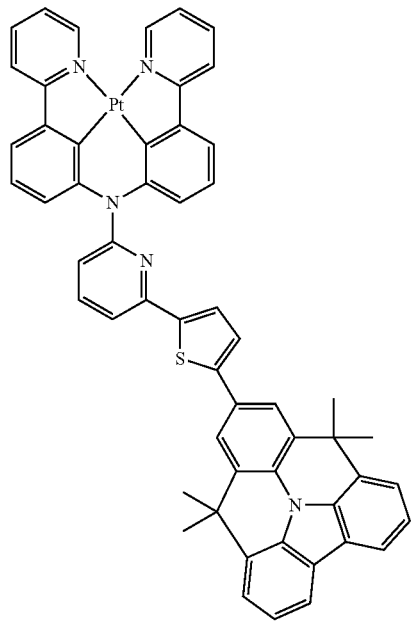
Formula (293)
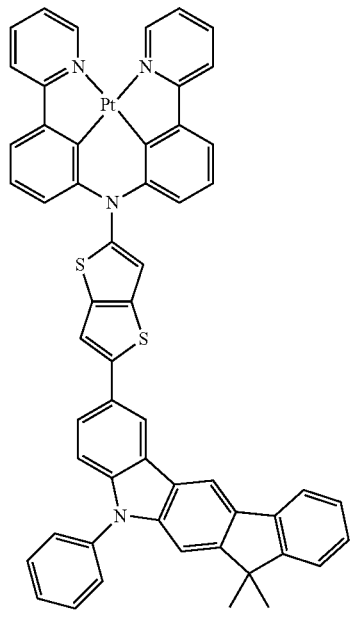

-continued
Formula (294)
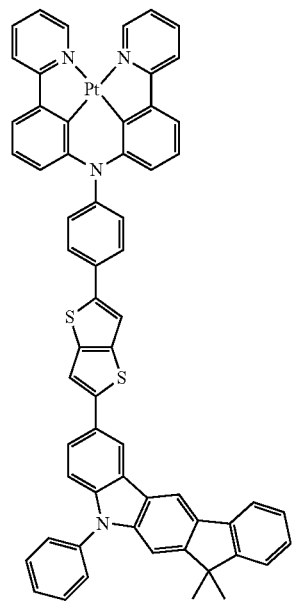
Formula (295)
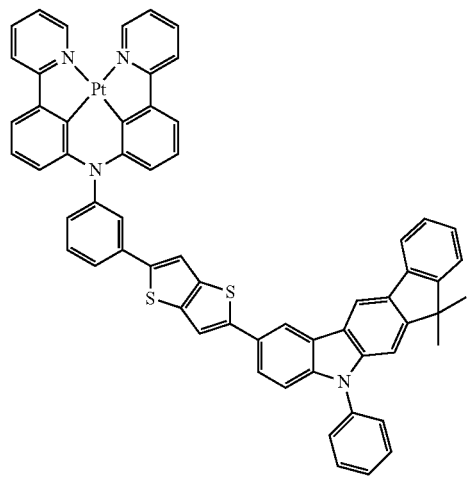
Formula (296)
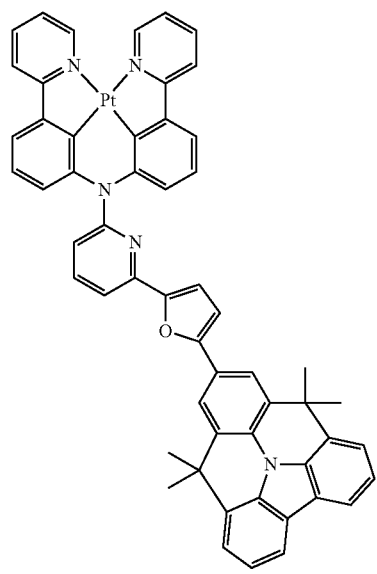
Formula (297)
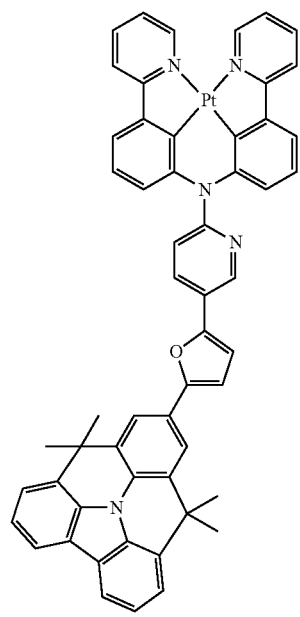

Formula (298)
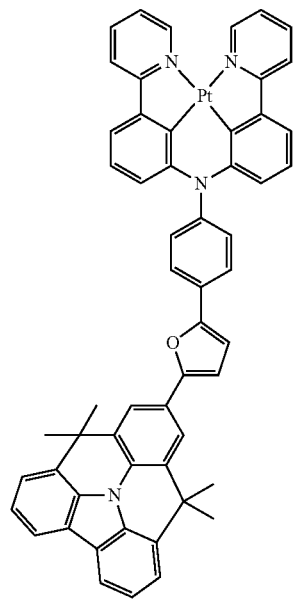
Formula (299)
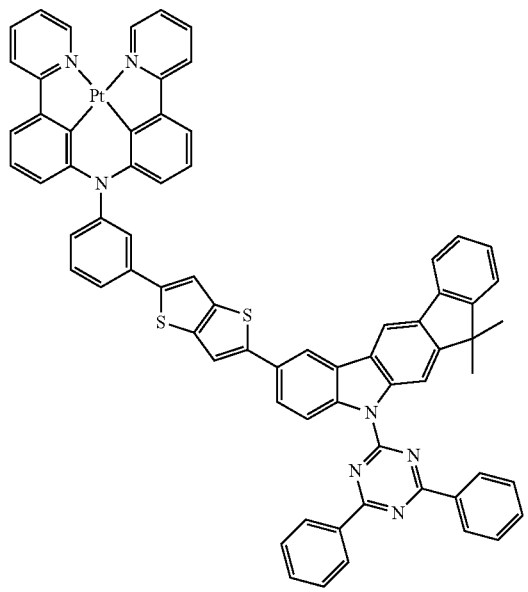
Formula (300)
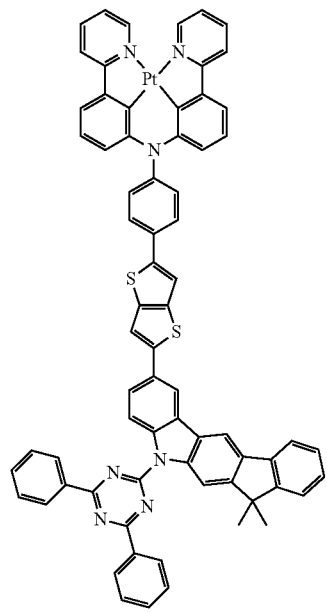
Formula (301)
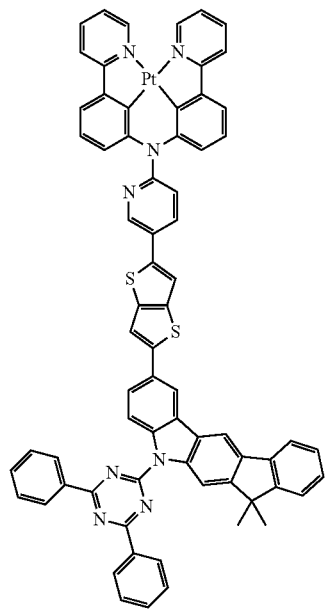

-continued
Formula (302)
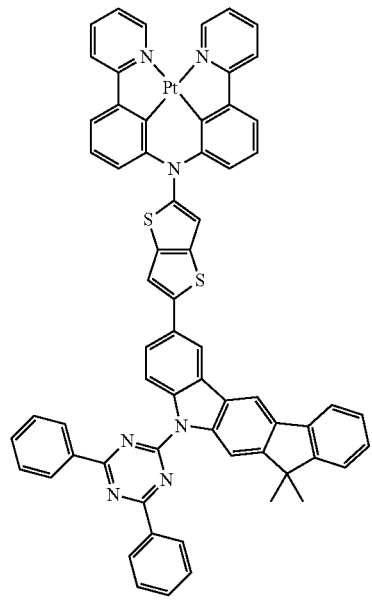
Formula (303)
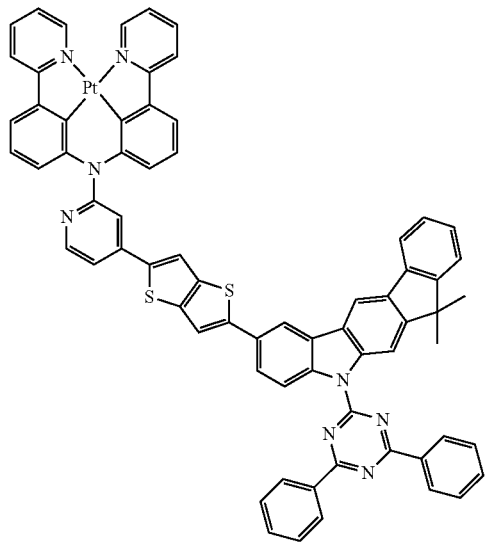
Formula (304)
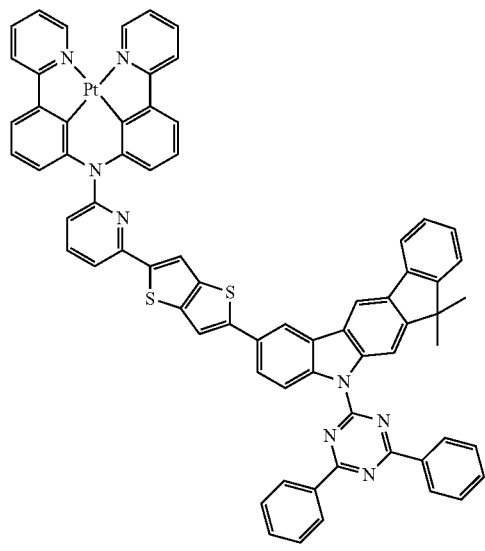
Formula (305)
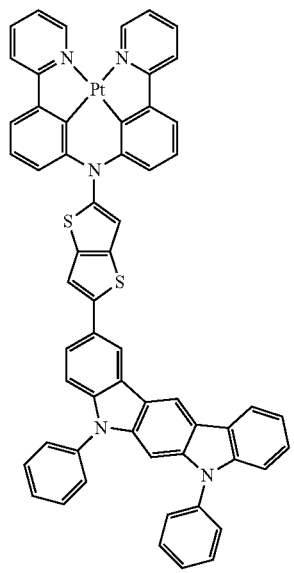

-continued
Formula (306)
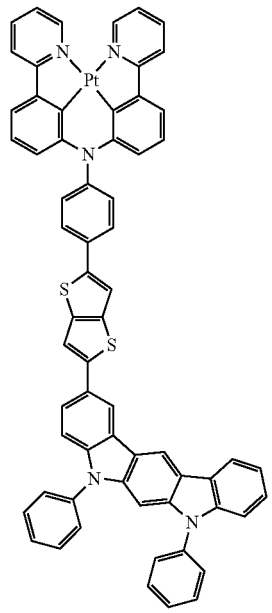
Formula (307)
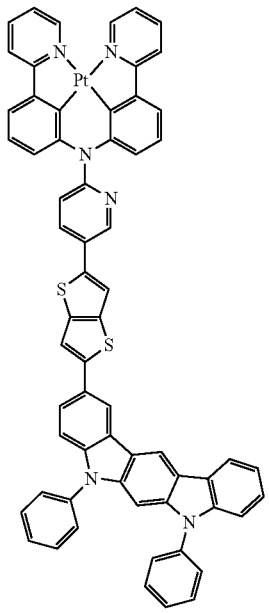
Formula (308)
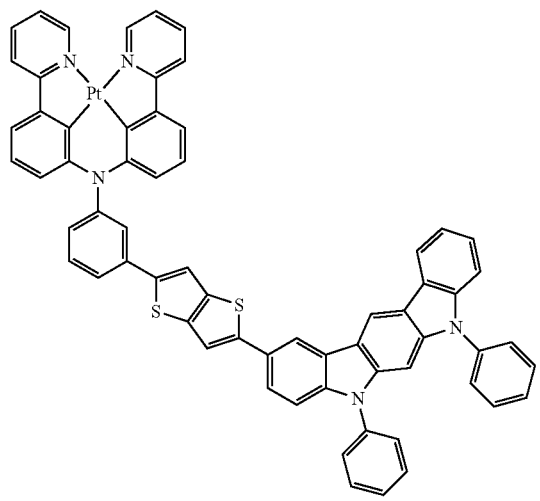
Formula (309)
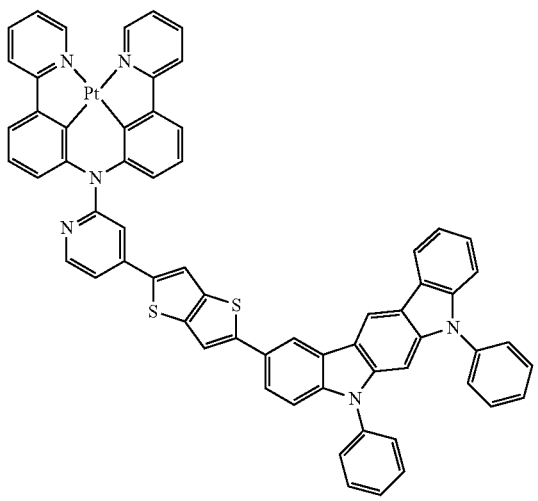
Formula (310)
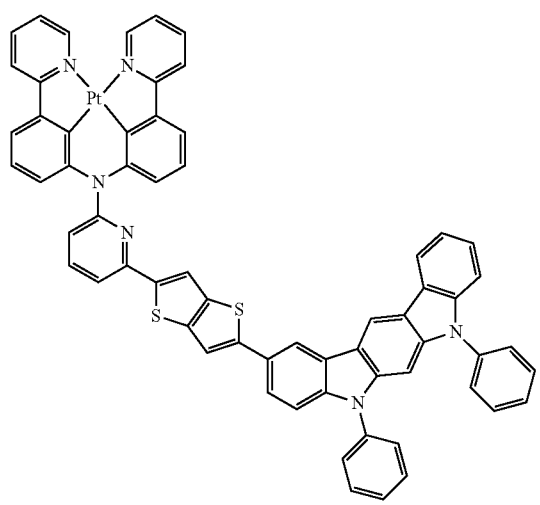
Formula (311)
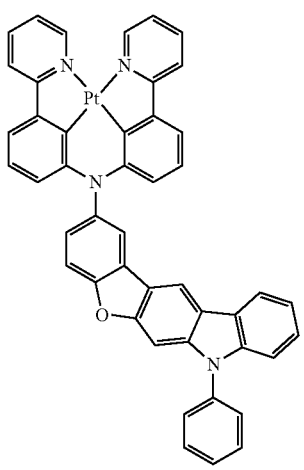

-continued
Formula (312)
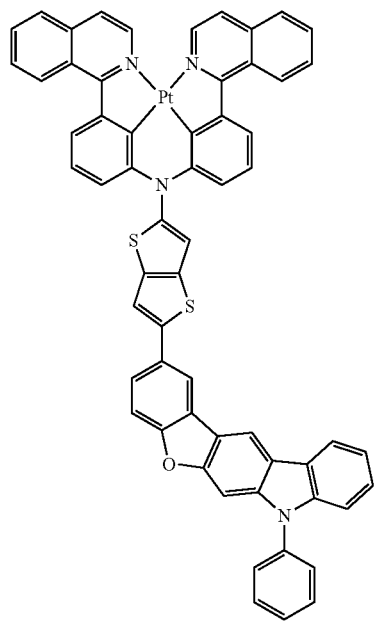
Formula (313)
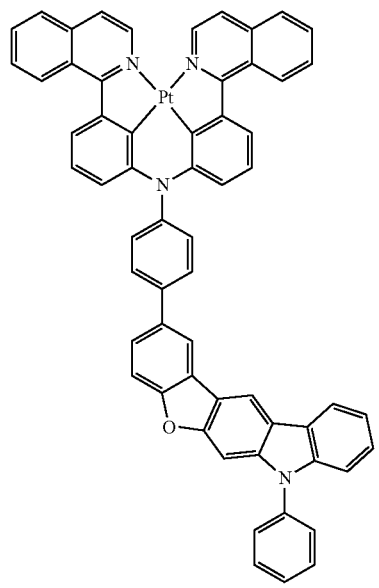
Formula (314)
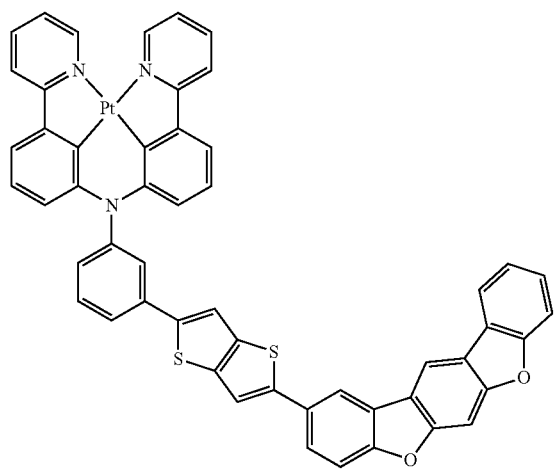
Formula (315)
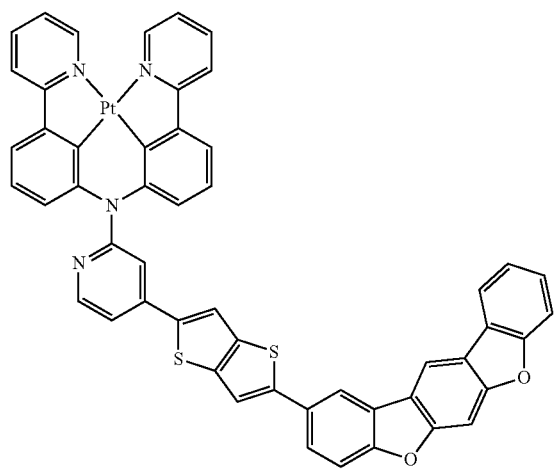

-continued
Formula (316)
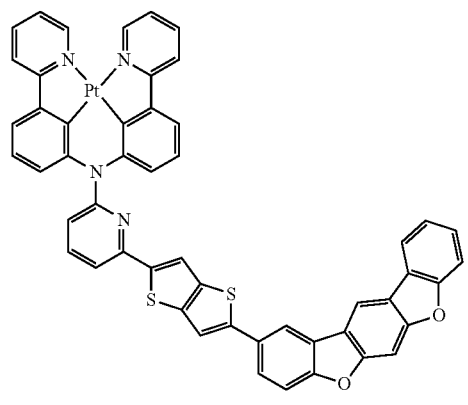
Formula (317)
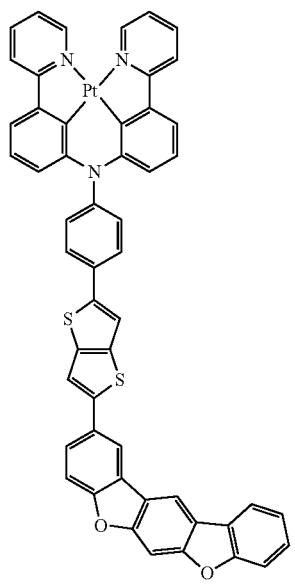
Formula (318)
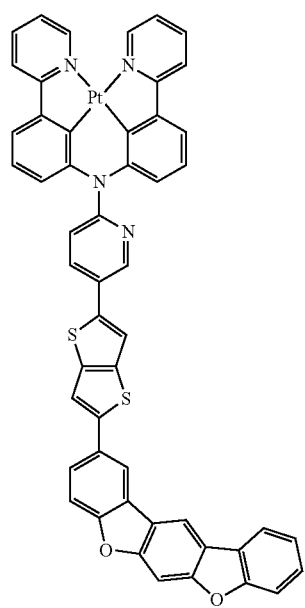
Formula (319)
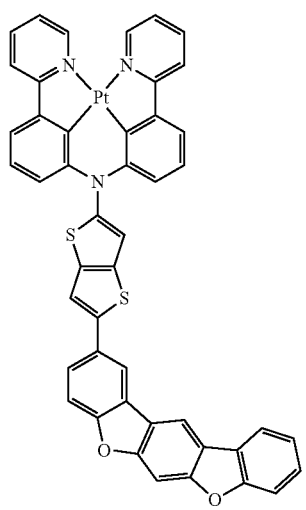

-continued
Formula (320)
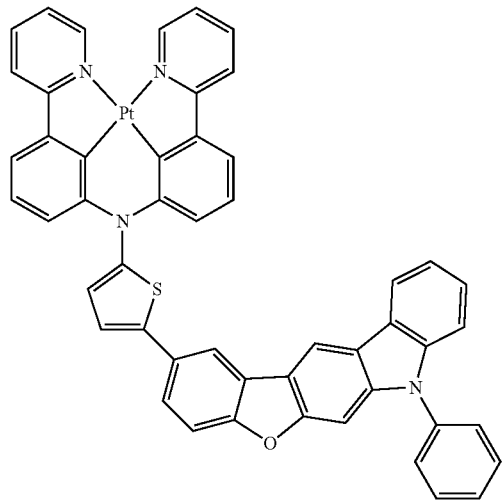
Formula (321)
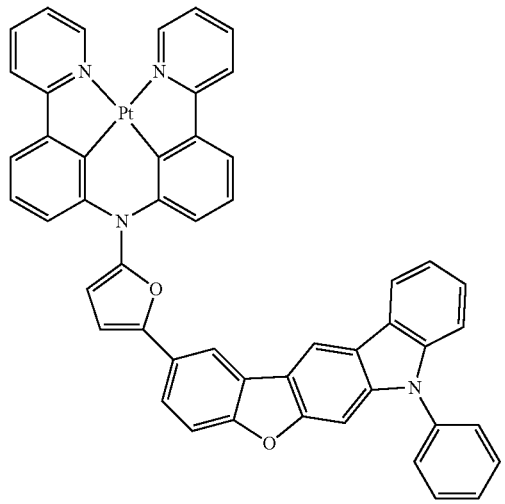
Formula (322)
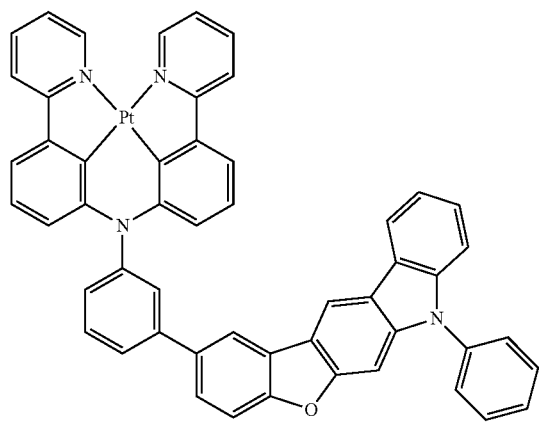
Formula (323)
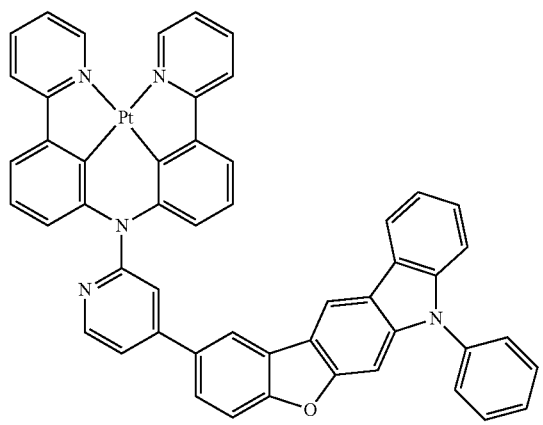
Formula (324)
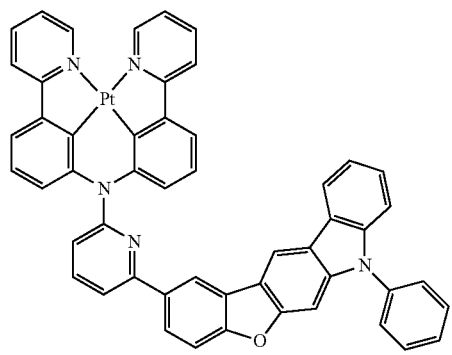
Formula (325)
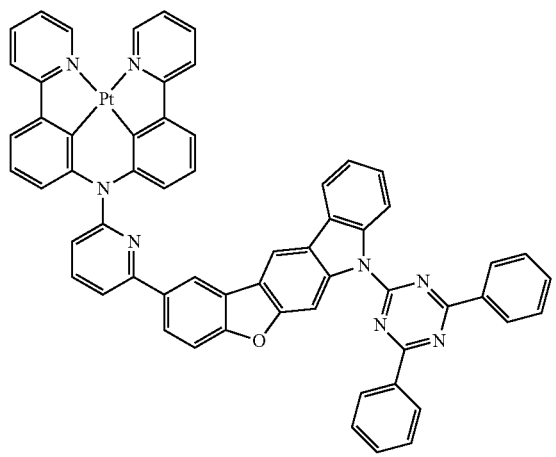

Formula (326)
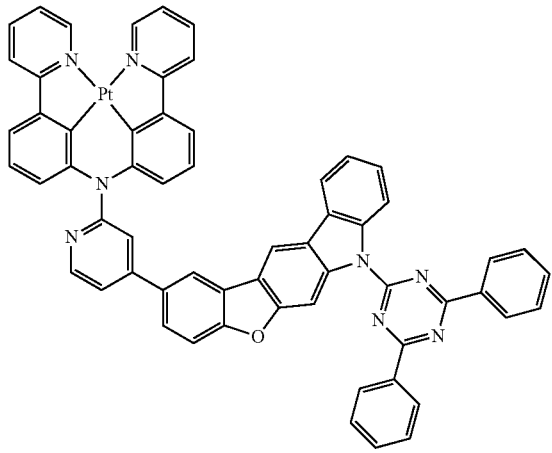
Formula (327)
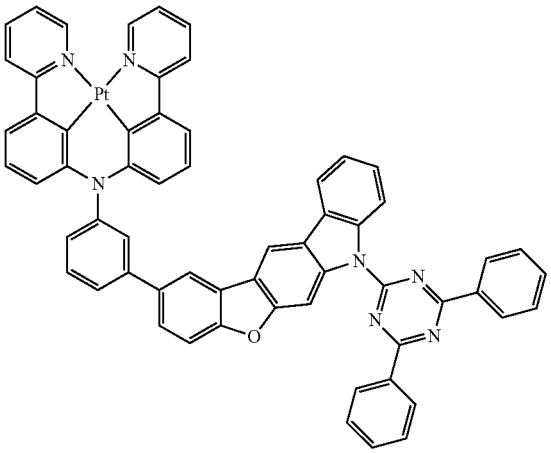
Formula (328)
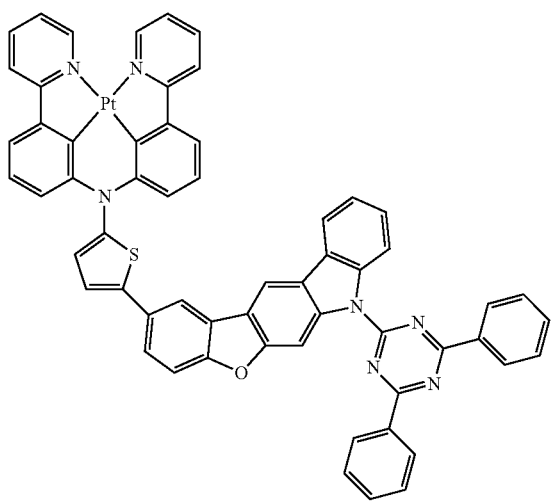
Formula (329)
Formula (330)
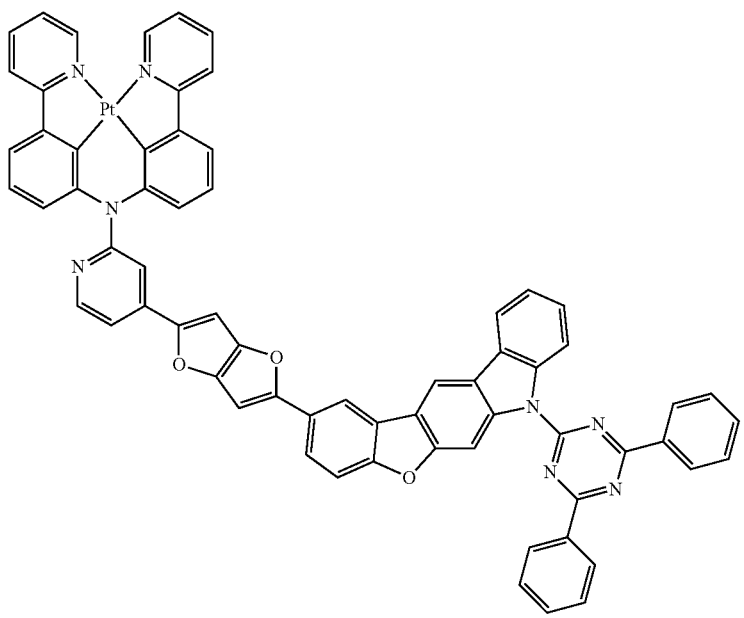

Formula (331)
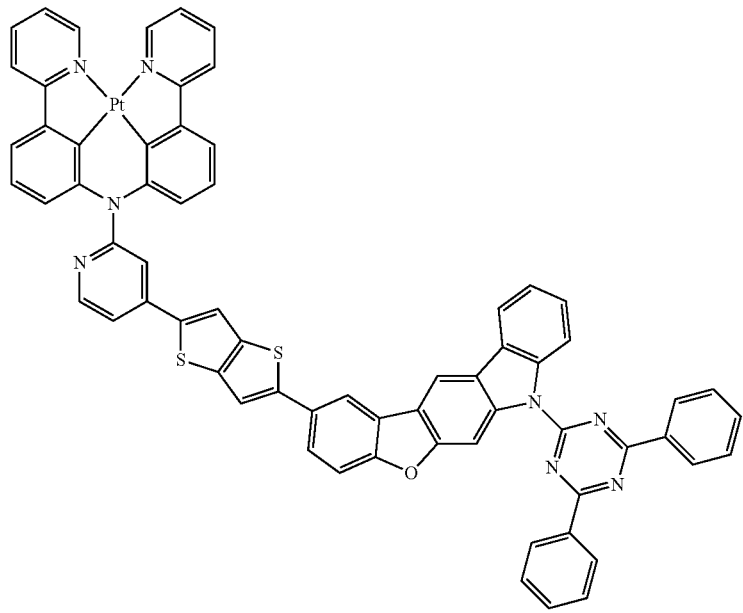
Formula (332)
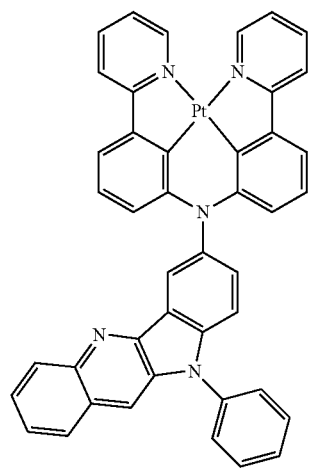
Formula (333)
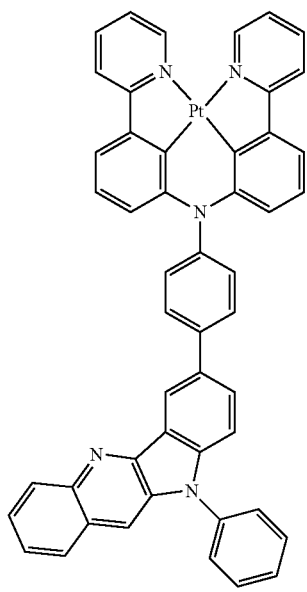

Formula (334)
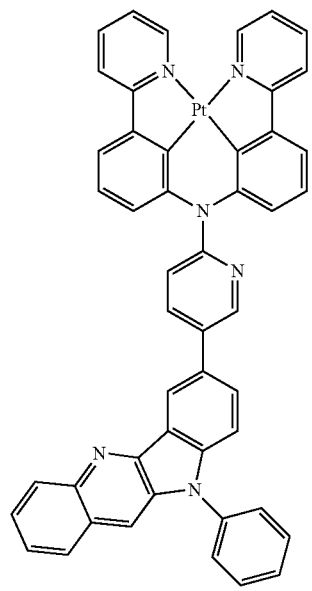
Formula (335)
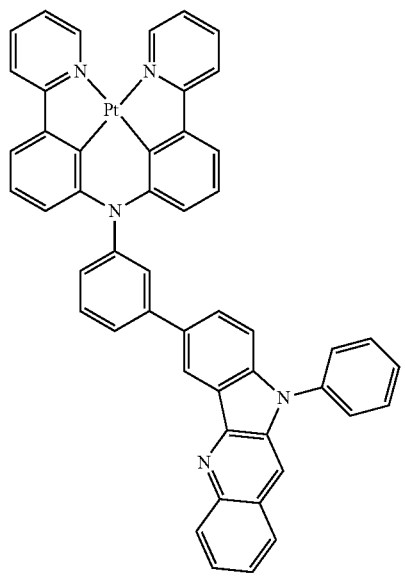
Formula (336)
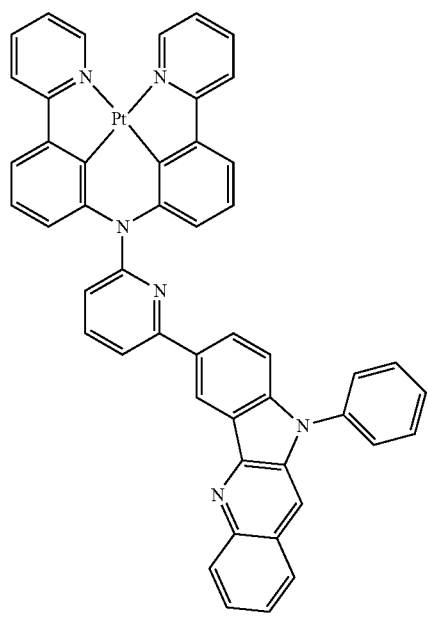
Formula (337)
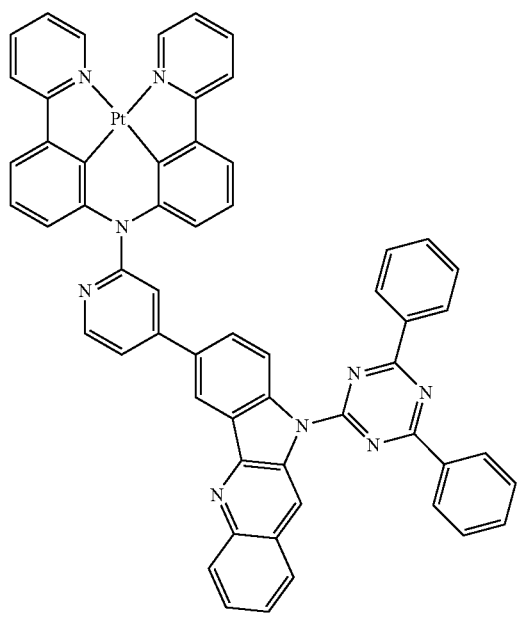

-continued
Formula (338)
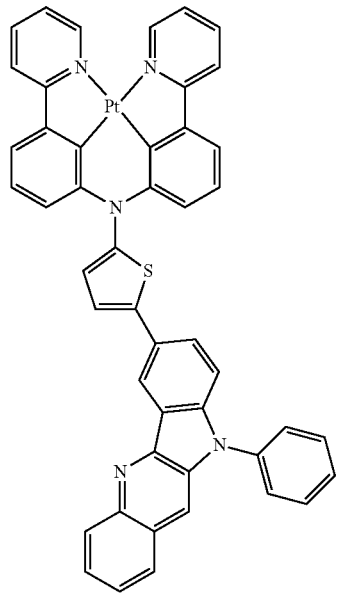
Formula (339)
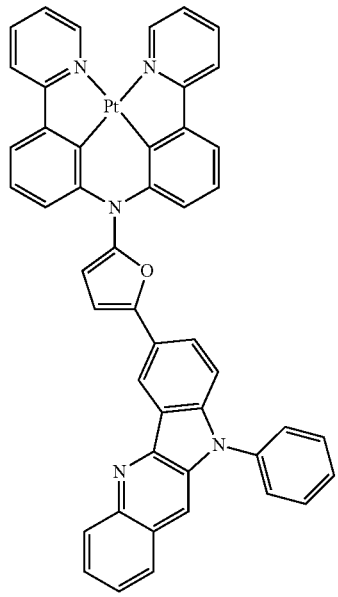
Formula (340)
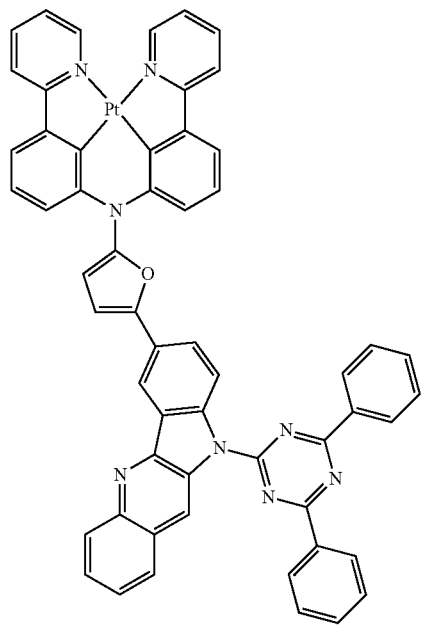
Formula (341)
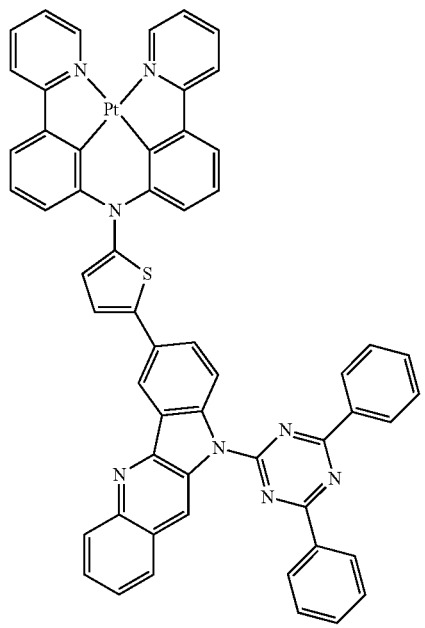

Formula (342)
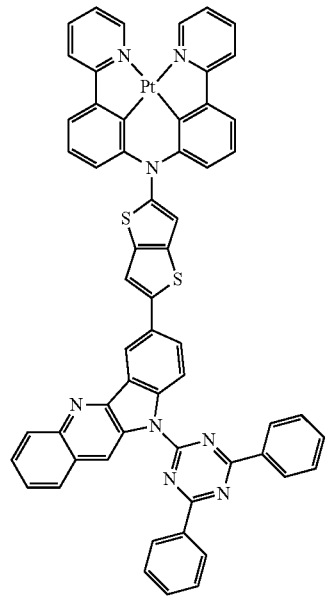
Formula (343)
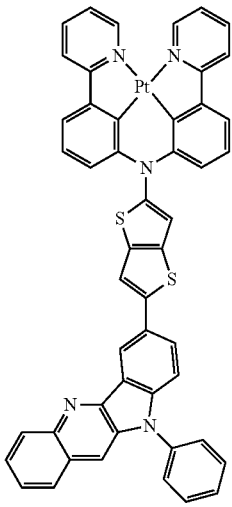
Formula (344)
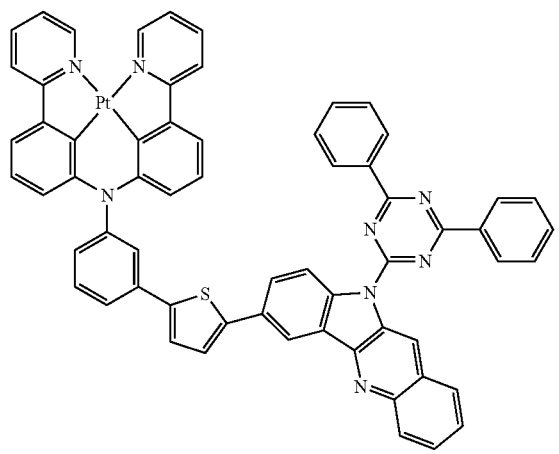
Formula (345)
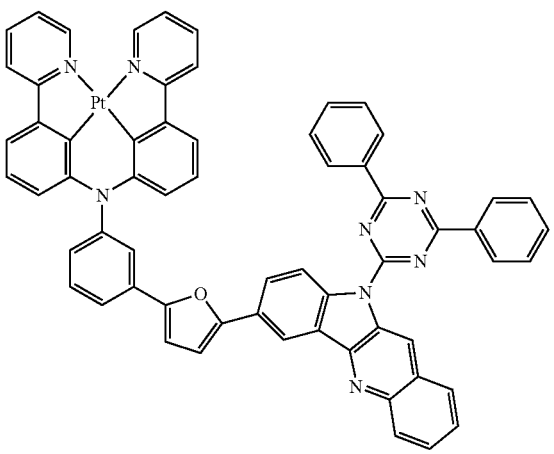

Formula (346)

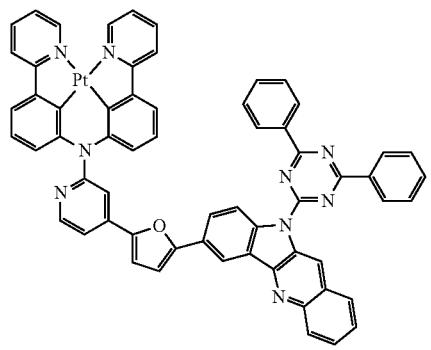

Formula (347)

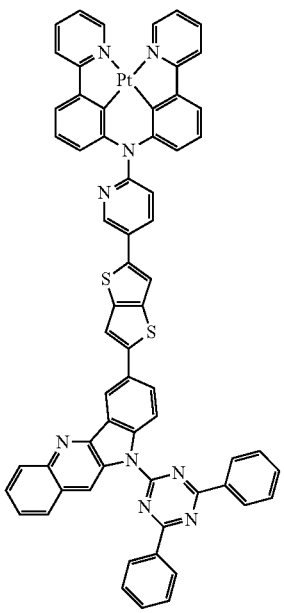

Formula (348)

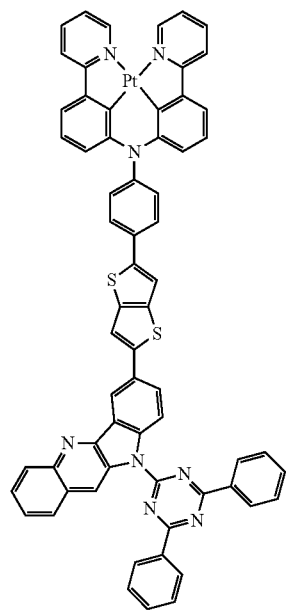

Formula (349)

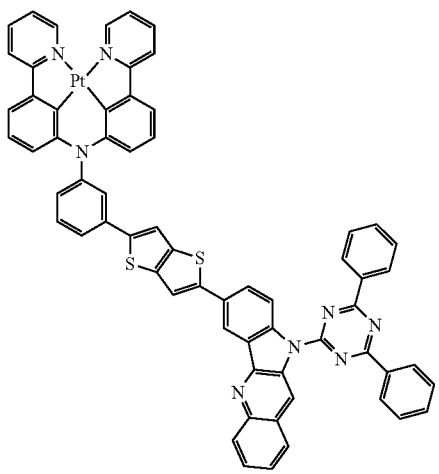

The complexes of the Formula (1) described above and the preferred embodiments mentioned above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the Formula (1) indicated above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising, in at least one layer, at least one compound of the Formula (1) indicated above. Particular preference is given to organic electroluminescent devices. Active components are generally the organic or inorganic materials, which are introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. It is likewise possible for interlayers, which have, for example, an exciton-blocking function and/or control the charge balance in the electroluminescent device, to be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 300 nm and 800 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which comprise more than three emitting layers.

In a preferred embodiment of the invention, the organic electroluminescent device comprises the compound of the Formula (1) or the preferred embodiments mentioned above as emitting compound in one or more emitting layers.

If the compound of the Formula (1) is employed as emitting compound in an emitting layer, it is preferably employed in combination with one or more matrix materials. The mixture of the compound of the Formula (1) and the matrix material comprises between 1 and 99% by weight, preferably between 2 and 50% by weight, particularly preferably between 3 and 40% by weight, in particular between 5 and 30% by weight, of the compound of the formula (1), based on the entire mixture comprising emitter and matrix material. Correspondingly, the mixture comprises between 99 and 1% by weight, preferably between 98 and 50% by weight, particularly preferably between 97 and 60% by weight, in particular between 95 and 70% by weight, of the matrix material, based on the entire mixture comprising emitter and matrix material.

Suitable matrix materials for the compounds according to the invention are ketones, phosphine oxides, sulfoxides and sulfones, for example in accordance with WO 2004/013080, WO 2004/093207, WO 2006/005627 or the application DE 102008033943, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with the applications DE 102009023155 and DE 102009031021, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with the application DE 102008036982, WO 2007/063754 or WO 2008/056746, zinc complexes, for example in accordance with EP 652273 or in accordance with WO 2009/062578, diaza- or tetraazasilole derivatives, for example in accordance with the application DE 102008056688, or diazaphosphole derivatives, for example in accordance with application DE 102009022858.

It may also be preferred to employ a plurality of different matrix materials as a mixture, in particular at least one electron-conducting matrix material and at least one hole-conducting matrix material. A preferred combination is, for example, the use of an aromatic ketone or a triazine with a triarylamine derivative or a carbazole derivative as mixed matrix for the metal complex according to the invention. Preference is likewise also given to mixtures of a hole- or electron-transporting material with a material which is involved in neither hole transport nor electron transport, as disclosed, for example, in DE 102009014513.

In a further preferred embodiment of the present invention, the compounds according to the invention can be employed in mixtures with one or more further emitters. Very particular preference is given here to a mixture of the compounds according to the invention with one or more fluorescent emitters. Preference is furthermore given to a mixture with one or more phosphorescent emitters. Fluorescent emitters emit principally from excited singlet states, whereas phosphorescent emitters emit light principally from higher spin states (for example triplet and quintet). For the purposes of this invention, the complexes of organic transition metals are taken to be phosphorescent emitters. The further emitters are preferably organic compounds.

In a particularly preferred embodiment of the present invention, the compounds according to the invention are mixed with 3 further emitters, in a particularly preferred embodiment with 2 further emitters and in an especially very preferred embodiment with one further emitter.

In a further preferred embodiment of the present invention, the emitter mixtures comprise 3, particularly preferably 2 and very particularly preferably one compound according to the invention.

In a particularly preferred embodiment of the present invention, the emitter mixtures comprise precisely one of the compounds according to the invention and precisely one further emitter.

It is furthermore preferred for the purposes of the present invention for the absorption spectra of at least one emitter and the emission spectrum of at least one other emitter of the mixture to overlap, simplifying energy transfer (double doping) between the emitters. The energy transfer here can take place by various mechanisms. Non-definitive examples of this are Förster or Dexter energy transfer.

The emitter mixtures described preferably comprise at least two emitters which both emit red light. Preference is furthermore given to emitter mixtures comprising at least two emitters which both emit green light. Preference is furthermore given to emitter mixtures comprising at least one emitter which emits red light and at least one emitter which emits green light.

The compound according to the present invention can, as outlined above, be mixed with further matrix materials. Besides matrix materials the compounds according to the present invention can also be mixed with any other organic functional material that is typically employed in electronic devices. Thus, the present invention also relates to a composition comprising at least one compound according to Formula (1) and at least one organic functional material selected from hole transport material (HTM), hole injection material (HIM), electron transport material (ETM), electron injection material (EIM), hole blocking material (HBM), exciton blocking material (ExBM), host or matrix material, fluorescent emitter, phosphorescent emitter, preferably matrix materials.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys of an alkali or alkaline-earth metal and silver, for example an alloy of magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent in order to enable either irradiation of the organic material (O-SCs) or the coupling-out of light (OLEDs/PLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive doped organic materials, in particular conductive doped polymers.

In general, all materials as used for the layers in accordance with the prior art can be used in the further layers, and the person skilled in the art will be able to combine each of these materials with the materials according to the invention in an electronic device without inventive step.

The device is correspondingly (depending on the application) structured, provided with contacts and finally hermetically sealed, since the lifetime of devices of this type is drastically shortened in the presence of water and/or air.

Preference is furthermore given to an organic electroluminescent device, characterized in that one or more layers are applied by means of a sublimation process, in which the materials are vapor-deposited in vacuum sublimation units at an initial pressure of usually less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterized in that one or more layers are applied by means of the OVPD (organic vapor phase deposition) process or with the aid of carrier-gas sublimation, in which the materials are applied at a pressure between $10^{-5}$ mbar and 1 bar. A special case of this process is the OVJP (organic vapor jet printing) process, in which the materials are applied directly through a nozzle and thus structured (for example M. S. Arnold et al., Appl. Phys. Lett. 2008, 92, 053301).

Preference is furthermore given to an organic electroluminescent device, characterized in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Since the compounds of the Formula (1) according to the invention have very good solubility in organic solvents, they are particularly suitable for processing from solution.

The organic electroluminescent device can also be produced as a hybrid system by applying one or more layers from solution and applying one or more other layers by vapor deposition. Thus, for example, it is possible to apply an emitting layer comprising a compound of the Formula (1) and a matrix material from solution and to apply a hole-blocking layer and/or an electron-transport layer on top by vacuum vapor deposition.

These processes are generally known to the person skilled in the art and can be applied by him without problems to organic electroluminescent devices comprising compounds of the Formula (1) or the preferred embodiments mentioned above.

For processing from solution, solutions or formulations of the compounds of the Formula (1) are necessary. It may also be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane, or mixtures of these solvents.

The present invention therefore furthermore relates to a solution or formulation comprising at least one compound of the Formula (1) and one or more solvents, in particular organic solvents. The way in which solutions of this type can be prepared is known to the person skilled in the art and is described, for example, in WO 02/072714, WO 03/019694 and the literature cited therein.

The electronic devices according to the invention, in particular organic electroluminescent devices, are distinguished by the following surprising advantages over the prior art:

1. The compounds of the Formula (1) have very good solubility in a multiplicity of common organic solvents and are therefore very highly suitable for processing from solution. In particular, the compounds according to the invention have higher solubility than the similar compounds described in the prior art;
2. Organic electroluminescent devices comprising compounds of the Formula (1) as emitting materials have an excellent lifetime. In particular, the lifetime is better than in the case of similar compounds in accordance with the prior art;
3. Organic electroluminescent devices comprising compounds of the Formula (1) as emitting materials have excellent efficiency. In particular, the efficiency is better than in the case of similar compounds in accordance with the prior art;
4. Devices comprising the compounds according to the present invention require lower voltages as compared to similar compounds of the prior art;
5. The compounds according to the present inventions or compositions or formulations comprising them show better film formation properties as compared to similar compounds of the prior art;

without lowering other electro-optical properties.

The compounds according to the invention are capable of emitting light under certain prerequisites. These compounds are thus very versatile.

Some of the principal areas of application here are display or illumination technologies. It is furthermore particularly advantageous to employ the compounds and devices comprising these compounds in the area of phototherapy.

The present invention therefore furthermore relates to the use of the compounds according to the invention and devices comprising the compounds for the treatment, prophylaxis and diagnosis of diseases. The present invention still furthermore relates to the use of the compounds according to the invention and devices comprising the compounds for the treatment and prophylaxis of cosmetic conditions.

The present invention furthermore relates to the use of the compounds according to the invention for the production of devices for the therapy, prophylaxis and/or diagnosis of therapeutic diseases and/or for cosmetic applications.

Phototherapy or light therapy is used in many medical and/or cosmetic areas. The compounds according to the invention and the devices comprising these compounds can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) and disinfection and sterilization in general. Phototherapy or light therapy can be used for the treatment of not only humans or animals, but also any other type of living or non-living materials. These include, for example, fungi, bacteria, microbes, viruses, eukaryotes, prokaryonts, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. The treatment or irradiation according to the invention can in addition also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers and desensitisation of the skin.

Particular preference is given for the purposes of the invention to the treatment and/or prophylaxis of psoriasis, acne, cellulite, skin wrinkling, skin ageing, jaundice and vitiligo.

Further areas of application according to the invention for the compositions and/or devices comprising the compositions according to the invention are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds and/or devices comprising the compounds according to the invention are selected from winter depression, sleeping sickness, irradiation for improving the mood, the reduction in pain, particularly muscular pain caused by, for example, tension or joint pain, elimination of the stiffness of joints and the whitening of the teeth (bleaching).

Further areas of application according to the invention for the compounds and/or devices comprising the compounds according to the invention are selected from the group of disinfections. The compounds according to the invention and/or the devices according to the invention can be used for the treatment of any type of objects (non-living materials) or subjects (living materials such as, for example, humans and animals) for the purposes of disinfection. This includes, for example, the disinfection of wounds, the reduction in bacteria, the disinfection of surgical instruments or other articles, the disinfection of foods, of liquids, in particular water, drinking water and other drinks, the disinfection of mucous membranes and gums and teeth. Disinfection here is taken to mean the reduction in the living micro-biological causative agents of undesired effects, such as bacteria and germs.

For the purposes of the phototherapy mentioned above, devices comprising the compounds according to the invention preferably emit light having a wavelength between 250 and 1250 nm, particularly preferably between 300 and 1000 nm and particularly preferably between 400 and 850 nm.

In a particularly preferred embodiment of the present invention, the compounds according to the invention are employed in an organic light-emitting diode (OLED) or an organic light-emitting electrochemical cell (OLEC) for the purposes of phototherapy. Both the OLED and the OLEC can have a planar or fiber-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, caps, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for re-use or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples without wishing it to be restricted thereby.

WORKING EXAMPLES

Examples

The following syntheses are, unless indicated otherwise, carried out under a protective-gas atmosphere in dried solvents. Compounds (I) and (V) can be prepared in accordance with WO 2005/042444. Compounds (II), (VIII) and (XIII) can be prepared in accordance with WO2010/136109. Compound (X) can be prepared in accordance with Synthetic Communications, 40(1), 58-63, 2010. Compound (XVI) can be prepared according to Journal of Heterocyclic Chemistry, 29(5), 1237-1239; 1992. Compound (XVII) is commercial product from Aldrich. Compound (XXI) can be prepared in accordance with WO 2010/050778.

Example 1

Preparation of Compound (IV)

Synthetic Procedure for the Preparation of Compound (IV):

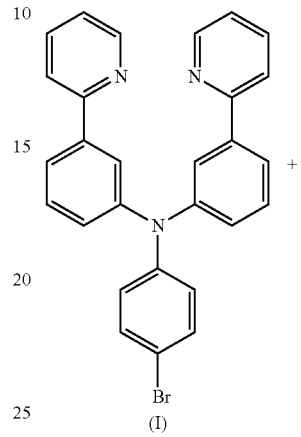
(I)

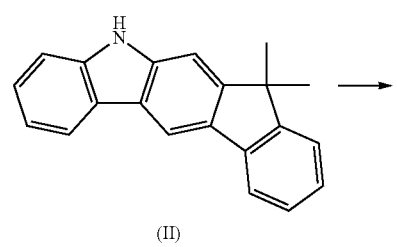
(II)

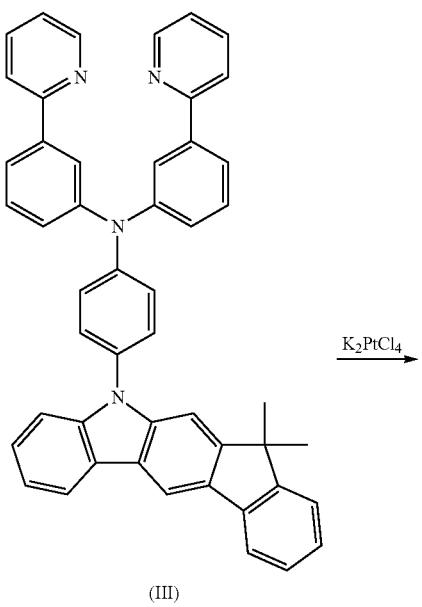
(III)

105

-continued

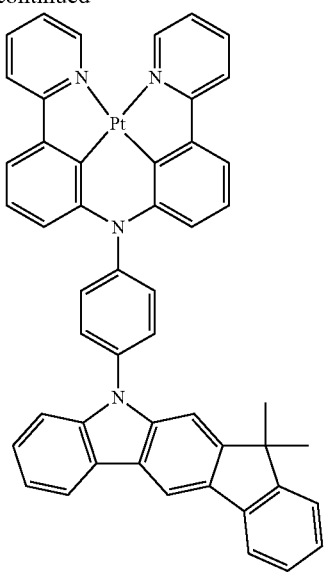

(IV)

Preparation of Compound (III)

13.8 g (28.8 mmol) of compound (I), 7.4 g (26.2 mmol) of compound (II) and 3.0 g (31.4 mmol) of sodium t-butoxide are suspended in 200 mL of toluene. 176 mg (0.78 mmol) of Pd(OAc)$_2$ and 1.3 mL of a 1 M tri-tert-butylphosphine solution are added to this suspension. The reaction mixture is heated under reflux for 24 h. After cooling, the organic phase is separated off, washed three times with 200 mL of water, dried over magnesium sulfate, filtered and subsequently evaporated to dryness. The residue is purified by column chromatography on silica gel using a mixture of ethylacetate/heptane (1:2). The yield is 13.2 g (19.4 mmol), corresponding to 74% of theory.

Preparation of Compound (IV)

13.0 g (19.1 mmol) of compound (III) and 7.9 g (19.1 mmol) of potassium platinum(II) chloride are heated under reflux for 72 h in 100 mL of acetic acid. After cooling, the mixture is evaporated to dryness, and 100 mL of dichloromethane (dcm) and 200 mL of water are added to the crude product. The organic phase is separated off, washed three times with 300 mL of water, dried over magnesium sulfate, filtered and subsequently evaporated to dryness. The residue is purified by column chromatography on silica gel using dcm as eluting solvent. The yield is 7.2 g (8.2 mmol), corresponding to 43% of theory.

106

Example 2

Preparation of Compound (VII)

Synthetic Procedure for the Preparation of Compound (VII):

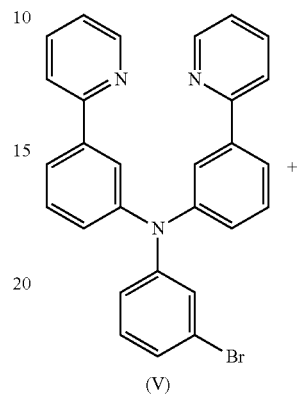

(V)

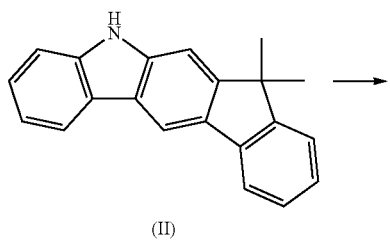

(II)

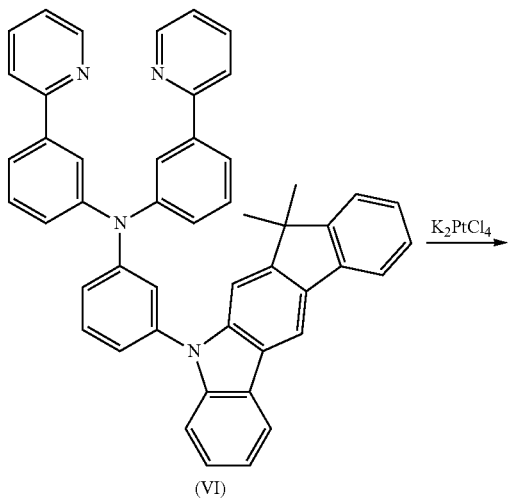

(VI)

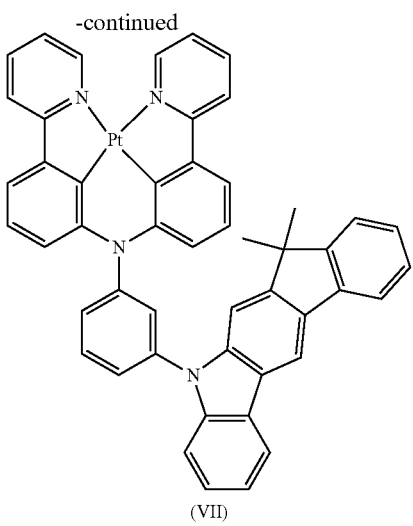

(VII)

Preparation of Compound (VI)

14.5 g (30.3 mmol) of compound (V), 7.8 g (27.5 mmol) of compound (II) and 3.2 g (33.0 mmol) of sodium t-butoxide are suspended in 200 mL of toluene. 185 mg (0.82 mmol) of Pd(OAc)$_2$ and 1.3 mL of a 1 M tri-tert-butylphosphine solution are added to this suspension. The reaction mixture is heated under reflux for 27 h. After cooling, the organic phase is separated off, washed three times with 300 mL of water and subsequently evaporated to dryness. The residue is purified by column chromatography using a mixture of ethylacetate/heptane (1:2). The yield is 13.3 g (19.5 mmol), corresponding to 71% of theory.

Preparation of Compound (VII)

13.1 g (19.2 mmol) of compound (VI) and 8.0 g (19.2 mmol) of potassium platinum(II) chloride are heated under reflux for 72 h in 100 mL of acetic acid. After cooling, the mixture is evaporated to dryness, and 100 mL of dcm and 300 mL of water are added to the crude product. The organic phase is separated off, washed three times with 300 mL of water, dried over magnesium sulfate, filtered and subsequently evaporated to dryness. The residue is purified by column chromatography on silica gel using dcm as eluting solvent. The yield is 7.0 g (8.0 mmol), corresponding to 42% of theory.

Example 3: Preparation of Compound (XII)

Synthetic Procedure for the Preparation of Compound (XII):

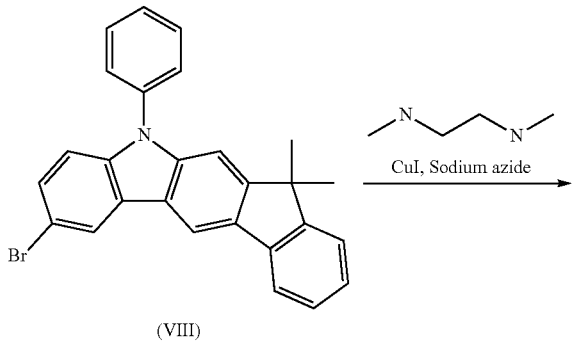

(VIII)

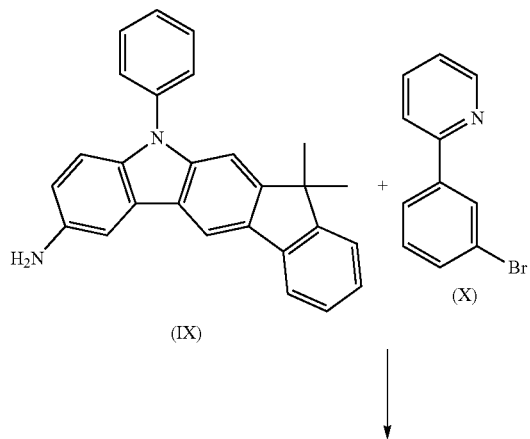

(IX)  (X)

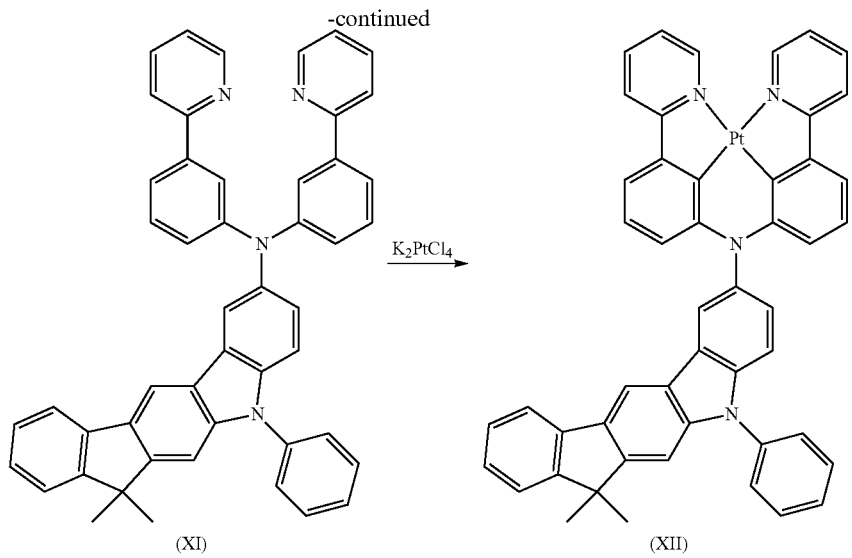

(XI)                                                                    (XII)

Preparation of Compound (IX)

22.4 g (51.1 mmol) of compound (VIII), 9.7 g (51.1 mmol) of copper iodide, 6.6 g (102.2 mmol) of sodium azide, 5.4 g (61.3 mmol) of N,N-dimethylethane-1,2-diamine are heated under reflux for 10 h in 300 mL of dimethylsulfoxide (DMSO). After cooling, 200 mL of ethylacetate and 100 mL of a solution of saturated NH$_4$Cl are added to the reaction mixture. The organic phase is separated off, washed three times with 300 mL of water, dried over magnesium sulfate, filtered and subsequently evaporated to dryness. The residue is recrystallised from toluene and finally dried under reduced pressure. The yield is 11.3 g (30.2 mmol), corresponding to 59% of theory.

Preparation of Compound (XI)

11.1 g (29.6 mmol) of compound (IX), 13.9 g (62.2 mmol) of compound (X) and 6.8 g (71.0 mmol) of sodium t-butoxide are suspended in 250 mL of toluene. 332 mg (1.5 mmol) of Pd(OAc)$_2$ and 2.4 mL of a 1 M tri-tert-butylphosphine solution are added to this suspension. The reaction mixture is heated under reflux for 28 h. After cooling, the organic phase is separated off, washed three times with 300 mL of water, dried over magnesium sulfate, filtered and subsequently evaporated to dryness. The residue is purified by column chromatography on silica gel using a mixture of ethylacetate/heptane (1:2). The yield is 12.8 g (18.8 mmol), corresponding to 64% of theory.

Preparation of Compound (XII)

12.5 g (18.4 mmol) of compound (XI) and 7.6 g (18.4 mmol) of potassium platinum(II) chloride are heated under reflux for 72 h in 100 mL of acetic acid. After cooling, the mixture is evaporated to dryness, and 100 mL of dcm and 300 mL of water are added to the crude product. The organic phase is separated off, washed three times with 300 mL of water, dried over magnesium sulfate, filtered and subsequently evaporated to dryness. The residue is purified by column chromatography on silica gel using dcm as eluting solvent. The yield is 6.9 g (7.9 mmol), corresponding to 43% of theory.

Example 4: Preparation of Compound (XV)

Synthetic Procedure for the Preparation of Compound (XV):

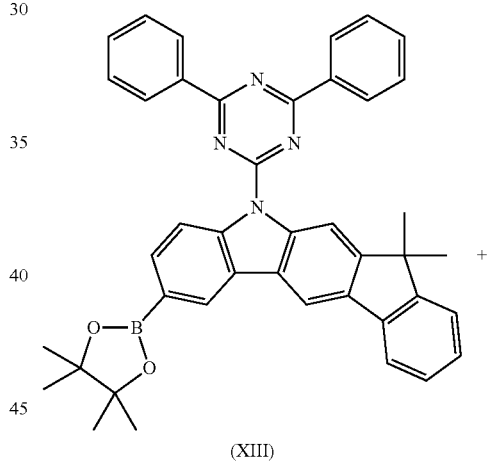

(XIII)

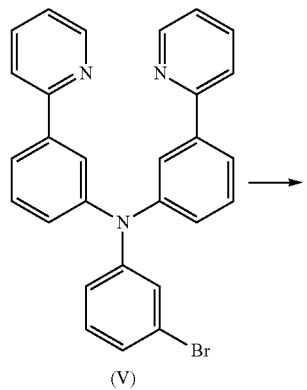

(V)

-continued

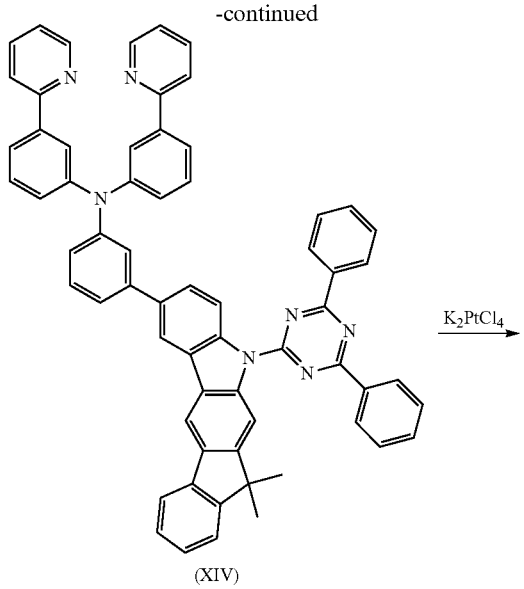

(XIV)

(XV)

Preparation of Compound (XIV)

12.1 g (25.4 mmol) of compound (V), 18.1 g (30.4 mmol) of compound (XIII) and 4.2 g (30.4 mmol) of potassium carbonate are suspended in 300 mL of toluene and 100 mL of water. 290 mg (0.25 mmol) of tetrakis(triphenyl-phosphine)palladium(0) are added to this suspension, and the reaction mixture is heated under reflux for 48 h. After cooling, the organic phase is separated off, washed three times with 300 mL of water, dried over sodium sulfate and subsequently evaporated to dryness. The residue is purified by column chromatography using a mixture of ethylacetate/heptane (1:2). The yield is 15.2 g (16.7 mmol), corresponding to 66% of theory.

Preparation of Compound (XV)

15.0 g (16.5 mmol) of compound (XIV) and 6.8 g (16.5 mmol) of potassium platinum(II) chloride are heated under reflux for 72 h in 100 mL of acetic acid. After cooling, the mixture is evaporated to dryness, and 100 mL of dcm and 300 mL of water are added to the crude product. The organic phase is separated off, washed three times with 300 mL of water, dried over magnesium sulfate, filtered and subsequently evaporated to dryness. The residue is purified by column chromatography on silica gel using dcm as eluting solvent. The yield is 7.8 g (7.1 mmol), corresponding to 43% of theory.

Example 5

Preparation of Compound (XX)

Synthetic Procedure for the Preparation of Compound (XX):

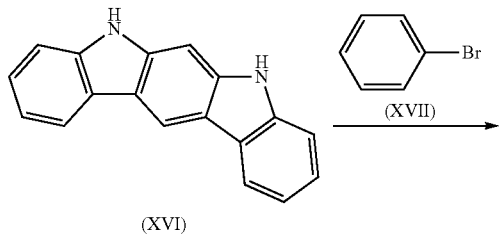

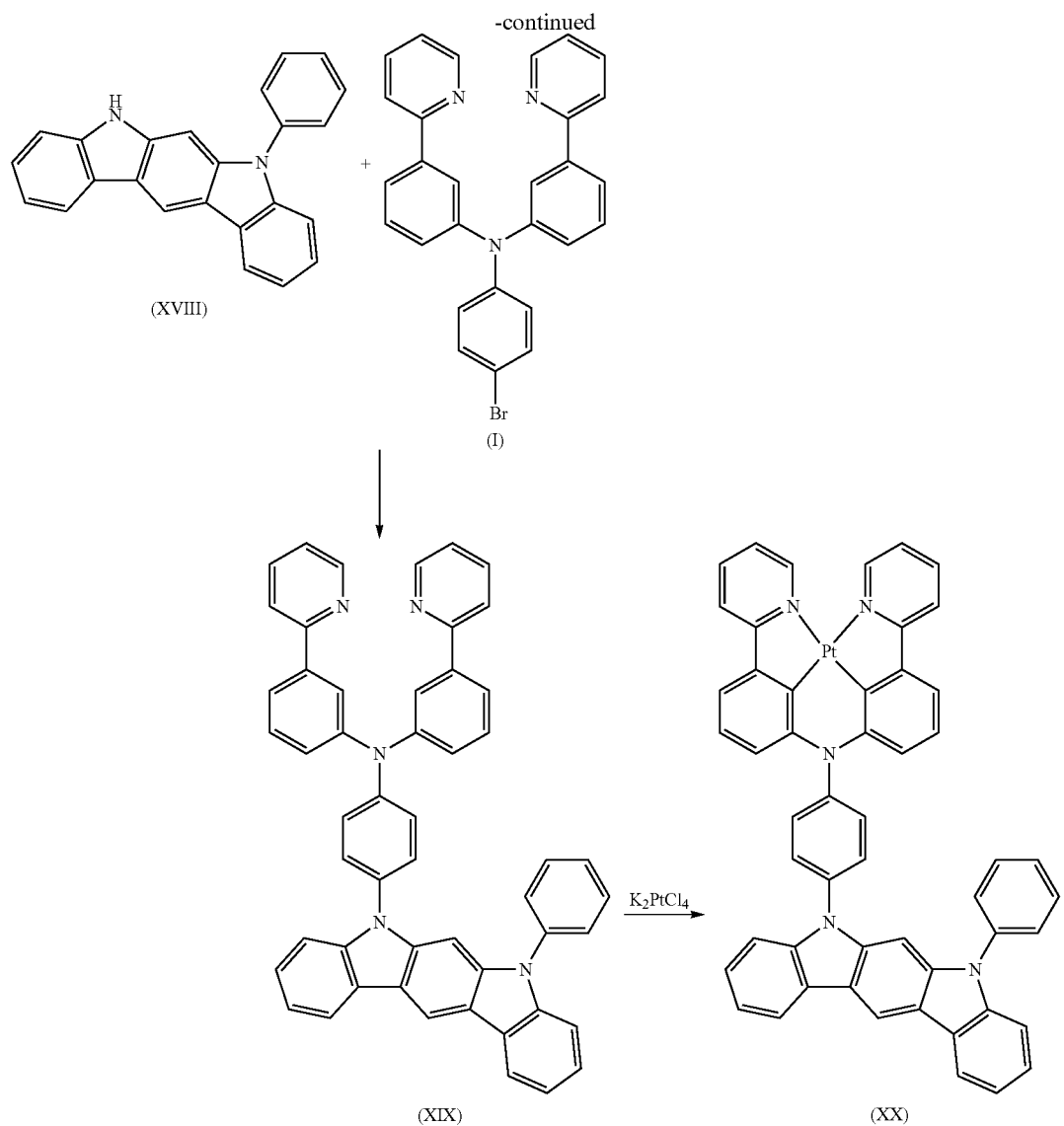

Preparation of compound (XVIII) 15.0 g (58.5 mmol) of compound (XVI), 10.1 g (64.4 mmol) of compound (XVII) and 6.7 g (70.2 mmol) of sodium t-butoxide are suspended in 250 mL of toluene. 390 mg (1.8 mmol) of Pd(OAc)$_2$ and 2.9 mL of a 1 M tri-tert-butylphosphine solution are added to this suspension. The reaction mixture is heated under reflux for 24 h. After cooling, the organic phase is separated off, washed three times with 200 mL of water, dried over magnesium sulfate, filtered and subsequently evaporated to dryness. The residue is purified by column chromatography on silica gel using a mixture of ethylacetate/heptane (1:4). The yield is 13.3 g (40.0 mmol), corresponding to 68% of theory.

Preparation of Compound (XIX)

13.0 g (39.2 mmol) of compound (XVIII), 17.0 g (35.6 mmol) of compound (I) and 4.1 g (42.7 mmol) of sodium t-butoxide are suspended in 250 mL of toluene. 240 mg (1.1 mmol) of Pd(OAc)$_2$ and 1.8 mL of a 1 M tri-tert-butylphosphine solution are added to this suspension. The reaction mixture is heated under reflux for 21 h. After cooling, the organic phase is separated off, washed three times with 200 mL of water, dried over magnesium sulfate, filtered and subsequently evaporated to dryness. The residue is purified by column chromatography on silica gel using a mixture of ethylacetate/heptane (1:2). The yield is 16.8 g (23.0 mmol), corresponding to 65% of theory.

Preparation of Compound (XX)

16.6 g (22.8 mmol) of compound (XIX) and 9.5 g (22.8 mmol) of potassium platinum(II) chloride are heated under reflux for 72 h in 100 mL of acetic acid. After cooling, the mixture is evaporated to dryness, and 100 mL of dcm and 300 mL of water are added to the crude product. The organic phase is separated off, washed three times with 300 mL of water, dried over magnesium sulfate, filtered and subsequently evaporated to dryness. The residue is purified by column chromatography on silica gel using dcm as eluting solvent. The yield is 8.4 g (9.1 mmol), corresponding to 40% of theory.

Example 6

Preparation of Compound (XXIV)

Synthetic Procedure for the Preparation of Compound (XXIV)

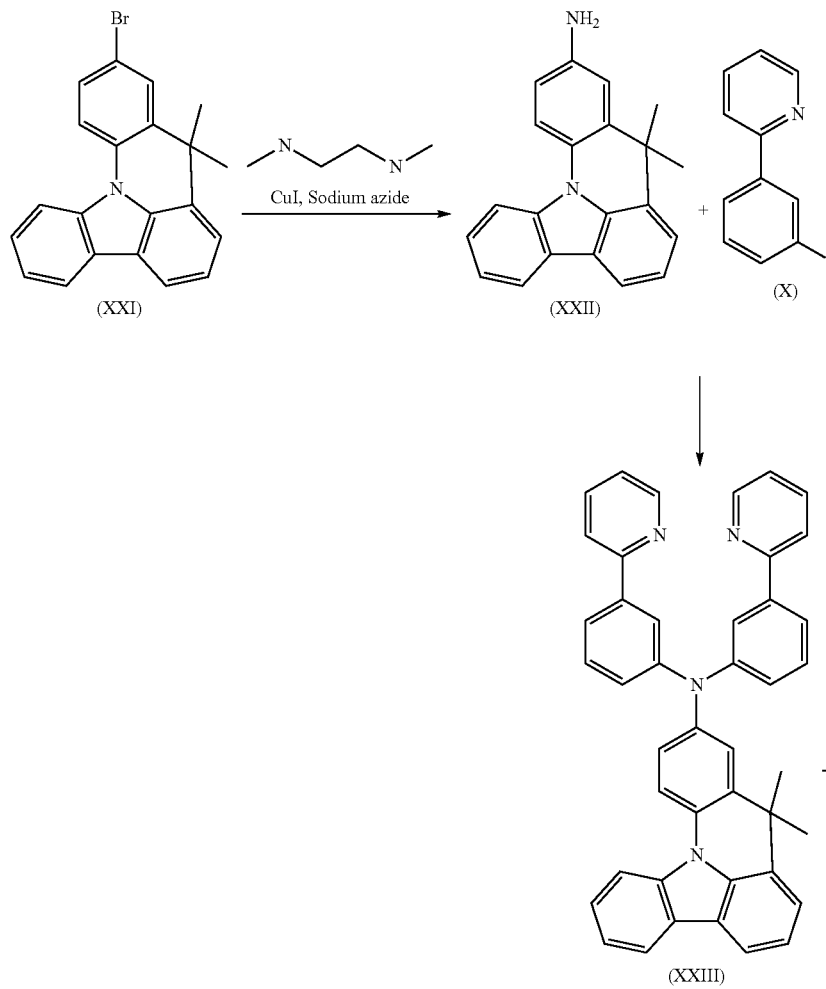

Preparation of Compound (XXII)

18.5 g (51.1 mmol) of compound (XXI), 9.7 g (51.1 mmol) of copper iodide, 6.6 g (102.2 mmol) of sodium azide and 5.4 g (61.3 mmol) of N,N-dimethylethane-1,2-diamine are heated under reflux for 10 h in 300 mL of dmso. After cooling, 200 mm of ethylacetate and 100 mL of a solution of saturated $NH_4Cl$ are added to the reaction mixture. The organic phase is separated off, washed three times with 300 mL of water, dried over magnesium sulfate, filtered and subsequently evaporated to dryness. The residue is recrystallised from a mixture of toluene/ethanol and finally dried under reduced pressure. The yield is 8.8 g (29.5 mmol), corresponding to 58% of theory.

Preparation of Compound (XXIII)

8.5 g (28.5 mmol) of compound (XII), 14.1 g (60.1 mmol) of compound (X) and 6.6 g (68.6 mmol) of sodium t-butoxide are suspended in 250 mL of toluene. 320 mg (1.4 mmol) of $Pd(OAc)_2$ and 2.2 mL of a 1 M tri-tert-butylphosphine solution are added to this suspension. The reaction mixture is heated under reflux for 27 h. After cooling, the organic phase is separated off, washed three times with 200 mL of water, dried over magnesium sulfate, filtered and subsequently evaporated to dryness. The residue is purified by column chromatography on silica gel using a mixture of ethylacetate/heptane (1:2). The yield is 11.3 g (18.7 mmol), corresponding to 66% of theory.

Preparation of Compound (XXIV)

11.1 g (18.4 mmol) of compound (XXIII) and 7.6 g (18.4 mmol) of potassium platinum(II) chloride are heated under reflux for 72 h in 100 mL of acetic acid. After cooling, the mixture is evaporated to dryness, and 100 mL of dcm and 300 mL of water are added to the crude product. The organic phase is separated off, washed three times with 300 mL of water, dried over magnesium sulfate, filtered and subsequently evaporated to dryness. The residue is purified by column chromatography on silica gel using dcm as eluting solvent. The yield is 6.1 g (7.7 mmol), corresponding to 42% of theory.

Examples 7 to 13
Production and Characterization of Organic Electroluminescent Devices
The structures of compounds TE-1 to TE-6 according to the invention, TMM-1 (synthesized in accordance with DE 102008036982-WO 2010/015306) and TMM-2 (synthesized in accordance with DE 102008017591-WO 2009/124627) are depicted below for clarity.
Structures of the Emitters Related to this Invention
TE-1
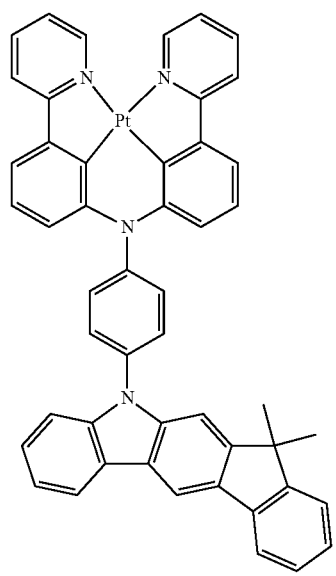
TE-2
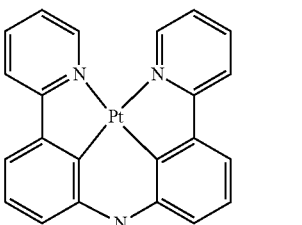
TE-3
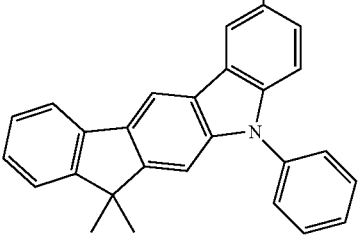
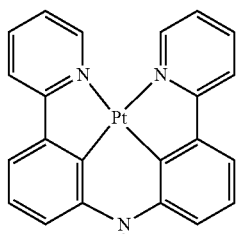
TE-4
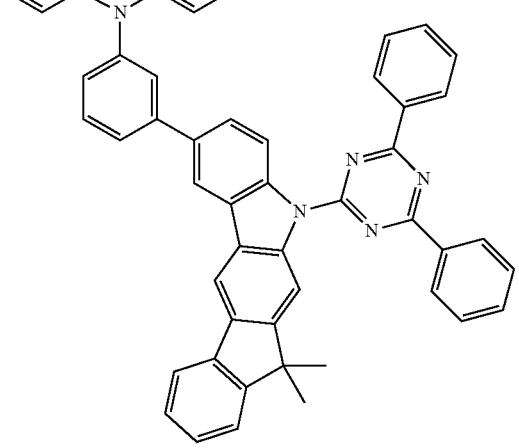

TE-5

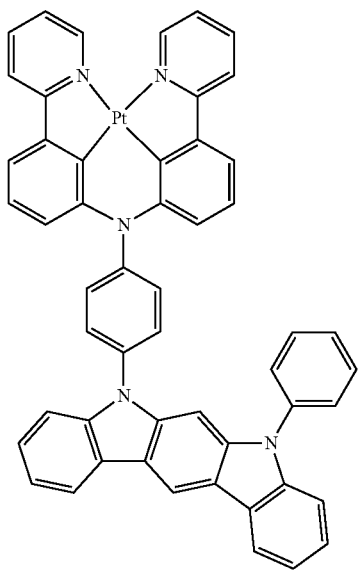

TE-C

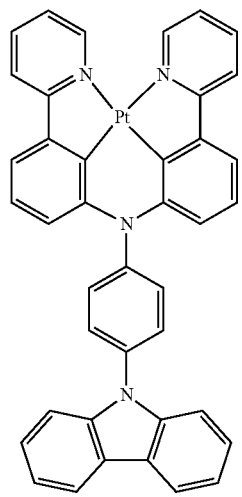

Structures of the Matrices

TMM-1

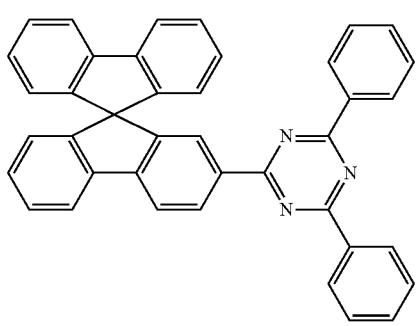

TMM-2

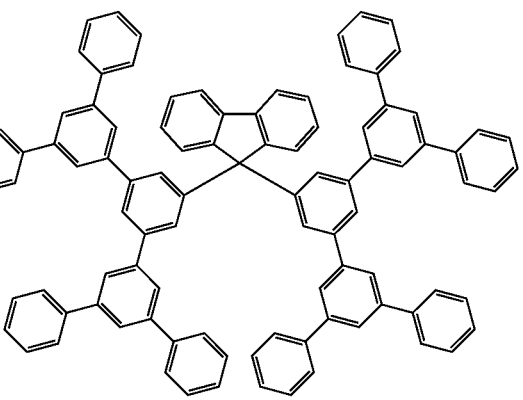

TE-6

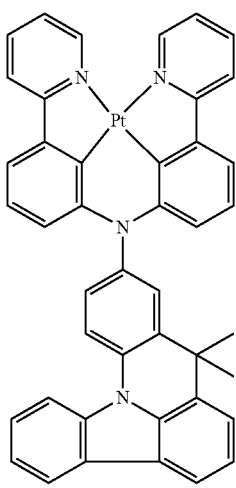

Structure of the Emitter Related to the Comparative Example (Synthesized According to WO 2005/042444)

Materials according to the invention can be used from solution, where they result in simple devices having good properties. The production of such components is based on the production of polymeric light-emitting diodes (PLEDs), which has already been described a number of times in the literature (for example in WO 2004/037887). In the present case, compounds TE-1 to TE-6 according to the invention are dissolved in toluene. The typical solids content of such solutions is between 16 and 25 g/l if, as here, the typical layer thickness of 80 nm for a device is to be achieved by means of spin coating. Structured ITO substrates and the material for the so-called buffer layer (PEDOT, actually PEDOT:PSS) are commercially available (ITO from Technoprint and others, PEDOT:PSS as Clevios Baytron P aqueous dispersion from H. C. Starck). The interlayer used serves for hole injection; in this case, HIL-012 from Merck is used. The emission layer is applied by spin coating in an inert-gas atmosphere, in the present case argon, and dried by heating at 160° C. for 10 min. Finally, a cathode comprising barium and aluminium is applied by vacuum vapor deposition. A hole-blocking layer and/or an electron-transport layer can also be applied between the emitting layer and the cathode by vapor deposition, and the interlayer may also be replaced by one or more layers which merely have to satisfy the condition of not being detached again by the subsequent processing step of deposition of the emitting layer from solution.

The devices are characterized by standard methods, and the OLED examples given have not yet been optimized. Table 1 summarizes the data obtained. In the case of the processed devices, it is evident here that the materials according to the invention have superior efficiency and/or lifetime to those available previously (comparative example). The OLED here exhibits the following layer structure: I) cathode (Ba/Al: 3 nm/150 nm), II) emitting layer (80 nm; 47.5% by weight of TMM-1+47.5% by weight of TMM-2+5% by weight of TE), III) interlayer (20 nm), IV) buffer layer (80 nm; PEDOT) and V) anode.

TABLE 1

Results with materials processed from solution in the device configuration indicated

| Ex. | EML 80 nm | Max. eff. [cd/A] | Voltage [V] at 100 cd/m$^2$ | CIE (x, y) | Lifetime [h], initial luminance 1000 cd/m$^2$ |
|---|---|---|---|---|---|
| 7 (comp) | TMM-1:TMM-2:TE-C | 8.5 | 5.3 | 0.64/0.36 | 10500 |
| 8 | TMM-1:TMM-2:TE-1 | 12.8 | 4.8 | 0.64/0.36 | 28500 |
| 9 | TMM-1:TMM-2:TE-2 | 12.4 | 5.0 | 0.64/0.37 | 25000 |
| 10 | TMM-1:TMM-2:TE-3 | 11.1 | 4.9 | 0.66/0.36 | 30500 |
| 11 | TMM-1:TMM-2:TE-4 | 11.8 | 5.0 | 0.67/0.35 | 26000 |
| 12 | TMM-1:TMM-2:TE-5 | 11.4 | 4.9 | 0.68/0.36 | 23500 |
| 13 | TMM-1:TMM-2:TE-6 | 13 | 4.8 | 0.64/0.35 | 22000 |

The invention claimed is:

1. A compound according to Formula (9),

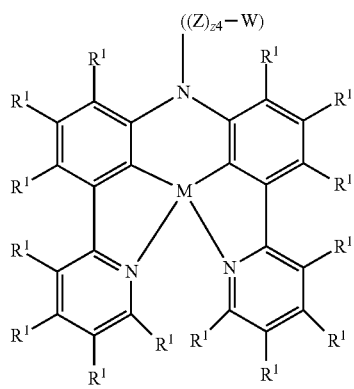

Formula (9)

where the following applies to the symbols and indices used:

M is Pt;

z4 is 0 or 1;

W is, identically or differently on each occurrence selected from the compound having the general Formula (70) or (64)

Formula (70)

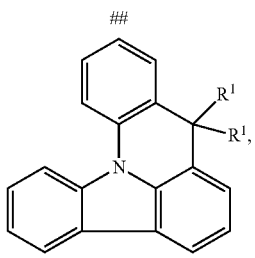

T is selected, identically or differently on each occurrence, and is $—C(R^1)_2$, $—Si(R^1)_2$, $—N$, $—NR^1$, $—O$, $—S$, $—C(=O)$, $—S(=O)$, $—SO_2$, $—CF_2$, $—SF_4$, $—P$, $—P(=O)R^1$, $—PF_2$, $—P(=S)R^1$, $—As$, $—As(=O)$, $—As(=S)$, $—Sb$, $—Sb(=O)$ or $—Sb(=S)$;

Formula (64)

the binding of W to either Z or the metal M-bearing core occurs via the position as indicated by ## of Formula (70) or ## of Formula (64) and where ## gives the position where the binding occurs of W to either Z or the meta M-bearing core of Formula (64);

X is, identically or differently on each occurrence selected from $CR^1$ or N and when the binding occurs via X in ring E' then X is $CR^1$ and $R^1$ is replaced by the bond;

U is $NR^1$;

V is selected, independently on each occurrence, from $C(R^1)_2$, $NR^1$, O and S, $R^1$ is, identically or differently on each occurrence, H, D, F, Cl, Br, I, $N(R^2)_2$, CN, $NO_2$, $Si(R^2)_3$, $B(OR^2)_2$, C(=O)R², P(=O)(R²)₂, S(=O)R², S(=O)₂R², OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals R², where one or more non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R², or an aryloxy or heteroaryloxy group having 5 to 60 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals R², or a combination of two or more of these groups; two or more radicals R¹ here may also form a mono- or polycyclic, aliphatic, aromatic and/or benzo-fused ring system with one another;

R² is, identically or differently on each occurrence, H, D, F, Cl, Br, I, N(R³)₂, CN, NO₂, Si(R³)₃, B(OR³)₂, C(=O)R³, P(=O)(R³)₂, S(=O)R³, S(=O)₂R³, OSO₂R³, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R³, or an aryloxy or heteroaryloxy group having 5 to 60 aromatic ring atoms, which is optionally substituted by one or more radicals R³, or a diarylamino group, diheteroarylamino group or arylheteroarylamino group having 10 to 40 aromatic ring atoms, which is optionally substituted by one or more radicals R³, or a combination of two or more of these groups; two or more adjacent radicals R² here may form a mono- or polycyclic, aliphatic or aromatic ring system with one another;

R³ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents R³ here may also form a mono- or polycyclic, aliphatic or aromatic ring system with one another;

r is 1;
t is 1;
v is 0 or 1; if v=0 then ring D' is a 5 membered ring;
Z is, identically or differently on each occurrence, a group of formula (16), (17) or (18)

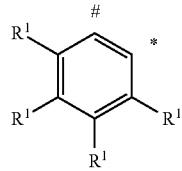

Formula (16)

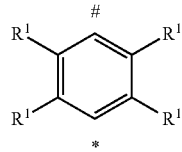

Formula (17)

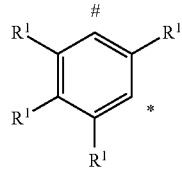

Formula (18)

wherein # and * denote the positions to which W and the metal M-bearing core bind.

2. The compound according to claim 1, wherein R¹ is, identically or differently on each occurrence, selected from the following Formulae (84) to (242)

Formula (84)

Formula (85)

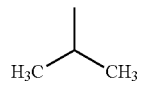

Formula (86)

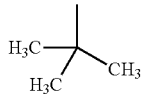

Formula (87)

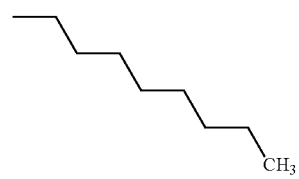

Formula (88)

Formula (89)

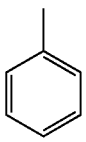

Formula (90)

-continued
Formula (91)
Formula (92)
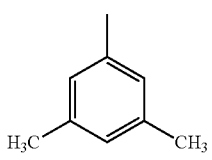
Formula (93)
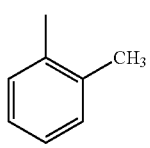
Formula (94)
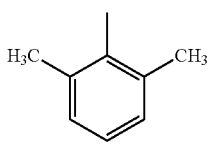
Formula (95)
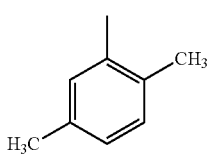
Formula (96)
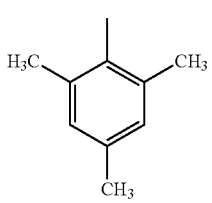
Formula (97)
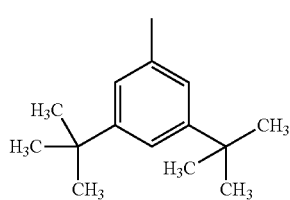
Formula (98)
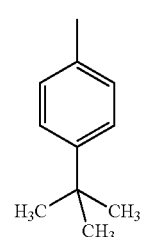
Formula (99)
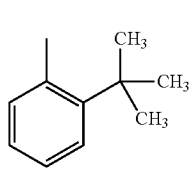
-continued
Formula (100)
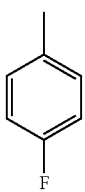
Formula (101)
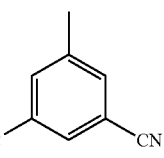
Formula (102)
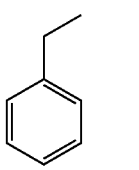
Formula (103)
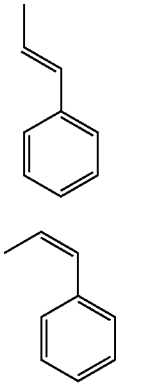
Formula (104)
Formula (105)
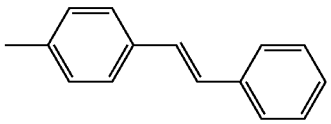
Formula (106)
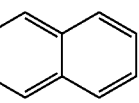
Formula (107)
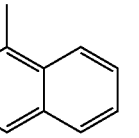
Formula (108)
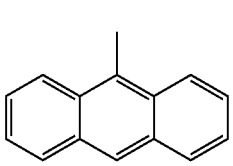
Formula (109)
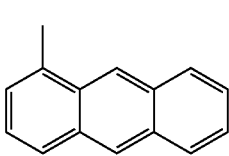

Formula (110)
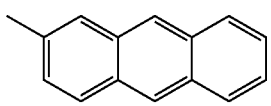
Formula (111)
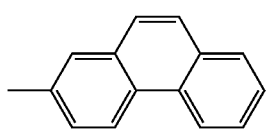
Formula (112)
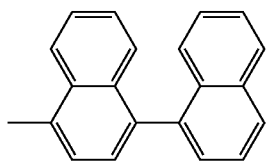
Formula (113)
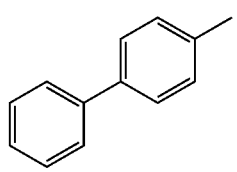
Formula (114)
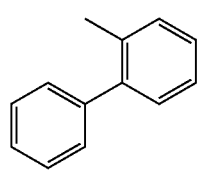
Formula (115)
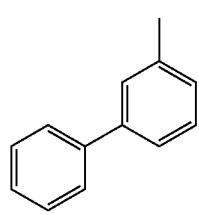
Formula (116)
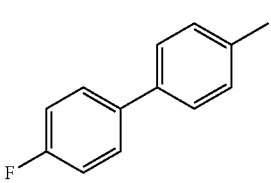
Formula (117)
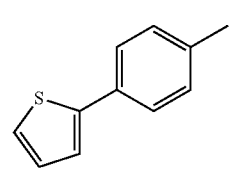
Formula (118)
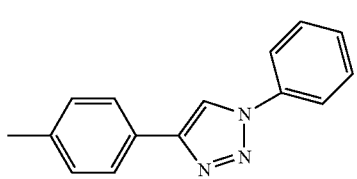
Formula (119)
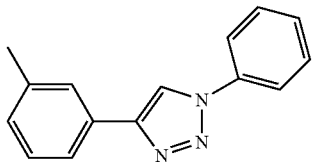
Formula (120)
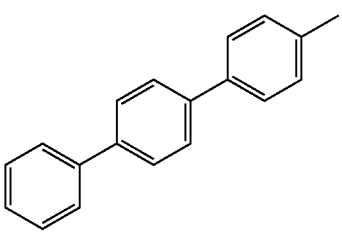
Formula (121)
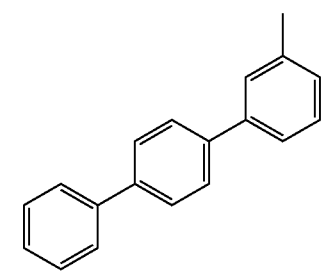
Formula (122)
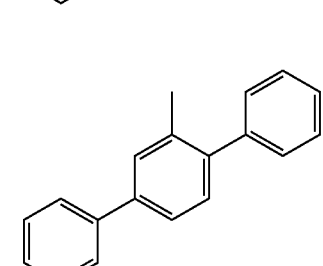
Formula (123)
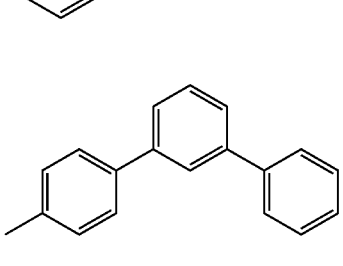
Formula (124)
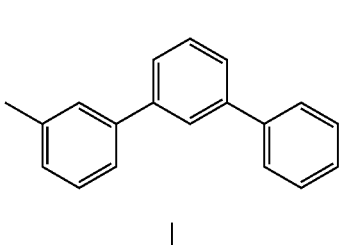
Formula (125)
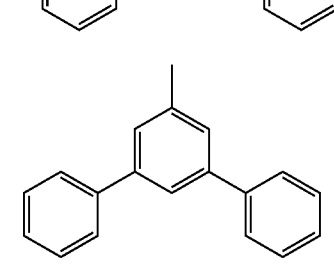

Formula (126)
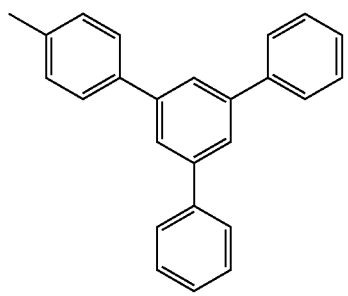
Formula (127)
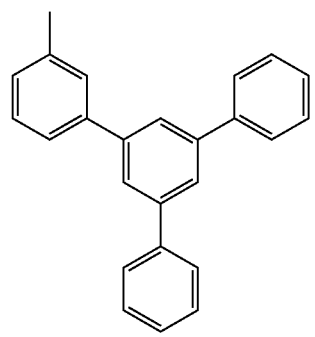
Formula (128)
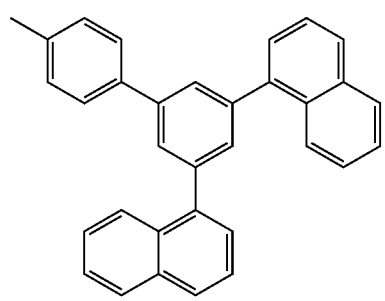
Formula (129)
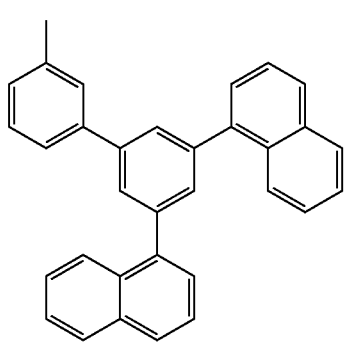
Formula (130)
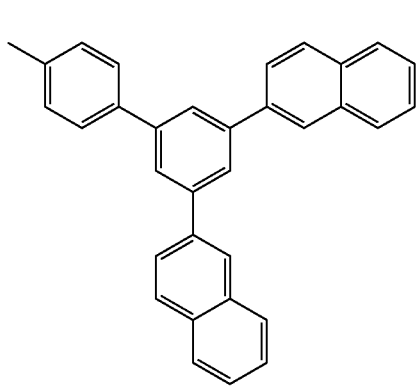
Formula (131)
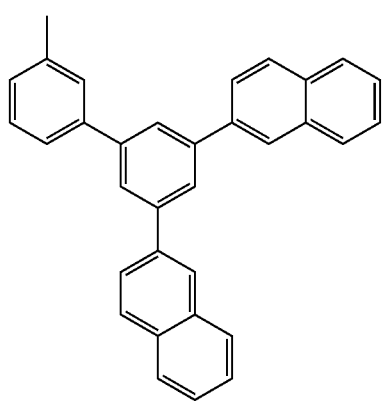
Formula (132)
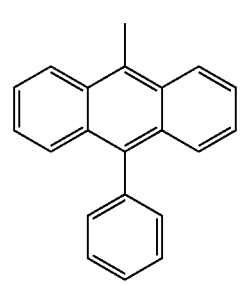
Formula (133)
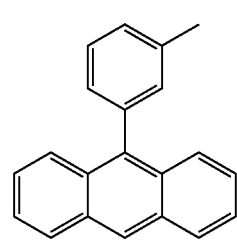
Formula (134)
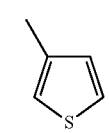
Formula (135)
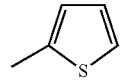
Formula (136)
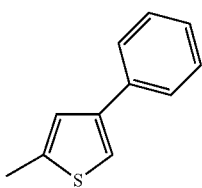
Formula (137)

| | |
|---|---|
| 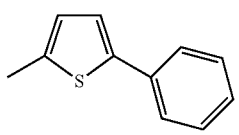 | Formula (138) |
| 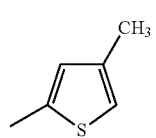 | Formula (139) |
| 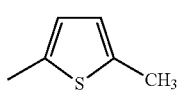 | Formula (140) |
| 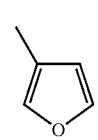 | Formula (141) |
| 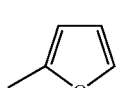 | Formula (142) |
| 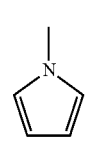 | Formula (143) |
| 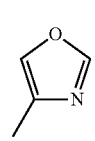 | Formula (144) |
| 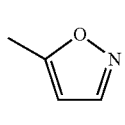 | Formula (145) |
| 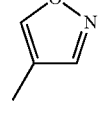 | Formula (146) |
| 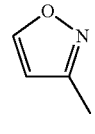 | Formula (147) |
| 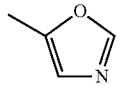 | Formula (148) |
| 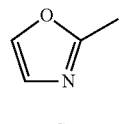 | Formula (149) |
| 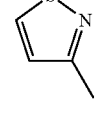 | Formula (150) |
| 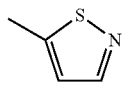 | Formula (151) |
| 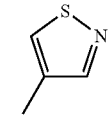 | Formula (152) |
| 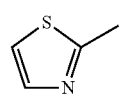 | Formula (153) |
| 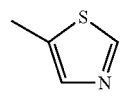 | Formula (154) |
| 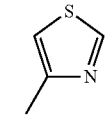 | Formula (155) |
| 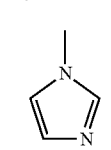 | Formula (156) |
| 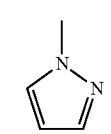 | Formula (157) |
| 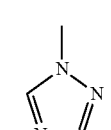 | Formula (158) |
| 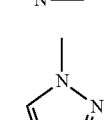 | Formula (159) |
| 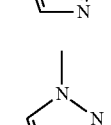 | Formula (160) |
| 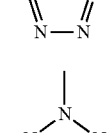 | Formula (161) |
| 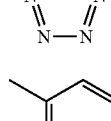 | Formula (162) |
| 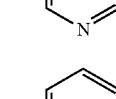 | Formula (163) |

| | |
|---|---|
| Formula (164) 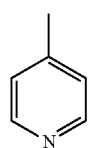 | Formula (175) 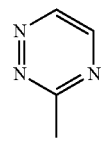 |
| Formula (165) 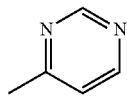 | Formula (176) 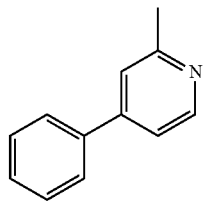 |
| Formula (166) 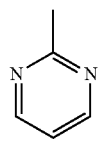 | |
| Formula (167) 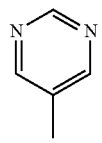 | Formula (177) 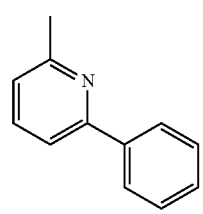 |
| Formula (168) 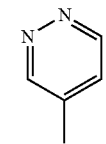 | Formula (178) 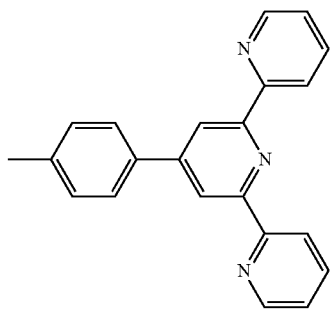 |
| Formula (169) 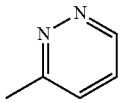 | |
| Formula (170) 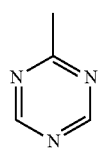 | Formula (179) 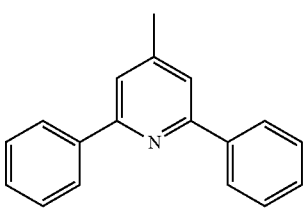 |
| Formula (171) 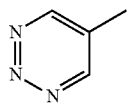 | Formula (180) 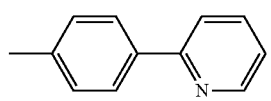 |
| Formula (172) 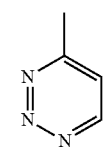 | Formula (181) 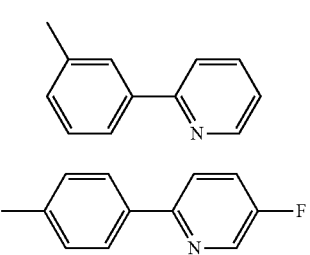 |
| Formula (173) 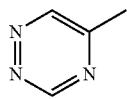 | |
| Formula (174) 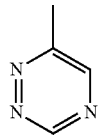 | Formula (182) |

Formula (183)
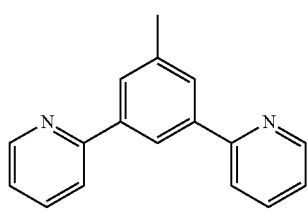
Formula (184)
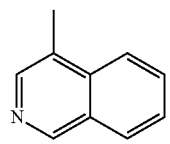
Formula (185)
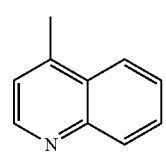
Formula (186)
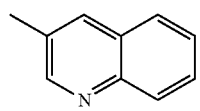
Formula (187)
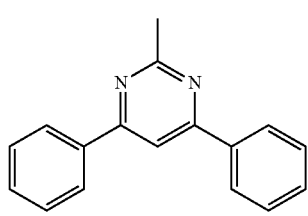
Formula (188)
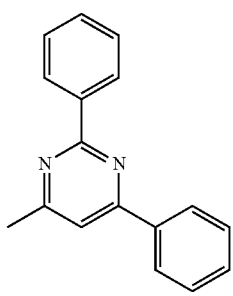
Formula (189)
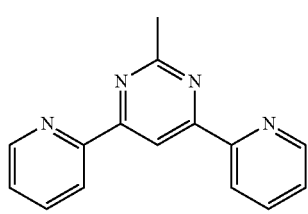
Formula (190)
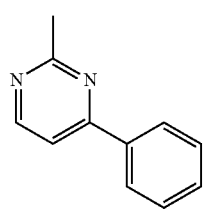
Formula (191)
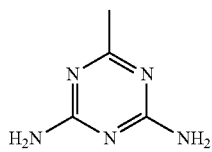
Formula (192)
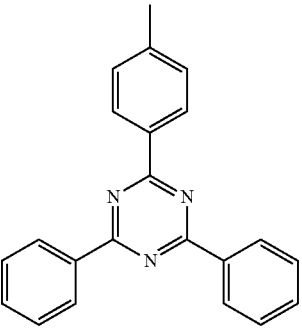
Formula (193)
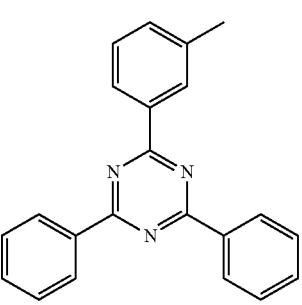
Formula (194)
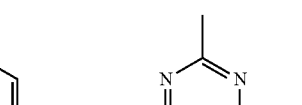
Formula (195)
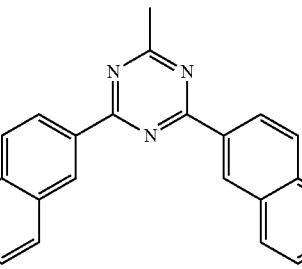
Formula (196)
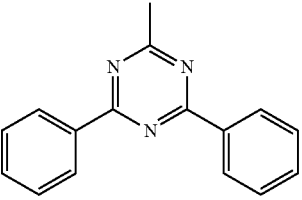

Formula (197)
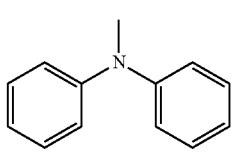
Formula (198)
Formula (199)
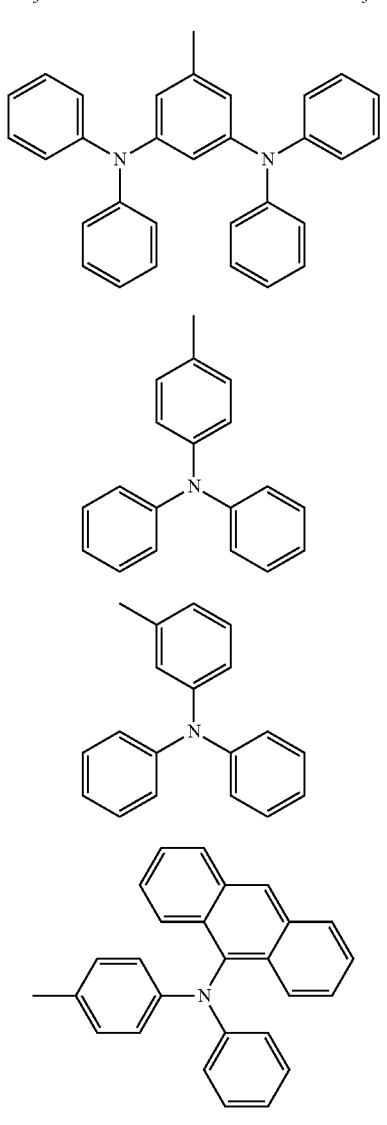
Formula (200)
Formula (201)
Formula (202)
Formula (203)
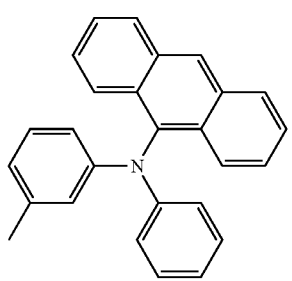
Formula (204)
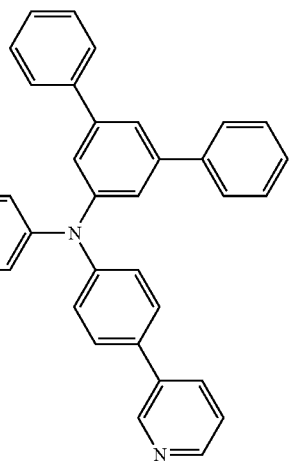
Formula (205)
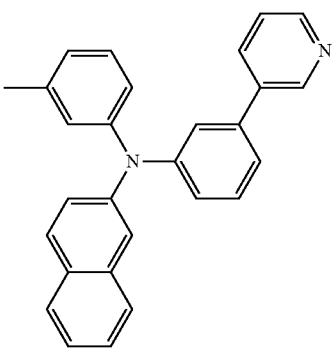
Formula (206)
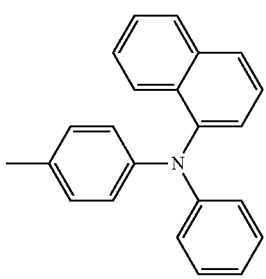
Formula (207)
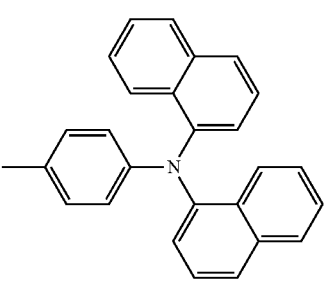

Formula (208)
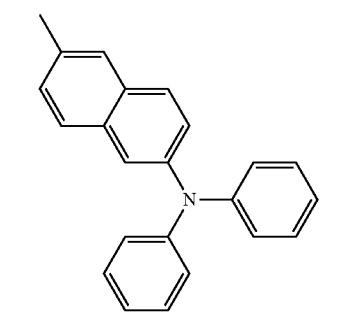
Formula (209)
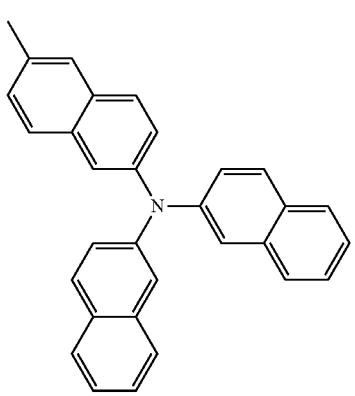
Formula (210)
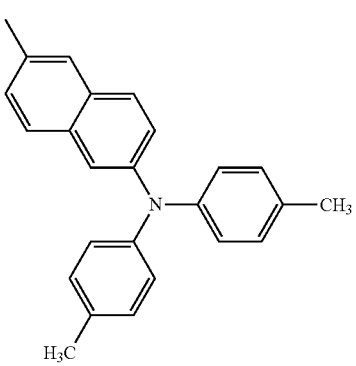
Formula (211)
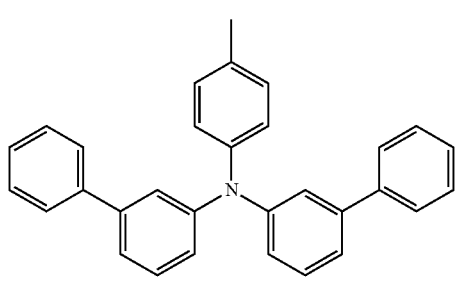
Formula (212)
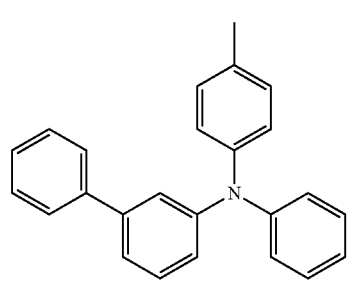
Formula (213)
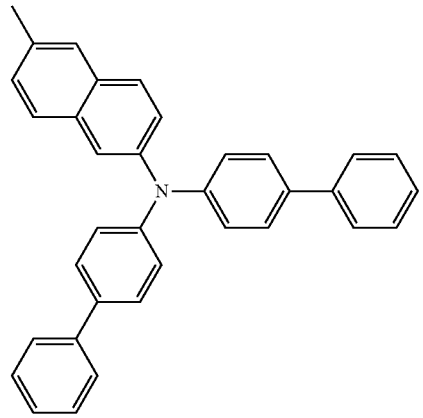
Formula (214)
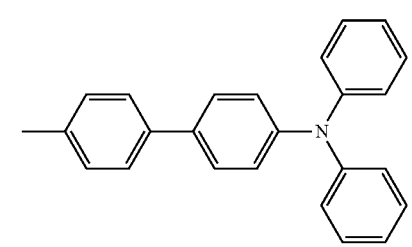
Formula (215)
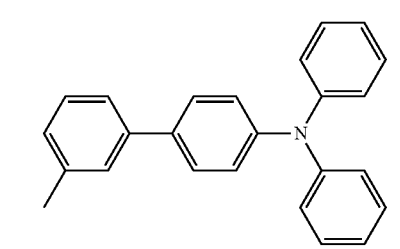
Formula (216)
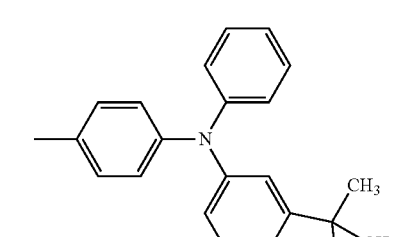
Formula (217)
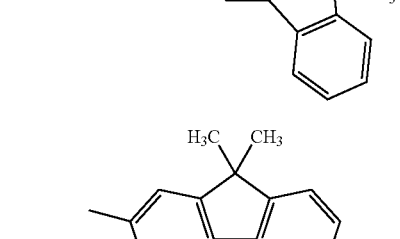
Formula (218)
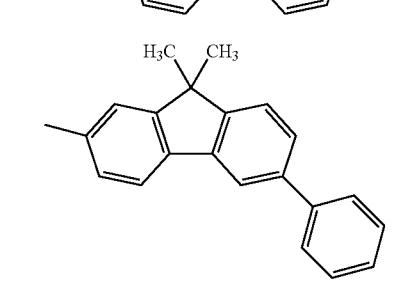

Formula (219)
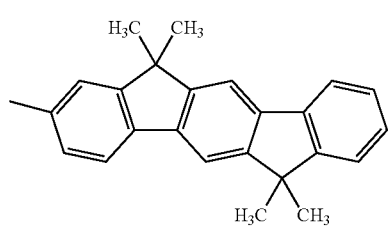
Formula (220)
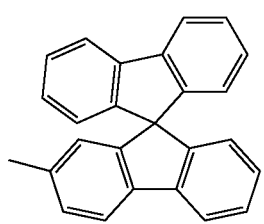
Formula (221)
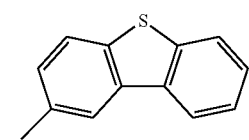
Formula (222)
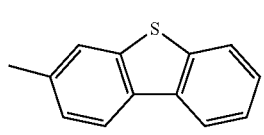
Formula (223)
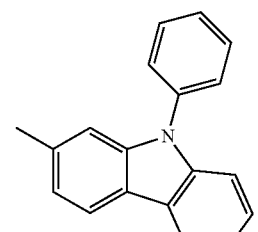
Formula (224)
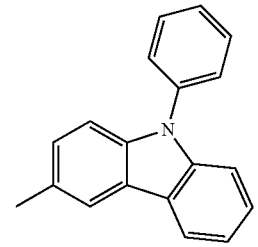
Formula (225)
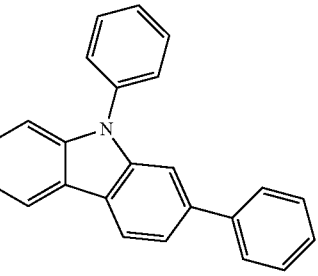
Formula (226)
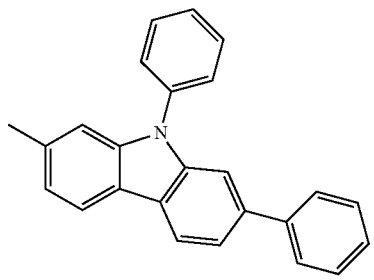
Formula (227)
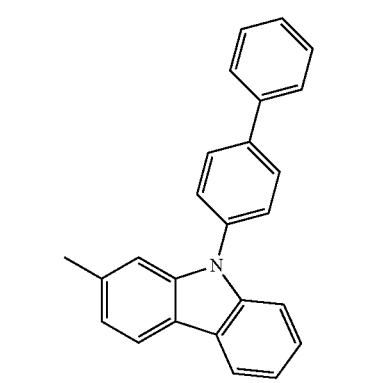
Formula (228)
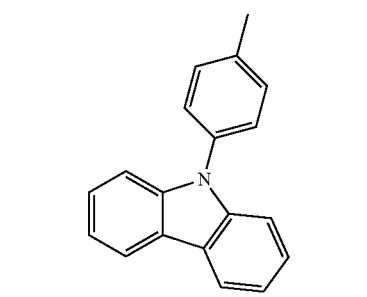
Formula (229)
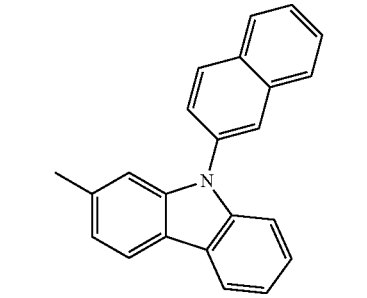
Formula (230)
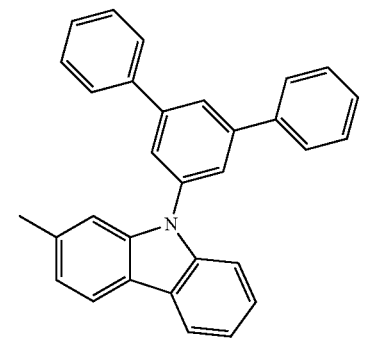

Formula (231)
Formula (232)
Formula (233)
Formula (234)
Formula (235)
Formula (236)
Formula (237)
Formula (238)
Formula (239)
Formula (240)
Formula (241)
Formula (242)
Formula (242a)
Formula (242b)
Formula (242c)
Formula (242d)

Formula (242e)

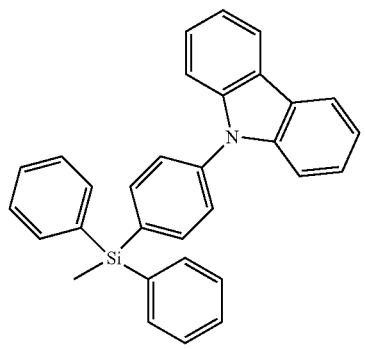

Formula (242f)

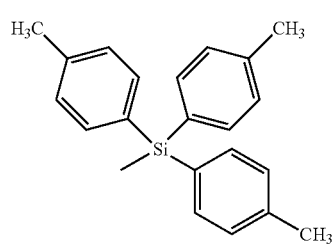

Formula (242g)

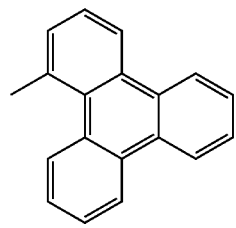

Formula (242h)

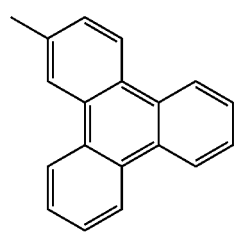

wherein the $R^1$ having the Formulae (84) to (242) can be, identically or differently on each occurrence, substituted with one or more $R^2$ and wherein the lines indicate the position of binding.

3. The compound according to claim 1, wherein W is, identically or differently on each occurrence, and is Formula (70).

4. The compound according to claim 1, wherein the compound of the formula (I) is of the formula TE-4, TE-5 or TE-6

TE-3

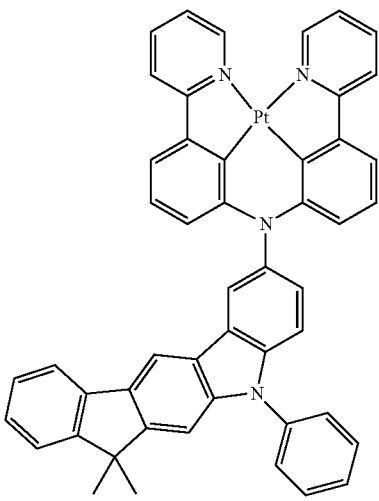

TE-4

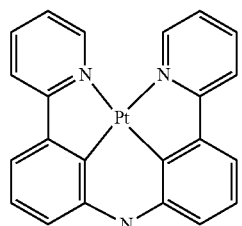

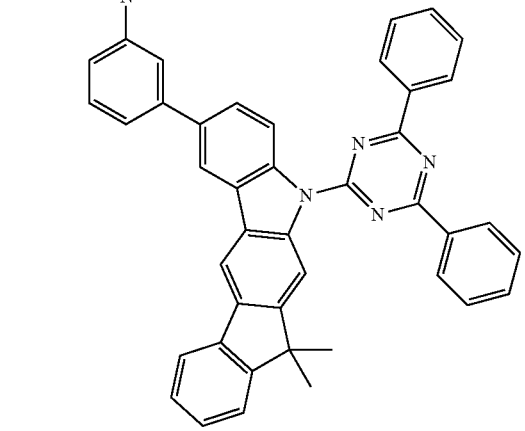

TE-6

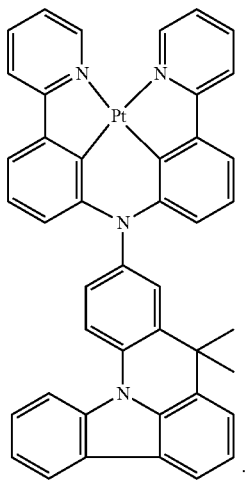

5. A composition comprising at least one compound according to claim 1 and at least one organic functional material selected from hole transport material (HTM), hole injection material (HIM), electron transport material (ETM), electron injection material (EIM), hole blocking material (HBM), exciton blocking material (ExBM), host or matrix material, fluorescent emitter, phosphorescent emitter.

6. The composition according to claim 5, wherein the at least one organic functional material is a matrix material selected from ketones, phosphinoxides, sulfoxides, sulfones, triarylamines, carbazoles, indolocarbazoles, indenocarbazoles, azacarbazoles, bipolar matrix materials, silanes, azaborolenes, boronesters, triazines, zinc complexes, diaza- or tetraazasiloles or diazaphospholes or mixtures thereof.

7. A formulation comprising at least one compound according to claim 1 and at least one solvent.

8. An electronic device which comprises the compound according to claim 1.

9. The electronic device according to claim 8, wherein the device is an organic electroluminescent device, an organic light emitting diode, polymer light emitting diode, an organic integrated circuit, an organic field effect transistor, an organic thin film transistor, an organic light emitting transistor, an organic solar cell, an organic optical detector, an organic photoreceptor, an organic field quenching device, a light emitting electrochemical cell, or an organic laser diode.

10. An electronic device which comprises the composition according to claim 6 wherein the device is an organic electroluminescent device, an organic light emitting diode, polymer light emitting diode, an organic integrated circuit, an organic field effect transistor, an organic thin film transistor, an organic light emitting transistor, an organic solar cell, an organic optical detector, an organic photoreceptor, an organic field quenching device, a light emitting electrochemical cell, or an organic laser diode and the composition is in one or more light emitting layers.

11. An electroluminescent device comprising at least one compound according to claim 1.

12. A cosmetic which comprises the electroluminescent device according to claim 11.

13. The compound according to claim 1, wherein W is, identically or differently on each occurrence, and is of the Formula (64).

14. The compound according to claim 1, wherein W is, identically or differently on each occurrence, selected from a compound of the following Formulae (78) to (83)

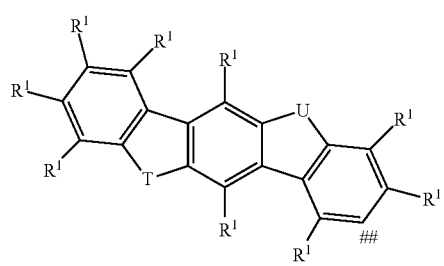

Formula (78)

-continued

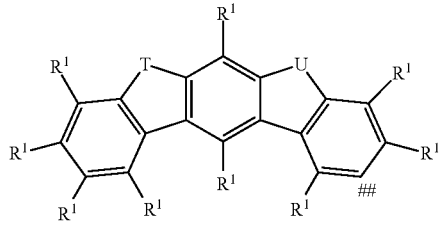

Formula (79)

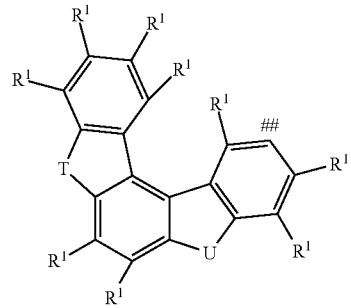

Formula (80)

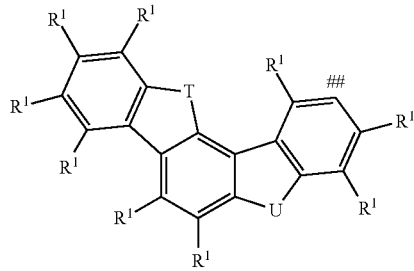

Formula (81)

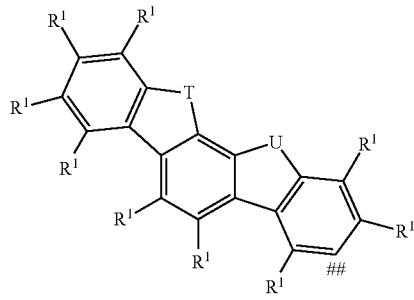

Formula (82)

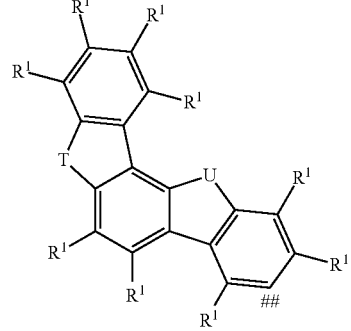

Formula (83)

wherein ## denotes the position of binding between W and Z or the metal M-bearing core and
T is $C(R^1)_2$, $NR^1$ or O and
U is $NR^1$.

* * * * *